US012186340B2

(12) United States Patent
Morrison et al.

(10) Patent No.: US 12,186,340 B2
(45) Date of Patent: Jan. 7, 2025

(54) SYNTHETIC ANTIMICROBIAL MINERAL COMPOSITIONS, METHODS OF MAKING AND USING SAME

(71) Applicant: LAWRENCE LIVERMORE NATIONAL SECURITY, LLC, Livermore, CA (US)

(72) Inventors: Keith David Morrison, Livermore, CA (US); Gabriela G. Loots, Oakland, CA (US); Ty James Samo, Walnut Creek, CA (US); Kelly Anne Martin, Dublin, CA (US)

(73) Assignee: LAWRENCE LIVERMORE NATIONAL SECURITY, LLC, Livermore, CA (US)

( * ) Notice: Subject to any disclaimer, the term of this patent is extended or adjusted under 35 U.S.C. 154(b) by 172 days.

(21) Appl. No.: 17/358,929

(22) Filed: Jun. 25, 2021

(65) Prior Publication Data

US 2022/0000912 A1    Jan. 6, 2022

Related U.S. Application Data

(60) Provisional application No. 63/044,639, filed on Jun. 26, 2020.

(51) Int. Cl.
| | |
|---|---|
| *A61K 33/26* | (2006.01) |
| *A61L 15/18* | (2006.01) |
| *A61L 15/44* | (2006.01) |
| *B33Y 70/10* | (2020.01) |
| *B33Y 80/00* | (2015.01) |
| *C08L 83/04* | (2006.01) |

(52) U.S. Cl.
CPC .............. *A61K 33/26* (2013.01); *A61L 15/18* (2013.01); *A61L 15/44* (2013.01); *B33Y 70/10* (2020.01); *B33Y 80/00* (2014.12); *C08L 83/04* (2013.01)

(58) Field of Classification Search
CPC ......... A61K 33/26; A61L 15/18; A61L 15/44; B33Y 70/10
See application file for complete search history.

(56) References Cited

U.S. PATENT DOCUMENTS

| | | | |
|---|---|---|---|
| 5,750,036 | A | 5/1998 | Sivavec |
| 6,896,909 | B2 | 5/2005 | Fanelli |
| 2008/0184618 | A1 | 8/2008 | Darlington et al. |
| 2009/0148484 | A1 | 6/2009 | Lin et al. |
| 2013/0004544 | A1 | 1/2013 | Metge et al. |
| 2018/0021374 | A1* | 1/2018 | Tuba .................... A61K 9/0014 424/489 |

FOREIGN PATENT DOCUMENTS

| | | | | |
|---|---|---|---|---|
| GB | 2493933 | A * | 2/2013 | ............. A61L 27/24 |
| WO | WO-99/20105 | A1 | 4/1999 | |

OTHER PUBLICATIONS

Ogawa, Makoto, Takayuki Matsutomo, and Tomohiko Okada. "Preparation of iron-containing hectorite-like swelling silicate." Bulletin of the Chemical Society of Japan 82.3 (2009): 408-412. (Year: 2009).*
Alleva et al., alpha-Lipoic acid supplementation inhibits oxidative damage, accelerating chronic wound healing in patients undergoing hyperbaric oxygen therapy, Biochem. Biophys. Res. Commun. 333(2):404-10 (2005).
Bjarnsholt et al., Applying insights from biofilm biology to drug development—can a new approach be developed?, Nat. Rev. Drug Discov., 12(10):791-808 (2013).
Blanchard et al., Arsenic incorporation into FeS2 pyrite and its influence on dissolution: a DFT study, Geochimica et Cosmochimica Acta, 71(3):624-30 (2007).
Brown et al., Antibacterial drug discovery in the resistance era, Nature, 529:336-43 (2016).
Carrado et al., A study of organo-hectorite clay crystallization, Clay Minerals, 32:29-40 (1997).
Childs, Biofilm: The pathogenesis of slime glycocalyx, Orthop. Nurs., 27(6):361-9 (2008).
Cohn et al., Pyrite induced hydroxyl radical formation nad its effect on nucleic acids, Geochem. Trans., 7:3 (2006).
Costerton et al., Bacterial biofilms: A common cause of persistent infections, Science, 284:1318-22 (1999).
Dewitt et al., The bactericidal and fungicidal action of copper salts: studies on the biochemistry and chemotherapy of tuberculosis, XV, J. Infect. Dis., 18:368-82 (1916).
Drabek et al., Synthesis and Structure of Single-Crystal Maracasite, IN: Mao et al. (eds.), Mineral Deposit Research: Meeting the Global Challenge, Springer (2005).
Forbes et al., Preparing the ground for tissue regeneration: from mechanism to therapy, Nat. Med., 20(8):857-69 (2014).
Galbraith et al., Super-resolution microscopy at a glance, J. Cell Sci., 124(Pt 10):1607-11 (2011).
Gartman et al., Comparison of pyrite (FeS2) synthesis mechanisms to reproduce natural FeS2 nanoparticles found at hydrothermal vents, Geochimica et Cosmochimica Acta, 120:447-58 (2013).
Gethin, The significance of surface pH in chronic wounds, Wounds UK, 3(3):52-56 (2007).
Goeres et al., A method for growing a biofilm under low shear at the air-liquid interface using the drip flow biofilm reactor, Nat. Protoc., 4(5):783-8 (2009).
Gottrup et al., Use of Oxygen Therapies in Wound Healing, J. Wound Care, 26(Sup5):S1-S4 (2017).
Gotz, Staphylococcus and biofilms, Mol. Microbiol., 43(5):1367-78 (2002).
Harrison et al., High-throughput metal susceptibility testing of microbial biofilms, BMC Microbiology, 5(53): (2005).

(Continued)

*Primary Examiner* — Abigail Vanhorn
(74) *Attorney, Agent, or Firm* — MARSHALL, GERSTEIN & BORUN LLP

(57) ABSTRACT

Provided herein are pharmaceutical compositions comprising a $Fe^{2+}$-exchanged fluorinated synthetic smectite and a synthetic semiconducting metal sulfide. The compositions can be used to treat topical conditions and gastrointestinal ailments, and can be incorporated into wound dressings, hydrogels, personal protective equipment, and 3D printed articles. Also provided are methods of synthesizing the $Fe^{2+}$-exchanged fluorinated synthetic smectite and methods of making the synthetic semiconducting metal sulfide.

21 Claims, 37 Drawing Sheets

(56) References Cited

OTHER PUBLICATIONS

Hatzenpichler et al., In situ visualization of newly synthesized proteins in environmental microbes using amino acid tagging and click chemistry, Environ. Microbiol., 16(8):2568-90 (2014).

Jonkman et al., An introduction to the wound healing assay using live-cell microscopy, Cell Adh. Migr., 8(5):440-51 (2014).

Kaufman et al., Topical acidification promotes healing of experimental deep partial thickness skin burns: a randomized double-blind preliminary study, Burns Inc. Therm. Inj., 12(2):84-90 (1985).

Lemire et al., Antimicrobial activity of metals: mechanisms, molecular targets and applications, Nat. Rev. Microbiol., 11(6):371-84 (2013).

Lennie et al., Synthesis and Rietveld crystal structure refinement of mackinawite, tetragonal FeS, Mineralogical Magazine., 59:677-83 (1995).

Leveen et al., Chemical acidification of wounds. An adjuvant to healing and the unfavorable action of alkalinity and ammonia, Ann. Surg., 178(6):745-53 (1973).

Li et al., Study of the in vitro cytotoxicity testing of medical devices, Biomed. Rep., 3(5):617-20 (2015).

Liang et al., In vitro scratch assay: a convenient and inexpensive method for analysis of cell migration in vitro, Nat. Protoc., 2(2):329-33 (2007).

Mckibben et al., Oxidation of pyrite in low temperature acidic solutions: rate laws and surface textures, Geochim. Cosmochim. Acta, 50:1509-20 (1986).

Monsuur et al., Methods to study differences in cell mobility during skin wound healing in vitro, J. Biomech., 49(8):1381-7 (2016).

Morrison et al., Mineralogical variables that control the antibacterial effectiveness of a natural clay deposit, Environ. Geochem. Health, 36(4):613-31 (2014).

Morrison et al., The anatomy of an antibacterial clay deposit: a new economic geology, Econ. Geol., 122(7):1551-70 (2017).

Morrison et al., Unearthing the Antibacterial Mechanism of Medicinal Clay: A Geochemical Approach to Combating Antibiotic Resistance, Sci. Rep., 6:19043 (2016).

Nagoba et al., Citric acid treatment of non-healing sinus of neck in a patient treated with anti-Koch therapy, Int Wound J., 14(6):1411-2 (2017).

O'Neill, Tackling drug-resistant infections globally: Final report and recommendations. The Review on Antimicrobial Resistance, Rev. Antimicrob. Resist. (2014).

Pendleton et al., Clinical relevance of the ESKAPE pathogens, Expert Rev. Anti Infect Ther., 11(3):297-308 (2013).

Puthussery et al., Colloidal iron pyrite (FeS2) nanocrystal inks for thin-film photovoltaics, J. Am. Chem. Soc., 133(4):716-9 (2011).

Renner et al., Detection of ESKAPE Bacterial Pathogens at the Point of Care Using Isothermal DNA-Based Assays in a Portable Degas-Actuated Microfluidic Diagnostic Assay Platform, Appl. Environ. Microbiol., 83(4):e02449-16 (2017).

Rimstidt et al., Pyrite oxidation: a state of the art assessment of the reaction mechanism, Geochim. Cosmochim. Acta, 67:873-80 (2003).

Roy et al., Dermal wound healing is subject to redox control, Mol. Ther., 13(1):211-20 (2006).

Savage et al., Impurities and heterogeneity in pyrite: influences on electrical properties and oxidation products, Appl. Geochem., 23(2):103-20 (2008).

Schlafer et al., Confocal microscopy imaging of the biofilm matrix, J. Microbiol. Methods, 138:50-59 (2017).

Schlafer et al., Ratiometric imaging of extracellular pH in bacterial biofilms with C-SNARF-4, Appl. Environ. Microbiol., 81(4):1267-73 (2015).

Schoonen et al., Effect of temperature and illumination on pyrite oxidation between pH2 and 6, Geochm. T, 1(1):23 (2000).

Schoonen et al., Role of hydrogen peroxide and hydroxyl radical in purite oxidation by molecular oxygen, Geochim. Cosmochim. Acta, 74:4971-87 (2010).

Sen et al., Perceived hyperoxia: oxygen-induced remodeling of the reoxygenated heart, Cardiovasc. Res., 71(2):280-8 (2006).

Sherratt et al., Rapid Screening and Identification of Living Pathogenic Organisms via Optimized Bioorthogonal Non-canonical Amino Acid Tagging, Cell Chem. Biol., 24(8):1048-55 (2017).

Sines et al., Synthesis of tetragonal mackinawite-type FeS nanosheets by solvothermal crystallization, J. Solid State Chem., 196:17-20 (2012).

Stanton, Experimental studies on the synthesis of pyrite and marcasite (FeS2) from 9° to 200° C and summary of results, U.S. Geological Survey, Open-File Report 91-310 (1991).

Wang et al., Solution-processable pyrite FeS(2) nanocrystals for the fabrication of heterojunction photodiodes with visible to NIR photodetection, Adv. Mater., 24(25):3415-20 (2012).

Weller et al., Antimicrobial effect of acidified nitrite on dermatophyte fungi, Candida and bacterial skin pathogens, J. Appl. Microbiol., 90(4):648-52 (2001).

Weller et al., The effects of topical treatment with acidified nitrite on wound healing in normal and diabetic mice, Nitric Oxide, 15(4):395-9 (2006).

Williams et al., Killer clays! Natural antibacterial clay minerals, Min. Soc. Bull., 139:3-8 (2004).

Williams et al., What makes a natural clay antibacterial?, Environ. Sci. Technol., 45(8):3768-73 (2011).

Williams, Geomimicry: harnessing the antibacterial action of clays, Clay Minerals, 52:1-24 (2017).

Yuan et al., One-step synthesis of pure pyrite FeS2 with different morphologies in water, New J. Chem., 39:3571-7 (2015).

\* cited by examiner

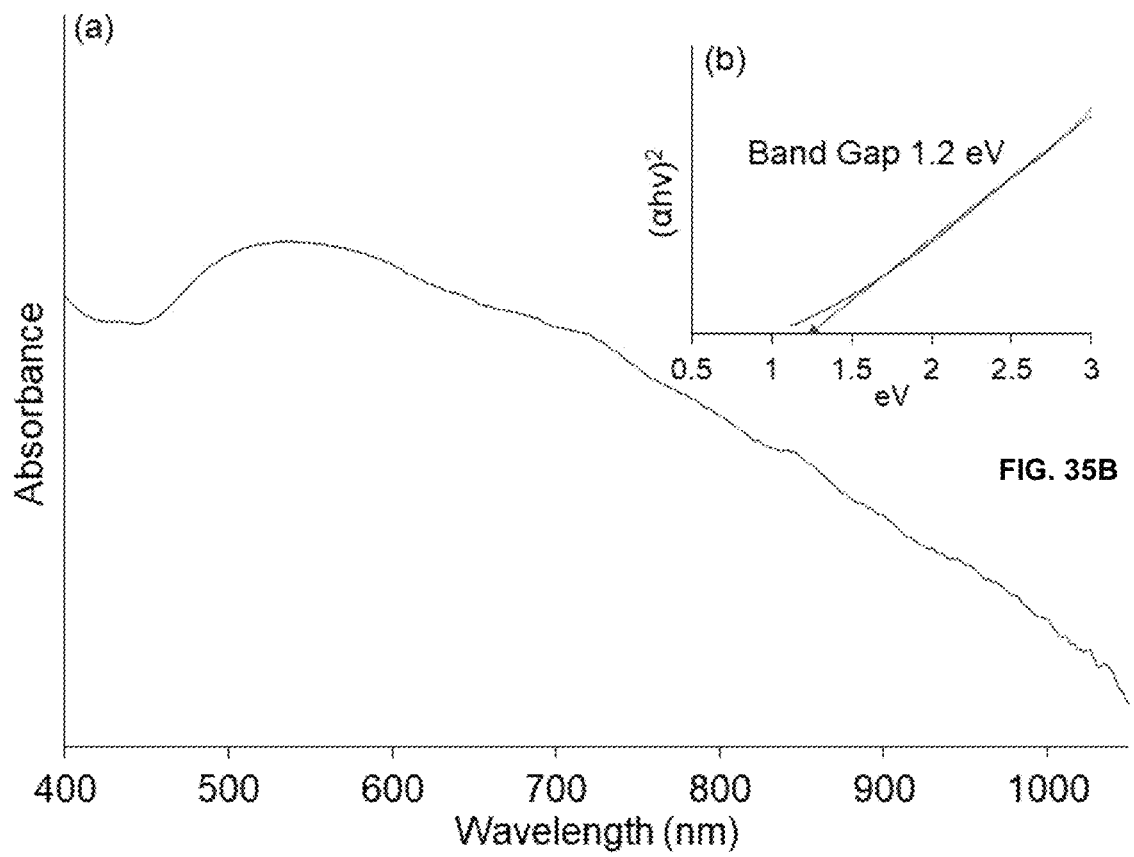
FIG. 35A
FIG. 35B
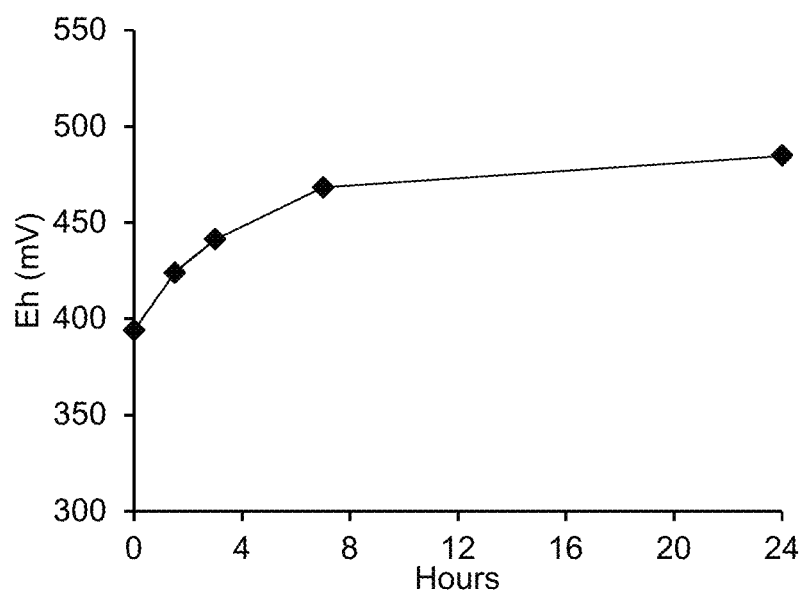
FIG. 36

SYNTHETIC ANTIMICROBIAL MINERAL COMPOSITIONS, METHODS OF MAKING AND USING SAME

CROSS-REFERENCE TO RELATED APPLICATION

The benefit of priority to U.S. Provisional Patent Application No. 63/044,639 filed Jun. 26, 2020 is hereby claimed and the disclosure is incorporated herein by reference in its entirety.

STATEMENT REGARDING FEDERALLY SPONSORED RESEARCH OR DEVELOPMENT

This invention was made with Government support under Contract No. DE-AC52-07NA27344 awarded by the United States Department of Energy. The Government has certain rights in the invention.

BACKGROUND

The overuse of traditional antibiotics in humans and animals has resulted in the emergence of stronger, more potent bacterial pathogens that are no longer treatable with conventional antibiotics, making even routine surgery a risk for acquiring antibiotic resistant infections. Antibiotic resistant pathogens are predicted to account for 10 million annual deaths worldwide by the year 2050. The pathogens include *Enterococcus* spp, *Staphylococcus aureus, Klebsiella pneumonia, Acinetobacter* spp., *Pseudomonas aeruginosa*, and *Enterobacter* spp. (ESKAPE), which represent the most common group of human pathogens that "escape" the effects of antibiotics in clinical settings. However, new antibiotic resistant bacterial strains are constantly emerging that establish resistance to new antibiotics within 2-3 years in clinical settings. For example, the Center for Disease Control (CDC) has identified antibiotic resistant *Clostridiodies difficile* infections as an urgent threat to public health due to the limited success of antibiotics and fecal transplants as treatment options. Developing new antibacterial treatments is vital to preventing the future spread of infectious diseases and the erosion of advances in human health and food sustainability made over the last century.

A resurgence of inquiry into alternative antibacterial mechanisms has emerged as human pathogens have evolved antibiotic resistance. Documented use of reduced metal-rich clays in healing necrotizing fasciitis led to renewed interest in ancient uses of minerals for healing wounds. Research on the first antibacterial clay deposit in the United States, near Crater Lake, Oregon, provided a basic understanding of the role minerals can play in killing antibiotic resistant pathogens.

One of the key components of natural antibacterial clays is the ability to release soluble metals. Studies on natural antibacterial clay deposits have implicated iron sulfides and expandable clays, such as smectite, in the antibacterial mechanism. These minerals are thought to work by buffering solution pH and redox potential and by maintaining hydration, while providing extended release of $Fe^{2+}$, $Al^{3+}$, and reactive oxygen species (ROS). However, natural samples are too variable to provide an antibacterial material with consistent properties for clinical and/or commercial settings. Moreover, the distinct mineralogical (e.g., crystal structure, particle size, etc.) and chemical (e.g., pH, redox, metal speciation, ROS, etc.) properties that control antibacterial properties are not understood. The synthesis of pharmaceutical grade mineral components are necessary to produce a product with high chemical purity and reproducible reactivity, as these properties cannot be achieved with natural samples. Thus, antibacterial mineral compositions having improved consistency and bactericidal properties are needed.

SUMMARY

Provided herein are pharmaceutical compositions comprising $Fe^{2+}$-exchanged fluorinated synthetic smectite and synthetic semiconducting metal sulfide. In embodiments, the $Fe^{2+}$ exchanged fluorinated synthetic smectite can be $Fe^{2+}$ exchanged synthetic fluorinated synthetic smectite and the synthetic semiconducting metal sulfide can be synthetic pyrite.

In various embodiments, the $Fe^{2+}$-exchanged fluorinated synthetic smectite is present in an amount of 80 wt % to 98.5 wt %, based on the total weight of the composition. In various embodiments, the $Fe^{2+}$-exchanged fluorinated synthetic smectite is present in an amount of 90 wt % to 98.5 wt %, based on the total weight of the composition.

In various embodiments, the synthetic semiconducting metal sulfide is present in an amount of 1.5 wt % to 20 wt %, based on the total weight of the composition. In various embodiments, the synthetic semiconducting metal sulfide is present in an amount of 5 wt % to 20 wt %, based on the total weight of the composition.

In various embodiments, the composition has a pH of 2 to 6.

In various embodiments, the $Fe^{2+}$-exchanged fluorinated synthetic smectite has a particle size of less than 2 μm. In various embodiments, the $Fe^{2+}$-exchanged fluorinated synthetic smectite has a particle size of 0.5 μm to 1 μm. In various embodiments, the $Fe^{2+}$-exchanged fluorinated synthetic smectite has an average surface area of 500 $m^2/g$ to 700 $m^2/g$.

In various embodiments, the $Fe^{2+}$-exchanged fluorinated synthetic smectite, at an octahedral site, comprises $Li^+$ and a divalent cation, forming a tri-octahedral smectite. The divalent cation can comprise $Mg^{2+}$, $Cu^{2+}$, $Zn^{2+}$, or $Fe^{2+}$. In various embodiments, the $Fe^{2+}$-exchanged fluorinated synthetic smectite, at an octahedral site, comprises $Li^+$ and $Mg^{2+}$.

In various embodiments, the $Fe^{2+}$-exchanged fluorinated synthetic smectite, at an octahedral site, comprises a divalent cation, a trivalent cation or a combination of the two, forming a di-octahedral smectite. In various embodiments, the $Fe^{2+}$-exchanged fluorinated synthetic, at an octahedral site, comprises one or more of $Mg^{2+}$, $Cu^{2+}$, $Zn^{2+}$, $Fe^{3+}$, $Fe^{2+}$ and $Al^{3+}$.

In various embodiments, the $Fe^{2+}$-exchanged fluorinated synthetic smectite comprises from 5 meq to 150 meq of ferrous iron ($Fe^{2+}$), per 100 g of the $Fe^{2+}$-exchanged fluorinated synthetic smectite.

In various embodiments, the synthetic semiconducting metal sulfide has a particle size of at least 1 μm. In various embodiments, the synthetic semiconducting metal sulfide has a particle size of 1 μm to 2 μm.

In various embodiments, the composition is free of arsenic, lead, cobalt, nickel, mercury, or uranium. In various embodiments, the composition is bacteriostatic. In various embodiments, the composition is bactericidal.

In various embodiments, 24 hours after hydration, the composition generates at least 7 times more reactive oxygen species (ROS) than a composition that does not comprise the synthetic semiconducting metal sulfide. In various embodiments, the ROS comprises hydrogen peroxide, hydroxyl radical, hydroperoxyl radicals, or a mixture thereof. In various embodiments, 24 hours after hydration, the composition releases at least 5 times more $Fe^{2+}$ ion than a composition that does not comprise the synthetic semiconducting metal sulfide. In various embodiments, after 24 hours of exposure to a mixture comprising at least 25 mg/mL of the composition, at least 50% of fibroblast cells are viable.

In various embodiments, the composition is for use in treating a topical condition or for administration for treating a gastrointestinal infection. In various embodiments, the topical condition is selected from the group consisting of a bacterial infection, a fungal infection, and acne. In various embodiments, the bacterial infection comprises antibiotic resistant bacteria. In various embodiments, the antibiotic resistant bacteria is selected from the group consisting of antibiotic resistant bacteria is selected from the group consisting of *Enterococcus faecium, Staphylococcus aureus, Klebsiella pneumonia, Acinetobacter baumannii, Pseudomonas aeruginosa, Enterobacter, Escherichia coli*, extended-spectrum beta lactamase positive (ESBL) *Escherichia coli, Salmonella enterica* serotype *typhimurium*, a methicillin-resistant *Staphylococcus aureus* (MRSA), *Staphylococcus epidermidis*, methicillin-resistant *Staphylococcus epidermidis* (MRSE), *Propionibacterium acnes, Clostridiodies difficile, Listeria monocytogenes, Pasteurella multocida, Proteus vulgaris, Bacillus cereus, Bordetella bronchiseptica*, and any combination thereof. In various embodiments, the gastrointestinal infection is dysentery.

Also provided herein are wound dressings comprising the composition of the disclosure suspended in a hydrogel.

Further provided herein are articles of personal protective equipment comprising the composition of the disclosure.

Further provided herein are 3D-printed articles comprising the composition of the disclosure and a siloxane resin.

Also provided herein are methods of synthesizing $Fe^{2+}$-exchanged fluorinated synthetic smectite comprising: reacting an aqueous solution comprising one or more cation sources with fumed silica nanoparticles to provide an aqueous suspension; heating the aqueous suspension at a temperature of 180° C. to 250° C. in the presence of a fluoride source to form fluorinated smectite; and admixing the fluorinated smectite and a ferrous iron source to form the $Fe^{2+}$-exchanged fluorinated synthetic smectite. The method could alternatively include reacting an aqueous solution comprising one or more cation sources with fumed silica nanoparticles and a fluoride source and then heating the aqueous suspension at a temperature 180° C. to 250° C. to form a fluorinated smectite. Still further, a fluoride source can be present during reaction of the cation source and the fumed silica nanoparticles and the aqueous suspension can be heated in the presence of a fluoride source. For example, the cation can be one or more divalent and trivalent cations. For example, the cation can be $Mg^{2+}$, $Cu^{2+}$, $Zn^{2+}$, $Fe^{3+}$, $Fe^{2+}$ and $Al^{3+}$. The cation source can be provide as a salt of the cation. For example, the cation source can be a chloride salt, such as magnesium (II) chloride, copper (II) chloride, or zinc (II) chloride or iron (II) chloride.

In various embodiments, the aqueous solution further comprises sodium hydroxide. In various embodiments, the fumed silica nanoparticles have a particle size of 300 nm or less. In various embodiments, the fumed silica nanoparticles have a particle size of 100 nm to 200 nm.

In various embodiments, the fluoride source is selected from lithium fluoride (LiF) or sodium fluoride (NaF).

In various embodiments, the aqueous suspension is heated in a hydrothermal reactor. In various embodiments, the hydrothermal reactor is lined with polytetrafluoroethylene (PTFE). In various embodiments, the aqueous suspension is heated at a temperature of 200° C. for at least 3 days. In various embodiments, the aqueous suspension is heated for up to 7 days.

In various embodiments, the ferrous iron source is selected from the group consisting of iron(II) sulfate hexahydrate, iron(II) chloride, iron(II) chloride anhydrous, ammonium iron(II) sulfate hexahydrate, and any combination thereof. In various embodiments, the ferrous iron source has a concentration of 5 mM to 150 mM.

In various embodiments, the admixing of the fluorinated smectite and ferrous iron source is performed a single time. In various embodiments, the methods further comprise admixing the $Fe^{2+}$-exchanged fluorinated synthetic smectite with the ferrous iron source.

In various embodiments, the methods further comprise admixing the fluorinated synthetic smectite with a sodium source. In various embodiments, the sodium source is sodium chloride.

In various embodiments, the $Fe^{2+}$-exchanged fluorinated synthetic smectite has a particle size of less than 1 μm. In various embodiments, the $Fe^{2+}$-exchanged fluorinated synthetic smectite has an average cation exchange capacity of 50 to 150 meq/100 g.

Also provided herein are methods of making synthetic semiconducting metal sulfide comprising: heating a polysulfide and a solution comprising a metal source and a water-soluble polymer at a temperature of 180° C. to 250° C. to form the synthetic semiconducting metal sulfide.

In various embodiments, the polysulfide comprises a solution comprising elemental sulfur and sodium sulfide.

In various embodiments, the water-soluble polymer is selected from the group consisting of polyvinylpyrrolidone (PVP), polyvinyl alcohol (PVA), polyethylene glycol (PEG), carboxymethyl cellulose (CMC), and any combination thereof.

In various embodiments, the metal source comprises one or more of iron (II) chloride, iron (II) sulfate hexahydrate, iron (II) chloride, iron (II) chloride anhydrous, ammonium iron(II) sulfate hexahydrate, copper (II) chloride, copper (II) sulfate, copper (II) nitrate, zinc (II) chloride, zinc (II) sulfate, and zinc (II) nitrate.

In various embodiments, the methods further comprise admixing the polysulfide and the solution at a temperature of at least 70° C. prior to heating.

In various embodiments, the heating is performed in a hydrothermal reactor. In various embodiments, the hydrothermal reactor is lined with polytetrafluoroethylene (PTFE). In various embodiments, the heating is performed for at least 36 hours.

In various embodiments, the methods further comprise washing the synthetic semiconducting metal sulfide with a rinsing solvent, the rinsing solvent selected from the group consisting of water, hydrochloric acid, xylene, dichloromethane, ethanol, and any combination thereof.

In various embodiments, the synthetic semiconducting metal sulfide is in a form of microspheres. In various embodiments, the synthetic semiconducting metal sulfide has a particle size of at least 1 μm. In various embodiments, the particle size is 1 μm to 2 μm.

Further aspects and advantages will be apparent to those of ordinary skill in the art from a review of the following detailed description. The description hereafter includes specific embodiments with the understanding that the disclosure is illustrative, and is not intended to limit the invention to the specific embodiments described herein.

BRIEF DESCRIPTION OF THE DRAWINGS

FIG. 35A is a spectrum of synthetic semi-conducting metal sulfide particles suspended in de-ionized water.

FIG. 35B is a Tauc-plot of the spectrum of FIG. 35A used to extrapolate a direct band gap of 1.2 eV.

FIG. 36 is a graph showing Eh (mV) values for hydrated compositions in accordance with the disclosure.

DETAILED DESCRIPTION

Figure 1:
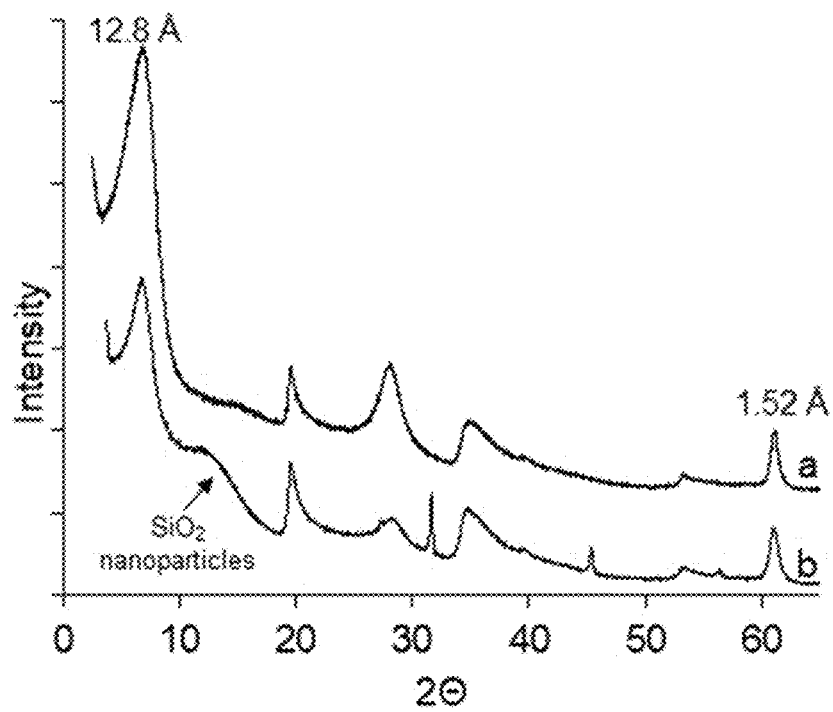
FIG. 1 is an X-ray diffraction (XRD) pattern of a synthetic fluorinated hectorite prepared according to the disclosure after (a) reacting at 200° C. for 5 days, and (b) reacting at 180° C. for 3 days.

Provided herein are pharmaceutical compositions comprising $Fe^{2+}$-exchanged fluorinated synthetic smectite and synthetic semi-conducting metal sulfide. For example, the synthetic metal sulfide may be pyrite. For example, the fluorinated synthetic smectite may be fluorinated synthetic hectorite. Advantageously, the pharmaceutical compositions of the disclosure are suitable for use in a pharmaceutical application and can mimic the antibacterial activity of natural samples (e.g., natural smectite and natural pyrite), while avoiding many of the disadvantages of naturally sourced clays, such as chemical (sometimes toxic) impurities and inconsistency of components present. For example, in embodiments, the pharmaceutical compositions disclosed herein are free of toxic elements, such as arsenic, lead, cobalt, nickel, mercury, and/or uranium. The combination of the $Fe^{2+}$-exchanged-F-synthetic smectite and synthetic semiconducting metal sulfide which is of a pharmaceutical grade, is a combination that is not naturally occurring that provides desirable and tunable ROS generation and $Fe^{2+}$ ion release rates, thereby allowing for tailored properties of the composition for a desired end use. This reactivity cannot be reproduced consistently in compositions prepared from natural samples and requires fully synthetic mineral components to produce a viable product for pharmaceutical applications, in particular, human health applications.

As used herein, "free of toxic elements" means that the compositions contain less than 0.1 wt %, 0.01 wt %, or 0.001 wt % of toxic elements such as arsenic, lead, cobalt, nickel, mercury, and/or uranium, such that the compositions can safely be applied to a subject (e.g., a human or mammalian skin tissue) in need of the pharmaceutical composition. Furthermore, the reactivity, as well as the pH, ferrous iron ($Fe^{2+}$) release, and hydrogen peroxide ($H_2O_2$) release of the compositions of the disclosure can be tuned to increase or decrease the redox reactions that result in the generation of reactive oxygen species (ROS) for various applications, such as wound care, livestock, and municipal biosolids treatment. The pharmaceutical compositions of the disclosure can be utilized as hydrated poultices or as hydrogel composites (e.g., dispersed within a hydrogel matrix) to effectively kill antibiotic resistant bacteria, such as ESKAPE pathogens (*Enterococcus* spp, *Staphylococcus aureus, Klebsiella pneumonia, Acinetobacter* spp., *Pseudomonas aeruginosa*, and *Enterobacter* spp.), *Escherichia coli*, extended-spectrum beta lactamase positive (ESBL) *Escherichia coli, Salmonella enterica* serotype *typhimurium*, a methicillin-resistant *Staphylococcus aureus* (MRSA), *Staphylococcus epidermidis*, methicillin-resistant *Staphylococcus epidermidis* (MRSE), *Propionibacterium acnes, Clostridiodies difficile, Listeria monocytogenes, Pasteurella multocida, Proteus vulgaris, Bacillus cereus, Bordetella bronchiseptica*, and the like.

In general, upon hydration (e.g., exposure to water, moisture, or a hydrogel matrix), the pharmaceutical compositions of the disclosure can impart antibacterial properties. Compositions of the disclosure can be useful in topical applications, for example in the treatment of a topical bacterial infection, fungal infection, or acne. Compositions of the disclosure can be useful for administration in vivo, for example, through oral or topical administration as a poultice, hydrogel or pill. Such dosage forms can be useful, for example, in treating gastrointestinal disorders. In particular, hydrating the composition can initiate a cascade of redox reactions in each of the $Fe^{2+}$-exchanged fluorinated synthetic smectite and the synthetic metal sulfides to release ferrous iron and ROS, such as hydrogen peroxide, superoxide anions, hydroperoxyl radicals, and/or hydroxyl radicals, within a self-buffered (e.g., a pH of 2 to 6) environment. Under these conditions, the released ferrous iron and ROS can inhibit the growth of and/or kill bacteria, such as antibiotic resistant bacteria. In embodiments, the pharmaceutical compositions of the disclosure are bacteriostatic (i.e., the compositions can inhibit the growth of bacteria). In embodiments, the pharmaceutical compositions of the disclosure are bactericidal (i.e., the compositions can kill existing bacteria).

Pharmaceutical Compositions $Fe^{2+}$-Exchanged Fluorinated Synthetic Smectite

Smectite clay minerals have a layered mineral structure. A smectite is a general name used for any swelling clay that has approximately 1 nm thick 2:1 sheets of tetrahedral and octahedral units respectively, separated by hydrated interlayer cations which give rise to the clay's swelling. Various smectite clays exist, such as hectorite, beidellite, montmorillonite, ferrosaponite, nontronite, sauconite, stevensite, saponite, vermiculite, yakhontovite, and zincsilite, which can each be classified based on the composition of the octahedral sheet (e.g., either dioctahedral or trioctahedral). Compositional information can found in the table below:

| Smectite Clay Species | Composition |
| --- | --- |
| Beidellite | $(Na, Ca_{0.5})_{0.3}Al_2((Si, Al)_4O_{10})(OH)_2 \cdot nH_2O$ |
| Montmorillonite | $(Na, Ca)0.33(Al, Mg)2(Si4O10)(OH)2 \cdot nH2O$ |
| Ferrosaponite | $Ca0.3(Fe2+, Mg, Fe3+)3((Si, Al)4O10)(OH)2 \cdot 4H2O$ |
| Hectorite | $Na0.3(Mg, Li)3(Si4O10)(F, OH)2$ |
| Nontronite | $Na0.3Fe2((Si, Al)4O10)(OH)2 \cdot nH2O$ |
| Saponite | $Ca0.25(Mg, Fe)3((Si, Al)4O10)(OH)2 \cdot nH2O$ |
| Sauconite | $Na0.3Zn3((Si, Al)4O10)(OH)2 \cdot 4H2O$ |
| Stevensite | $(Ca, Na)xMg3-x(Si4O10)(OH)2$ |
| Vermiculite | $Mg0.7(Mg, Fe, Al)6(Si, Al)8O20(OH)4 \cdot 8H2O$ |
| Yakhontovite | $(Ca, Na)0.5(Cu, Fe, Mg)2(Si4O10)(OH)2 \cdot 3H2O$ |
| Zincsilite | $Zn3Si4O10(OH)2 \cdot 4H2O$ |

The layered mineral structure of smectite includes approximately 1 nm sheets of alternating tetrahedral-octahedral-tetrahedral (TOT) units. These TOT units have a negative surface charge and stack together into layers with expandable interlayer sites that can exchange cations while maintaining hydration. In natural hectorite samples, for example, the tetrahedral sites include silicon (Si) tetrahedrons while the octahedral sites contain magnesium ($Mg^{2+}$) and lithium ($Li^+$) octahedrons. Hectorite clay minerals always include $Li^+$ in the octahedral sites. Natural smectites can contain toxic elements, such as arsenic, lead, cobalt, nickel, mercury, and/or uranium within its layered structure or interlayer spaces. Chemically and mineralogically pure smectite cannot be extracted from natural deposits for pharmaceutical applications, as accessory minerals (quartz, carbonates, zeolites, feldspars, iron oxides) are present, which can detrimentally interfere with the release and/or antimicrobial efficacy of $Fe^{2+}$ and ROS, as well as with the pH of the system. Therefore, this mineral cannot be mined for pharmaceutical applications that require distinct mineralogical and chemical properties that provide a consistently reproducible pharmaceutical effect (e.g., generation of reactive oxygen species).

The pharmaceutical compositions of the disclosure include a synthetic fluorinated smectite (F-synthetic smectite or syn-F-smectite). A fluorinated smectite includes fluoride (F) atoms and hydroxyl groups in the octahedral sites. While fluorinated smectite can be found in nature, it is rare, and as described above, often contains impurities and toxic elements. Moreover, natural smectite, whether fluorinated or not, does not have a uniform and consistent chemical structure, thereby limiting its use in clinical and commercial settings.

The fluorinated synthetic smectite of the disclosure can have a cation exchange capacity (CEC) of 50 meq to 150 meq, per 100 g of fluorinated synthetic smectite. For example, the fluorinated synthetic smectite can be a fluorinated synthetic hectorite and can have a CEC of 50 meq to 150 meq per 100 g of fluorinated synthetic hectorite. The surface of the fluorinated synthetic smectite, having a negative surface charge can bind to positively-charged atoms, such as ferrous iron ($Fe^{2+}$) to provide the $Fe^{2+}$-exchanged fluorinated synthetic smectite of the disclosure. In embodiments, the $Fe^{2+}$-exchanged fluorinated synthetic smectite of the pharmaceutical composition comprises from 5 meq to 150 meq of $Fe^{2+}$, per 100 g $Fe^{2+}$-exchanged fluorinated synthetic smectite, for example at least 5, 7, 10, 12, 15, 17, 20, 25, 30, 35, 40, 45, 50, or 55 meq and/or up to 40, 45, 50, 55, 60, 65, 70, 75, 80, 85, 87, 90, 95, 100, 105, 110, 115, 120, 125, 130, 135, 140, 145, or 150 meq of $Fe^{2+}$ per 100 g of $Fe^{2+}$-exchanged fluorinated synthetic smectite, such as 5 meq to 100 meq, 5 meq to 90 meq, 10 meq to 75 meq, 15 meq to 65 meq, 25 meq to 60 meq, 30 meq to 50 meq, or 35 meq to 45 meq of $Fe^{2+}$ per 100 g of $Fe^{2+}$-exchanged fluorinated synthetic smectite.

The fluorinated synthetic smectite can be, for example, a tri-octahedral smectite, which includes at an octahedral site, comprises $Li^+$ and a divalent cation. The divalent cation can comprise $Mg^{2+}$, $Cu^{2+}$, $Zn^{2+}$, or $Fe^{2+}$. For example, the $Fe^{2+}$-exchanged fluorinated synthetic smectite, at an octahedral site, comprises $Li^+$ and $Mg^{2+}$.

The fluorinated synthetic smectite can be, for example, a di-octahedral smectite, which includes, at an octahedral site, comprises a divalent cation, a trivalent cation or a combination of the two. The cation can be one or more of $Mg^{2+}$, $Cu^{2+}$, $Zn^{2+}$, $Fe^{3+}$, $Fe^{2+}$ and $Al^{3+}$.

Altering the divalent or trivalent cations can alter the layer charge of the minerals, providing control on the exchange and release of the $Fe^{2+}$ exchanged in the interlayer spaces. In embodiments, the octahedral sites comprise $Mg^{2+}$. In embodiments, the octahedral sites comprise $Cu^{2+}$. In embodiments, the octahedral sites comprise $Zn^{2+}$. In embodiments, the octahedral sites comprise $Fe^{2+}$. In embodiments, the octahedral sites comprise $Fe^{3+}$. In embodiments, the octahedral sites comprise $Al^{3+}$. In embodiments, the tetrahedral sites comprise $Al^{3+}$.

The $Fe^{2+}$-exchanged fluorinated synthetic smectite can have a particle size of less than 2 µm. For example, the $Fe^{2+}$-exchanged fluorinated synthetic smectite can have a particle size of at least 0.1, 0.2, 0.5, 0.7, 1.0, or 1.2 µm and/or up to 0.5, 0.7, 1.0, 1.5, 1.7, or 2.0 µm, such as 0.1 µm to 1.9 µm, 0.4 µm to 1.5 µm, 0.5 µm to 1.0 µm, or 0.7 µm to 1.2 µm. In embodiments, the $Fe^{2+}$-exchanged fluorinated synthetic smectite has a particle size of 0.5 µm to 1 µm. The particle sizes, as described throughout the disclosure, can correspond to average sizes or size ranges (e.g., minimum and maximum sizes, for example a d10-d90 range), for example based on a number, weight, area, or volume distribution. The sizes can similarly correspond to an approximate or equivalent diameter (e.g., for a roughly or substantially spherical particle), an approximate or equivalent maximum length (e.g., for a roughly or substantially rod or tubular particle), or an approximate or equivalent maximum width (e.g., for a roughly or substantially plate-like particle). In embodiments, at least 50%, 60%, 70%, 75%, 80%, 90%, 95%, or 99% of the $Fe^{2+}$-exchanged fluorinated synthetic smectite has a particle size of less than 2 μm, for example 0.5 μm to 1.0 μm. In embodiments, at least 90% of the $Fe^{2+}$-exchanged fluorinated synthetic smectite has a particle size of 0.5 μm to 1.0 μm.

The $Fe^{2+}$-exchanged fluorinated synthetic smectite can have an average surface area of 500 $m^2/g$ to 700 $m^2/g$. For example, the $Fe^{2+}$-exchanged fluorinated synthetic smectite can have an average surface area of at least 500, 525, 550, 575, 600, or 625 $m^2/g$ and/or up to 550, 575, 600, 625, 650, 675, or 700 $m^2/g$, such as 500 $m^2/g$ to 650 $m^2/g$, 525 $m^2/g$ to 625 $m^2/g$, 550 $m^2/g$ to 650 $m^2/g$, or 600 $m^2/g$ to 700 $m^2/g$.

The $Fe^{2+}$-exchanged fluorinated synthetic smectite can be present in the pharmaceutical compositions in an amount of 80 wt % to 98.5 wt %, based on the total weight of the composition. For example, the $Fe^{2+}$-exchanged fluorinated synthetic smectite can be present in an amount of at least 80, 82, 85, 90, 92, or 95 wt % and/or up to 92, 95, 96, 97, 98, or 98.5 wt %, based on the total weight of the composition, for example 80 wt % to 98 wt %, 85 wt % to 95 wt %, 90 wt % to 98.5 wt %, or 95 wt % to 98 wt %.

Synthetic Semiconducting Metal Sulfide

A synthetic semiconducting metal sulfide can be included in the compositions. Suitable synthetic metal sulfides will generally have band gap values of less than 4 eV. Materials with band gap values lower than 4 eV are conventionally classified as semiconductors. Suitable synthetic semiconducting metal sulfides can include, for example, pyrite $FeS_2$, acanthite $Ag_2S$, chalcocite $Cu_2S$, bornite $Cu_5FeS_4$, sphalerite $ZnS$, chalcopyrite $CuFeS_2$, and marcasite $FeS_2$.

Pyrite is a mineral having the chemical formula $FeS_2$, and is commonly known as "fool's gold." Pyrite has a cubic crystal system, and can be formed naturally at high and low temperatures in igneous, metamorphic, and sedimentary rocks around the world. Like natural smectites, natural pyrite can include impurities and toxic elements which can detrimentally impact and limit its uses in clinical and commercial applications.

The oxidation of pyrite, under neutral to alkaline pH conditions, is a function of the dissolved $O_2$ content according to Reaction 1, below. However, $Fe^{3+}$ is the major oxidant in acidic (pH<5) conditions, as shown in Reaction 2. Pyrite oxidation rates by $Fe^{3+}$ are therefore limited by oxidation rates of ferrous iron ($Fe^{2+}$) in solution by dissolved $O_2$, with a rate constant of approximately $10^{-3}$ M/min (Reaction 3). Pyrite can spontaneously generate ROS through a series of intermediate reactions (Reactions 4-6). For example, superoxide anions ($—O_2^-$) and hydrogen peroxide ($H_2O_2$) can be respectively produced via the Haber-Weiss reactions (Reactions 4 & 5), and ultimately form hydroxyl radicals ($—OH$) via the Fenton reaction (Reaction 6). Pyrite, as a semiconductor, has the ability to exchange 2 electrons at a time, making the direct formation of hydrogen peroxide possible Pyrite Oxidation Reactions:

$$2FeS_2+7O_2+2H_2O \rightarrow 2Fe^{2+}+SO_4^{2-}+4H^+ \quad (1)$$

$$FeS_2+14Fe^{3+}+8H_2O \rightarrow 15Fe^{2+}+2SO_4^{2-}+16H^+ \quad (2)$$

$$Fe^{2+}+O_2+2H^+ \rightarrow Fe^{3+}+2H_2O \quad (3)$$

Intermediate Reactions $$Fe^{2+}+O_2 \rightarrow Fe^{3+}+—O_2^- \quad (4)$$

$$Fe^{2+}+—O_2^-+2H^+ \rightarrow Fe^{3+}+H_2O_2 \quad (5)$$

$$Fe^{2+}+H_2O_2 \rightarrow —OH+OH^-+Fe^{3+} \quad (6)$$

The oxidation, release of metals and generation of ROS in other metal sulfide systems are governed by similar mechanisms. However, the reaction intermediates (i.e., superoxide, hydroperoxide, hydrogen peroxide and hydroxyl radicals) and metal speciation are altered. Mineral dissolution may also occur, providing a further source of metals.

The synthetic semiconducting metal sulfide can have a particle size of at least 0.5 μm. For example, the metal sulfide can be synthetic pyrite and have a particle size of at least 1 μm, for example about 0.5 μm to about 2 μm. A particle size of at least 0.5 μm can provide the proper size and surface area for sustained chemical reactivity of the synthetic semiconducting metal sulfide in the pharmaceutical compositions disclosed herein. For example, the synthetic semiconducting metal sulfide can have a particle size of at least 0.5, 1, 1.5, 2, 2.5, or 3 μm and/or up to 2.3, 3, 3.5, 4, or 5 μm, such as 0.5 μm to 5 μm, 0.5 μm to 2 μm, 1 μm to 5 μm, 1 μm to 3 μm, 1 μm to 2 μm, or 1.5 μm to 2 μm.

In embodiments, the synthetic semiconducting metal sulfide has a particle size of 1 μm to 2 μm. As described above, the particle sizes, as described throughout the disclosure, can correspond to average sizes or size ranges (e.g., minimum and maximum sizes, for example a d10-d90 range), for example based on a number, weight, area, or volume distribution. The sizes can similarly correspond to an approximate or equivalent diameter (e.g., for a roughly or substantially spherical particle), an approximate or equivalent maximum length (e.g., for a roughly or substantially rod or tubular particle), or an approximate or equivalent maximum width (e.g., for a roughly or substantially plate-like particle). In embodiments, at least 50%, 60%, 70%, 75%, 80%, 90%, 95%, or 99% of the synthetic semiconducting metal sulfide has a particle size of at least 0.5 μm, for example 0.5 μm to 2.0 μm. In embodiments, at least 90% of the synthetic semiconducting metal sulfide has a particle size of 0.5 μm to 2 μm.

FIGS. 35A and 35B illustrates a band gap analysis of a synthetic pyrite suitable for use in the disclosed composition. The synthetic pyrite had a particle size of 1-2 microns and a band gap of 1.2 eV.

The synthetic semiconducting metal sulfide can be present in the pharmaceutical compositions in an amount of 1.5 wt % to 20 wt %, based on the total weight of the composition. For example, the synthetic semiconducting metal sulfide can be present in an amount of at least 1.5, 2, 3, 4, 5, 7, or 10 wt % and/or up to 4, 5, 7, 10, 12, 15, or 20 wt %, based on the total weight of the composition, such as 5 wt %

Combination of $Fe^{2+}$-Exchanged-F-Synthetic Smectite and Synthetic Semiconducting Metal Sulfide in Disclosed Compositions The presence of $Fe^{2+}$-exchanged-F-synthetic smectite and synthetic semiconducting metal sulfide in the compositions disclosed herein provide benefits not achievable from naturally sourced smectites and metal sulfides. As discussed above, the synthetic versions can be prepared such that no toxic elements will be present and such that the particle size, surface area, and surface charge can be controlled to create mineral assemblages with tunable antibacterial properties, suitable for pharmaceutical applications utilizing hydrated mineral pastes, hydrogels and siloxane resins. Such features are important when developing a composition that is going to be used pharmaceutically.

Advantageously, redox cycling and cation exchange reactions taking place between the $Fe^{2+}$-exchanged-F-synthetic smectite and the synthetic semiconducting metal sulfide of the disclosure are tunable to alter the intensity and duration of $Fe^{2+}$ release and $H_2O_2$ generation over at least 24 hours and up to several weeks.

Referring to FIG. 36, when the pharmaceutical compositions of the disclosure having the $Fe^{2+}$-exchanged fluorinated synthetic smectite and the synthetic semiconducting metal sulfide produce an oxidizing environment, which can be maintained for at least 24 hours. FIG. 36 show the Eh behavior of a composition comprising $Fe^{2+}$-exchanged fluorinated synthetic smectite (95%) and the synthetic semiconducting metal sulfide (5%) measured over 24 hours. An Eh value of greater than 400 mV was maintained over 24 hours, which is indicative of an oxidizing environment being maintained over 24 hours. Pharmaceutical compositions of the disclosure can maintain oxidizing Eh values over at least 24 hours in a range of about 400 mV to about 900 mV, about 450 mV to about 800 mV, about 400 mV to about 550 mV. Other suitable values include about 400, 450, 500, 550, 600, 650, 700, 750, 800, 850, 900 mV, and any values there between or ranges defined between these values.

Acidity can be a consequence of hydration of the pharmaceutical compositions (e.g., in part due to synthetic metal sulfide oxidation and the hydrolysis of $Fe^{3+}$ cations, as described above), which can potentially aid in the treatment of wounds that have an alkaline pH (pH 7.5-9), and only heal upon transition to more acidic pH ranges (pH<7). In particular, chronic, non-healing wounds are typically alkaline. Conventional treatment options include attempts to acidify the wound. The acid mantel of healthy skin is pH 4-6. When a wound is alkaline the release of oxygen from hemoglobin cannot occur and the tissue becomes septic and dies. Compositions of the disclosure could be used to effectively buffer the pH of the wound in the range of healthy skin while eliminating pathogens and aiding in the oxygenation of septic tissues. The pharmaceutical compositions of the disclosure can have a pH of 2 to 6. For example, the compositions can have a pH of at least 2, 2.5, 3, 3.5, or 4 and/or up to 3, 3.5, 4, 4.5, 5, 5.5, or 6, such as 2 to 5, 3 to 6, 3 to 5, 4 to 6, or 5 to 6. The pH of the composition can be tuned depending on the application of the composition. For example, when used to treat acne (e.g., in an acid peel treatment), it can be advantageous to have a more acidic pH, such as 2 to 4, similar to an acid skin peel.

Hydration of the pharmaceutical compositions also generates ROS, such as hydrogen peroxide, superoxide anions, hydroperoxyl radicals, and/or hydroxyl radicals. In embodiments, 24 hours after hydration of the pharmaceutical composition, the composition generates at least 7 times more ROS than a composition that does not comprise the synthetic semiconducting metal sulfide. For example, 24 hours after hydration, the compositions of the disclosure can generate at least 7, 8, 9, or 10 times more hydrogen peroxide, hydroxyl radical, hydroperoxyl radicals, or a mixture thereof than the same composition absent the synthetic semiconducting metal sulfide (e.g., a composition containing only the $Fe^{2+}$-exchanged fluorinated synthetic smectite).

Hydration of the pharmaceutical compositions also releases ferrous iron. In embodiments, 24 hours after hydration of the pharmaceutical composition, the composition releases at least 5 times more $Fe^{2+}$ ions than a composition that does not comprise the synthetic semiconducting metal sulfide. For example, 24 hours after hydration, the compositions of the disclosure can release at least 5, 6, 7, or 8 times more $Fe^{2+}$ ions than the same composition absent the synthetic semiconducting metal sulfide (e.g., a composition containing only the $Fe^{2+}$-exchanged fluorinated synthetic smectite).

Advantageously, the pharmaceutical compositions of the disclosure can maintain antibacterial properties without detrimentally affecting (e.g., killing) mammalian cells, such as dermal fibroblasts. In embodiments, after 24 hours of exposure to a mixture comprising at least 25 mg/mL of the composition (e.g., in a suitable media, such as a RPMI media), at least 50% of fibroblast cells are viable. For example, after 24 hours of exposure to the mixture containing at least 25 mg/mL of the composition, at least 50%, 55%, 60%, 65%, 70%, 75%, 80%, 85%, 90%, or 95% of fibroblast cells can be viable. The fibroblast viability can be maintained when the mixture comprises at least 25, 30, 40, 50, 60, 75, 80, 90, or 100 mg/mL.

Applications of the Pharmaceutical Compositions

Also provided herein are applications of the pharmaceutical compositions of the disclosure. The application of mineral poultices may complicate the application of current antibacterial mineral formulations used for wound care, and therefore, applications that limit and control the release of minerals are desirable. Methods of treating an infection can include administering the pharmaceutical compositions to a subject in need thereof. Administration can include oral or topical administration. The infection can be a topical condition or a gastrointestinal condition.

Upon administration, compositions of the disclosure can maintain an Eh (mV) value of about 400 mV to about 900 mV for 24 hours. Without intending to be bound by theory, it is believed that in methods of treating infections, the compositions of the disclosure generate a sustained oxidizing environment which is beneficial for treating the infection and healing, for example, wound healing.

When administered and hydrated, the compositions can, 24 hours after administration, generate at least 7 times more reactive oxygen species (ROS) than a composition that does not comprise the synthetic semiconducting metal sulfide. The ROS generated upon administration either topically or orally can include one or more of hydrogen peroxide, hydroxyl radical, and hydroperoxyl radicals. When administered and hydrated, the composition can, 24 hours after administration, release at least 5 times more $Fe^{2+}$ ion than a composition that does not comprise the synthetic semiconducting metal sulfide.

Methods of treating in accordance with the disclosure can include administering the composition in the presence of fibroblast cells. After 24 hours of exposure at least 25 mg/mL of the composition, at least 50% of fibroblast cells can remain viable.

The compositions of the disclosure can be used in treating topical conditions. For example, in embodiments, the compositions of the disclosure are used to treat bacterial infections, fungal infections, or acne. Examples of topical bacterial infections include, but are not limited to, chronic non-healing wounds, diabetic pressure ulcers, cellulitis, impetigo, boils, leprosy, and necrotizing fasciitis. Examples of topical fungal infections include, but are not limited to, athlete's foot, yeast infections, ringworm, nail fungus, oral thrush, and diaper rash. In embodiments, the compositions are used to treat bacterial infections. In embodiments, the bacterial infection comprises antibiotic resistant bacteria. Contemplated bacterial infections include, but are not limited to, those including ESKAPE pathogens, *Escherichia* coli, extended-spectrum beta lactamase positive (ESBL) *Escherichia coli*, *Salmonella enterica* serotype *typhimurium*, a methicillin-resistant *Staphylococcus aureus* (MRSA), *Staphylococcus epidermidis*, methicillin-resistant *Staphylococcus epidermidis* (MRSE), *Enterococcus* spp., *Klebsiella pneumonia*, *Acinetobacter* spp., *Pseudomonas aeruginosa*, and *Enterobacter* spp. *Propionibacterium acnes*, *Clostridiodies difficile*, *Listeria monocytogenes*, *Pasteurella multocida*, *Proteus vulgaris*, *Bacillus cereus*, and/or *Bordetella bronchiseptica*. In embodiments, the compositions are used to treat fungal infections. In embodiments, the compositions are used to treat acne.

In embodiments, the compositions are used to treat gastrointestinal (GI) bacterial infections. Examples of bacterial GI infections include, but are not limited to, dysentery. Dysentery can be caused, for example, by the consumption of food contaminated with antibiotic resistant *E. coli* (ESBL *E. coli*) and/or by the emergence of *Clostridiodies difficile* as a result of overuse of antibiotics. For example, *C. difficile* infections can occur when a patient is prescribed antibiotics and most or all of the beneficial gut microbiota are killed, leaving only *C. difficile* (an antibiotic resistant bacteria), causing dysentery. In methods of treating GI infections, the composition can be administered, for example, orally. Any suitable oral dosage form can be used, such as pills, tablets, capsules, powders, sachets, liquids and the like.

The disclosure also provides wound dressings comprising the composition of the disclosure suspended in a hydrogel. Examples of suitable hydrogels include, but are not limited to, agarose hydrogels, agar hydrogels, gelatin hydrogels, and polyvinyl alcohol hydrogels. In embodiments, the hydrogel is an agarose hydrogel. In embodiments, the hydrogel is an agar hydrogel. In embodiments, the hydrogel is a gelatin hydrogel. In embodiments, the hydrogel is a polyvinyl alcohol hydrogel. The compositions of the disclosure can be incorporated into 0.5 wt % to 2 wt % hydrogels (e.g., agar, agarose, or gelatin), or into 5 wt % to 35 wt % polyvinyl alcohol hydrogels. In embodiments, the compositions are incorporated into 1 wt % agarose hydrogels (e.g., within the hydrogel matrix). The compositions can be incorporated in the hydrogels in concentrations of at least about 15, 20, 25, 30, 40, 50, 60, 70, 80, or 100 mg/mL and/or up to 40, 50, 60, 75, 80, 90, 100, 200, 300, 400 or 500 mg/mL. In embodiments, the wound dressings comprise 25 mg/mL of the composition suspended in a hydrogel. In embodiments, the wound dressings comprise 100 mg/mL of the composition suspended in a hydrogel. Advantageously, the use of hydrogel formulations for human health applications can provide a wound dressing that can be easily changed while preventing the penetration of the minerals into an open wound.

The disclosure also provides articles of personal protective equipment (PPE) comprising the composition of the disclosure. Also provided are 3D-printed articles comprising the composition of the disclosure. For example, incorporation of these compositions into siloxane resins for 3D printing applications could allow personal protective equipment (PPE) and building materials to be imbued with antibacterial properties. Additionally, fabrics, gauze, HVAC filters and filtration systems, and/or N95 respirators can be impregnated with the compositions of the disclosure to imbue antimicrobial properties. The compositions of the disclosure can be used to decontaminate surfaces, as well as implanted and/or prosthetic medical devices.

Methods of Synthesizing $Fe^{2+}$-Exchanged Fluorinated Smectite

Also provided are methods of synthesizing $Fe^{2+}$-exchanged fluorinated smectite comprising reacting an aqueous solution containing a cation source with fumed silica nanoparticles to provide an aqueous suspension; heating the aqueous suspension at a temperature of 180° C. to 250° C. in the presence of a fluoride source to form a fluorinated synthetic smectite; and admixing the fluorinated synthetic smectite and a ferrous iron source to form the $Fe^{2+}$-exchanged fluorinated synthetic smectite.

In embodiments, the method can include reacting an aqueous solution containing a cation source with fumed silica nanoparticles and a fluoride source to provide an aqueous suspension, heating the aqueous suspension at a temperature of 180° C. to 250° C. to form a fluorinated synthetic smectite; and admixing the fluorinated synthetic smectite and a ferrous iron source to form the $Fe^{2+}$-exchanged fluorinated synthetic smectite.

The method can include in embodiments having a fluoride source present both when reacting the cation source with the fumed silica nanoparticles and during heating of the aqueous suspension.

The divalent cation source is selected based on the desired cations to be incorporate at the octahedral site. For example, the cation can be one or more divalent and trivalent cations. For example, the cation can be $Mg^{2+}$, $Cu^{2+}$, $Zn^{2+}$, $Fe^{3+}$, $Fe^{2+}$ and $Al^{3+}$. The cation source can be provide as a salt of the cation. For example, the cation source can be a chloride salt, such as magnesium (II) chloride, copper (II) chloride, or zinc (II) chloride or iron (II) chloride. Other types of salts are also contemplated herein. For example, if $Mg^{2+}$ is the desired divalent cation, the aqueous solution can comprise magnesium (II) chloride. Similarly, if $Cu^{2+}$, $Zn^{2+}$ or $Fe^{2+}$ is the desired divalent cation, then the aqueous solution can include copper (II) chloride, zinc (II) chloride or iron (II) chloride, respectively. The divalent cation salts can be used with sulfates, nitrates or organic anions in the formula. In embodiments, the aqueous solution comprises magnesium (II) chloride. In embodiments, the aqueous solution comprises copper (II) chloride. In embodiments, the aqueous solution comprises zinc (II) chloride. In embodiments, the aqueous solution comprises iron (II) chloride. The aqueous solution can further include sodium hydroxide. Other hydroxide bases, such as KOH and LiOH are not particularly suitable, as each of KOH and LiOH can exchange in the clay interlayers to collapse the structure of the mineral and/or provide the incorrect stoichiometry to form the mineral.

Fumed silica nanoparticles, also known as pyrogenic silica, includes nanodroplets of amorphous silica fused into branched, chainlike particles. The fumed silica nanoparticles can have a particle size of 300 nm or less, for example 250 nm or less, 200 nm or less, 150 nm or less, or 100 nm or less. In embodiments, the fumed silica nanoparticles have a particle size of 100 nm to 200 nm. The particle sizes, as described throughout the disclosure, can correspond to average sizes or size ranges (e.g., minimum and maximum sizes, for example a d10-d90 range), for example based on a number, weight, area, or volume distribution. The sizes can similarly correspond to an approximate or equivalent diameter (e.g., for a roughly or substantially spherical particle), an approximate or equivalent maximum length (e.g., for a roughly or substantially rod or tubular particle), or an approximate or equivalent maximum width (e.g., for a roughly or substantially plate-like particle). In embodiments, at least 50%, 60%, 70%, 75%, 80%, 90%, 95%, or 99% of the fumed silica nanoparticles have a particle size of 300 nm or less, for example of 100 nm to 200 nm. In embodiments, at least 90% of the fumed silica nanoparticles have a particle size of 100 nm to 200 nm. Advantageously, as compared to other silica sources, fumed silica can prevent the silica from becoming saturated in the aqueous solution, and forms only one mineral. With other silica sources, such as sodium metasilicate, a range of clays and zeolites can form, thereby prohibiting uniform and consistent synthesis of the synthetic smectite.

The aqueous suspension can heated at a temperature of 180° C. to 250° C., for example at a temperature of at least 180, 190, 200, 210, or 220° C. and/or up to 210, 220, 230, 240, or 250° C., such as 180° C. to 220° C., 190° C. to 240° C., 200° C. to 230° C., or 195° C. to 210° C. In embodiments, the aqueous suspension is heated at a temperature of 200° C. for at least 3 days. For example, the aqueous suspension can be heated at a temperature of 200° C. for at least 3, 4, 5, 6, or 7 days. In embodiments, the aqueous suspension is heated for up to 7 days.

The fluoride source can be selected from lithium fluoride (LiF) and sodium fluoride (NaF). In embodiments, the fluoride source is LiF. In embodiments, the fluoride source is NaF. The aqueous suspension can be heated using a hydrothermal reactor. In embodiments, the hydrothermal reactor is lined with polytetrafluoroethylene (PTFE). Heating the aqueous suspension in the presence of a fluoride source provides a fluorinated synthetic smectite. Advantageously, fluoride can greatly increase the crystallization rate of the synthetic smectites. Longer heating times may be used and needed when heating is not done in the presence of the fluoride source.

The fluorinated synthetic smectite is admixed with a ferrous iron source to form the $Fe^{2+}$-exchanged fluorinated synthetic smectite. The admixing of the fluorinated synthetic smectite and ferrous iron source can provide the $Fe^{2+}$-exchanged fluorinated synthetic smectite via cationic exchange. Alternatively, or additionally, the $Fe^{2+}$-exchanged fluorinated synthetic smectite can be formed by admixing the ferrous iron source with a mixture of the fluorinated synthetic smectite and the synthetic semiconducting metal sulfide. That is, the cationic exchange to provide the $Fe^{2+}$-exchanged fluorinated synthetic smectite can occur on the fluorinated synthetic smectite, alone, or on the fluorinated synthetic smectite when present in a mixture with the synthetic semiconducting metal sulfide. The ferrous iron source can be admixed with 10 mg/mL to 100 mg/mL of the mineral(s) (i.e., F-synthetic smectite, alone, or a composition comprising the F-synthetic smectite and synthetic semiconducting metal sulfide), for example 25 mg/mL to 75 mg/mL, or 40 mg/mL to 60 mg/mL. Examples of suitable ferrous iron sources include, but are not limited to iron (II) sulfate hexahydrate, iron (II) chloride, iron (II) chloride anhydrous, and ammonium iron (II) sulfate hexahydrate. In embodiments, the ferrous iron source is selected from the group consisting of iron (II) sulfate hexahydrate, iron (II) chloride, iron (II) chloride anhydrous, ammonium iron (II) sulfate hexahydrate, and any combination thereof. In embodiments, the ferrous iron source is iron (II) sulfate hexahydrate. In embodiments, the ferrous iron source is iron (II) chloride. In embodiments, the ferrous iron source is iron (II) chloride anhydrous. In embodiments, the ferrous iron source is ammonium iron (II) sulfate hexahydrate.

The ferrous iron source can be provided in a concentration of 5 mM to 150 mM. For example, the ferrous iron source can be provided in a concentration of 5, 10, 15, 20, 30, 50, 75, or 100 mM and/or up to 50, 75, 80, 100, 125, 140 or 150 mM, such as 5 mM to 125 mM, 10 mM to 110 mM, 25 mM to 100 mM, 30 mM to 75 mM, or 40 mM to 60 mM. In embodiments, the ferrous iron source is provided in a concentration of 30 mM. Increasing the concentrations of the ferrous iron sources can be correlated with an increased release of $Fe^{2+}$ and $H_2O_2$ from the compositions of the disclosure. In contrast, increased ferrous iron concentrations can decrease the pH of the compositions of the disclosure.

In embodiments, the admixing of the fluorinated synthetic smectite and ferrous iron source is performed a single time. That is, in embodiments, the fluorinated synthetic smectite undergoes a single cationic exchange reaction. The single exchange reaction can include the use of nitrogen purged solutions (e.g., nitrogen purged ferrous iron source, nitrogen purged solvents, etc.). Advantageously, limiting the number of $Fe^{2+}$ exchange reactions and rinsing steps can produce mineral compositions with antibacterial properties and more basic pH values as compared to when multiple exchange reactions and multiple rinsing steps are performed. Furthermore, the single exchange reaction can be performed in ambient atmospheric conditions (with the use of nitrogen purged solutions), and therefore the use of an anaerobic glove box is not required to produce antibacterial mineral formulations that generate extended release of $Fe^{2+}$ and ROS.

In embodiments, the methods further comprise admixing the $Fe^{2+}$-exchanged fluorinated synthetic smectite with the ferrous iron source. That is, in embodiments, the methods can include performing more than one cationic exchange reaction. Up to two, three or four exchange reactions can be performed, with at least one rinsing step performed between each reaction. Multiple exchange reactions can result in lower pH values of the pharmaceutical compositions, which can be beneficial for particular applications where acidic compositions are desired (e.g., acid peel treatments for acne). In order to minimize the amount of oxidation of the ferrous iron throughout the multiple exchange reactions, an anaerobic glove box can be used.

The fluorinated synthetic smectite can be admixed with a sodium source. For example, the fluorinated synthetic smectite can be admixed with a sodium source to form a $Na^+$-exchanged fluorinated synthetic smectite via cationic exchange, prior to admixing with the ferrous iron source. Similar to $Fe^{2+}$-exchanged fluorinated synthetic smectites, pure $Na^+$-exchanged fluorinated synthetic smectite cannot be found in nature, as natural smectites always include a range of cations in the clay interlayers.

Typical smectite synthesis methods require long reaction times (e.g., many times requiring 3-6 months to produce a layered 2:1 clay). Additionally, many secondary minerals (e.g., zeolites) can form during typical synthesis procedures, depending on the silica source, the cation contents, and the pH. Advantageously, the methods of synthesizing the $Fe^{2+}$-exchanged fluorinated synthetic smectites of the disclosure can rapidly produce scalable quantities of pure synthetic smectite clays in as few as 3, 4, or 5 days. This rapid, consistent, and reproducible synthesis can be achieved, for example, using hydrothermal pressure reactors and fumed silica nanoparticles.

Methods of Making Synthetic Semiconducting Metal Sulfide

Further provided herein are methods of making synthetic semiconducting metal sulfide can include heating a polysulfide and a solution comprising a metal or metal source and a water-soluble polymer.

For example a method of making a synthetic metal sulfide can include comprising heating a polysulfide and a solution comprising a ferrous iron and a water-soluble polymer at a temperature of 25° C. to 250° C. to form the synthetic metal sulfide.

In embodiments, the polysulfide comprises a solution comprising elemental sulfur ($S^0$) and sodium sulfide (e.g., Na$_2$S·9H$_2$O). Other sulfur sources can also be used in the solution, such as, but not limited to, thiourea, thioacetamide, cysteine, thioglycolic acid. The sulfur sources in the solution can be any combination of thiourea, thioacetamide, cysteine, thioglycolic acid, sodium sulfide and elemental S. Advantageously, using polysulfides in the methods of the disclosure can lead to a more complete reaction, resulting in synthetic semiconducting metal sulfide having improved uniformity in shape and size as compared to when only elemental sulfur is used (FIGS. 5A-5D).

Examples of suitable water-soluble polymers can include, but are not limited to, polyvinylpyrrolidone (PVP), polyvinyl alcohol (PVA), polyethylene glycol (PEG), and carboxymethylcellulose (CMC). In embodiments, the water-soluble polymer is selected from the group consisting of polyvinylpyrrolidone (PVP), polyvinyl alcohol (PVA), polyethylene glycol (PEG), carboxymethylcellulose (CMC), and a combination thereof. The water-soluble polymer can provide a template for mineral nucleation that can be removed with washing once the reaction is complete. The concentration of the polymer can be adjusted to control synthetic semiconducting metal sulfide particle size and/or morphology. In embodiments, the water-soluble polymer is PVP. In embodiments, the water-soluble polymer is PVA. In embodiments, the water-soluble polymer is PEG. In embodiments, the water-soluble polymer is CMC.

The metal and/or the metal source can include Ag, Cu, Fe, Zn and combinations thereof. The method can include providing two or more metals or metal ion precursors. The metal ion precursor can be provided in the form of a chloride, sulfate or combinations thereof.

For example, the ferrous iron can be provided in the form of iron (II) chloride, iron (II) sulfate hexahydrate, iron (II) chloride anhydrous, ammonium iron(II) sulfate hexahydrate, or a combination thereof. In embodiments, the ferrous iron is provided in the form of iron (II) chloride anhydrous.

The methods can further comprise admixing the polysulfide and the solution (i.e., comprising metal and the water-soluble polymer) at a temperature of at least 70° C. prior to heating. For example, the polysulfide and the solution can be admixed at a temperature of at least 70, 75, 80, or 90° C. and/or up to 80, 85, 90, 95 or 100° C. prior to heating, such as 70° C. to 100° C., 75° C. to 90° C., or 80° C. to 85° C. In embodiments, the polysulfide and the solution are admixed at a temperature of 75° C. prior to the hydrothermal reaction at 200° C.

The polysulfide and the solution can be heated at a temperature of 25° C. to 250° C., for example at a temperature of at least 25, 50, 75, 100, 110, 120, 130, 140, 150, 160, 170, 180, 190, 200, 210, or 220° C. and/or up to 100, 120, 150, 175, 180, 210, 220, 230, 240, or 250° C., such as 25° C. to 250° C., 180° C. to 220° C., 190° C. to 240° C., 200° C. to 230° C., or 195° C. to 210° C. In embodiments, the polysulfide and the solution are heated for at least 36 hours. For example, the aqueous suspension can be heated at a temperature of 200° C. for at least 36 or 48 hours. In embodiments, the aqueous suspension is heated for 48 hours. The polysulfide and the solution can be heated using a hydrothermal reactor. In embodiments, the hydrothermal reactor is lined with polytetrafluoroethylene (PTFE).

In embodiments, the methods further comprise washing the synthetic semiconducting metal sulfide with a rinsing solvent. The synthetic semiconducting metal sulfide can be washed to remove any water-soluble polymer(s), residual sulfur, and any Fe-oxide impurities. The rinsing solvent can be selected from the group consisting of water, hydrochloric acid, xylene, dichloromethane, ethanol, and any combination thereof. In embodiments, the rinsing solvent comprises water (e.g., at least one, or at least two water washes). In embodiments, the rinsing solvent comprises hydrochloric acid (e.g., at least one or at least two 1M HCl washes). In embodiments, the rinsing solvent comprises xylene (e.g., at least one, or at least two xylene washes). In embodiments, the rinsing solvent comprises dichloromethane (e.g., at least one, or at least two DCM washes). In embodiments, the rinsing solvent comprises ethanol (e.g., at least one, at least two, or at least three ethanol washes). In embodiments, the washing step includes washing at least once with each of water, hydrochloric acid, xylene, dichloromethane, and ethanol, with at least one centrifugation performed between each wash. In embodiments, the methods further comprise drying the washed synthetic semiconducting metal sulfide. The washed synthetic semiconducting metal sulfide can be dried using a heating block at a temperature of 50° C. to 70° C., for example 55° C. to 65° C. or 50° C. to 60° C. The drying can occur under nitrogen purge. Drying of the washed synthetic semiconducting metal sulfide can ensure removal of solvents from the synthetic semiconducting metal sulfide sample.

Figure 5A:
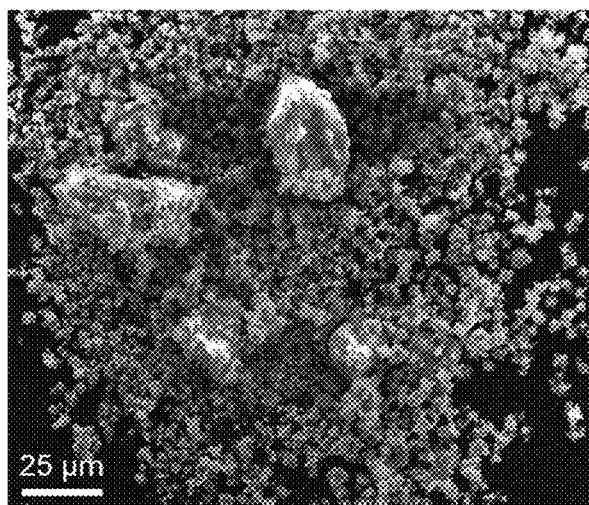
FIG. 5A is a scanning electron microscopy (SEM) image of a synthetic pyrite prepared using only $S^0$ as the sulfur source, showing 10 to 45 μm particles of unreacted $S^0$.
Figure 5B:
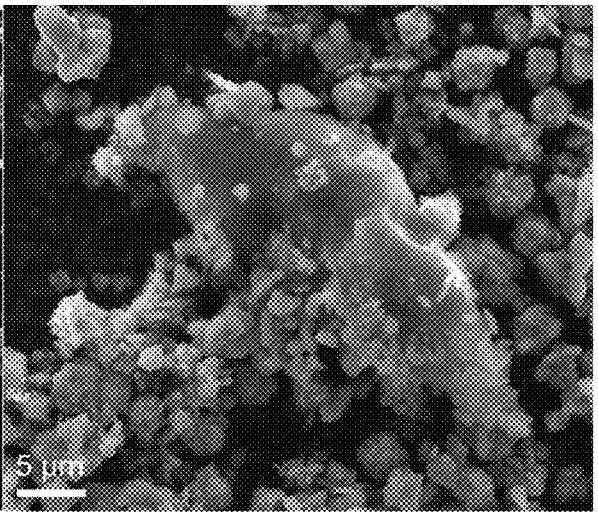
FIG. 5B is an SEM image of a synthetic pyrite prepared using only $S^0$ as the sulfur source, showing 10 to 25 μm particle of unreacted $S^0$ with associated synthetic Fe-sulfide particles.
Figure 5C:
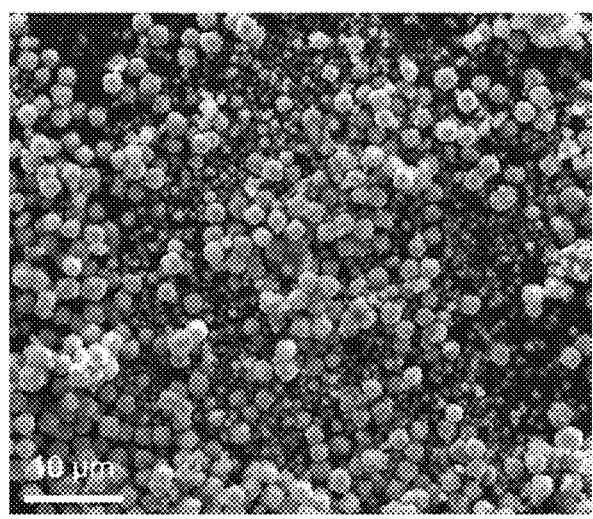
FIG. 5C is an SEM image of a synthetic Fe-sulfide prepared using a polysulfide as the sulfur source, after solvent washes to remove minor $S^0$ impurities.
Figure 5D:
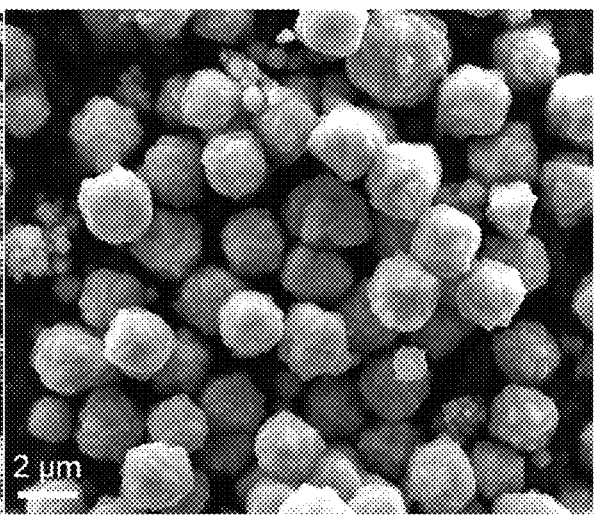
FIG. 5D is an SEM image of a synthetic pyrite prepared using a polysulfide as the sulfur source, after solvent washes to remove minor $S^0$ impurities, showing a 1-2 μm particle size range and spherical morphology.

In embodiments, the synthetic semiconducting metal sulfide, prepared according to the methods of the disclosure, is in a form of microspheres. For example, as shown in FIG. 5C and FIG. 5D, the synthetic semiconducting metal sulfide can be in the form of microspheres having a particle size of at least 1 μm, for example from 1 μm to 2 μm, as described herein. FIG. 5C and FIG. 5D show synthetic pyrite in the form of microspheres. Advantageously, the synthetic semiconducting metal sulfide of the disclosure has a controllable size and shape, and can be free of toxic elements, such as arsenic, lead, cobalt, nickel, mercury, and/or uranium.

EMBODIMENTS

Specifically contemplated embodiments of the disclosure are herein described in the following numbered paragraphs. These embodiments are intended to be illustrative in nature ant not intended to be limiting.

A pharmaceutical composition comprising Fe$^{2+}$-exchanged fluorinated synthetic smectite and synthetic semiconducting metal sulfide.

A pharmaceutical composition comprising Fe$^{2+}$-exchanged fluorinated hectorite as the synthetic smectite and synthetic pyrite as the synthetic semiconducting metal sulfide.

The composition of paragraph [0155] or [0156], wherein the Fe$^{2+}$-exchanged fluorinated synthetic smectite is present in an amount of 80 wt % to 98.5 wt %, based on the total weight of the composition.

The composition of paragraph [0157], wherein the Fe$^{2+}$-exchanged fluorinated synthetic smectite is present in an amount of 90 wt % to 98.5 wt %, based on the total weight of the composition.

The composition of any one of paragraphs [0155]-[0158], wherein the synthetic semiconducting metal sulfide is present in an amount of 1.5 wt % to 20 wt %, based on the total weight of the composition.

The composition of paragraph [0159], wherein the synthetic semiconducting metal sulfide is present in an amount of 5 wt % to 20 wt %, based on the total weight of the composition.

The composition of any one of paragraphs [0155]-[0160], having a pH of 2 to 6.

The composition of any one of paragraphs [0155]-[0161], wherein the Fe$^{2+}$-exchanged fluorinated synthetic smectite has a particle size of less than 2 μm.

The composition of paragraph [0162], wherein the Fe$^{2+}$-exchanged fluorinated synthetic smectite has a particle size of 0.5 μm to 1 μm.

The composition of any one of paragraphs [0155]-[0014], wherein the Fe$^{2+}$-exchanged fluorinated synthetic smectite has an average cation exchange capacity of 50 to 150 meq per 100 g.

The composition of any one of paragraphs [0155]-[0164], wherein the Fe$^{2+}$-exchanged fluorinated synthetic smectite, at an octahedral site, comprises Li$^+$.

The composition of any one of paragraphs [0155]-[0165], wherein the Fe$^{2+}$-exchanged fluorinated synthetic smectite, at an octahedral site, comprises Mg$^{2+}$, Cu$^{2+}$, Zn$^{2+}$, or Fe$^{2+}$.

The composition of paragraph [0166], wherein the Fe$^{2+}$-exchanged fluorinated synthetic smectite, at an octahedral site, comprises Mg$^{2+}$.

The composition of any one of paragraphs [0155]-[0167], wherein the Fe$^{2+}$-exchanged fluorinated synthetic smectite comprises from 5 meq to 100 meq of ferrous iron (Fe$^{2+}$), per 100 g of the Fe$^{2+}$-exchanged fluorinated synthetic smectite.

The composition of any one of paragraphs [0155]-[0168], wherein the synthetic semiconducting metal sulfide has a particle size of at least 1 μm.

The composition of paragraph [0169], wherein the synthetic semiconducting metal sulfide has a particle size of 1 μm to 2 μm.

The composition of any one of paragraphs [0155]-[0170], free of arsenic, lead, cobalt, nickel, mercury, or uranium.

The composition of any one of paragraphs [0155]-[0171], wherein the composition is bacteriostatic.

The composition of any one of paragraphs [0155]-[0172], wherein the composition is bactericidal.

The composition of any one of paragraphs [0155]-[0173], wherein, 24 hours after hydration, the composition generates at least 7 times more reactive oxygen species (ROS) than a composition that does not comprise the synthetic semiconducting metal sulfide.

The composition of paragraph [0174], wherein the ROS comprises hydrogen peroxide, hydroxyl radical, hydroperoxyl radicals, or a mixture thereof.

The composition of any one of paragraphs [0155]-[0175], wherein, 24 hours after hydration, the composition releases at least 5 times more Fe$^{2+}$ ion than a composition that does not comprise the synthetic semiconducting metal sulfide.

The composition of any one of paragraphs [0155]-[0176], wherein, after 24 hours of exposure to a mixture comprising at least 25 mg/mL of the composition, at least 50% of fibroblast cells are viable.

The composition of any one of paragraphs [0155]-[0177], for use in treating a topical condition or a gastrointestinal infection.

The composition of paragraph [0178], wherein the topical condition is selected from the group consisting of a bacterial infection, a fungal infection, and acne.

The composition of paragraph [0179], wherein the bacterial infection comprises antibiotic resistant bacteria.

The composition of paragraph [0180], wherein the antibiotic resistant bacteria is selected from the group consisting of *Enterococcus* spp., *Staphylococcus aureus, Klebsiella pneumonia, Acinetobacter* spp., *Pseudomonas aeruginosa, Enterobacter* spp., *Escherichia coli*, extended-spectrum beta lactamase positive (ESBL) *Escherichia coli, Salmonella enterica* serotype *typhimurium*, a methicillin-resistant *Staphylococcus aureus* (MRSA), *Staphylococcus epidermidis*, methicillin-resistant *Staphylococcus epidermidis* (MRSE), *Propionibacterium acnes, Clostridiodies difficile, Listeria monocytogenes, Pasteurella multocida, Proteus vulgaris, Bacillus cereus, Bordetella bronchiseptica*, and any combination thereof.

The composition of paragraph [0180], wherein the gastrointestinal infection is dysentery.

The composition of any one of paragraphs [0155] [0182] wherein the composition is adapted to maintain an Eh value of about 400 mV to about 900 mV for at least 24 hours.

A wound dressing comprising the composition of any one of paragraphs [0155]-[0182][0182] suspended in a hydrogel.

An article of personal protective equipment comprising the composition of any one of paragraphs [0155]-[0182].

A 3D-printed article comprising the composition of any one of paragraphs [0155]-[0182] and a siloxane resin.

A method of synthesizing Fe$^{2+}$-exchanged fluorinated synthetic smectite comprising:
  reacting an aqueous solution comprising one or more cation sources with fumed silica nanoparticles to provide an aqueous suspension;
  heating the aqueous suspension at a temperature of 180° C. to 250° C. in the presence of a fluoride source to form fluorinated synthetic smectite; and
  admixing the fluorinated synthetic smectite and a ferrous iron source to form the Fe$^{2+}$-exchanged fluorinated synthetic smectite.

A method of synthesizing Fe$^{2+}$-exchanged fluorinated synthetic smectite comprising:
  reacting an aqueous solution comprising one or more cation sources with fumed silica nanoparticles and a fluoride source to provide an aqueous suspension;
  heating the aqueous suspension at a temperature of 180° C. to 250° C. optionally in the presence of a fluoride source to form fluorinated synthetic smectite; and
  admixing the fluorinated synthetic smectite and a ferrous iron source to form the Fe$^{2+}$-exchanged fluorinated synthetic smectite.

The method of paragraph [0187], wherein the aqueous solution further comprises sodium hydroxide.

The method of paragraph [0187] to [0189], wherein the fumed silica nanoparticles have a particle size of 300 nm or less.

The method of paragraph [0190], wherein the fumed silica nanoparticles have a particle size of 100 nm to 200 nm.

The method of any one of paragraphs [0187]-[0191], wherein the fluoride source is selected from lithium fluoride (LiF) or sodium fluoride (NaF).

The method of any one of paragraphs [0187]-[0192], wherein the aqueous suspension is heated in a hydrothermal reactor.

The method of paragraph [0193], wherein the hydrothermal reactor is lined with polytetrafluoroethylene (PTFE).

The method of any one of paragraphs [0187]-[0194], wherein the aqueous suspension is heated at a temperature of 200° C. for at least 3 days.

The method of any one of paragraphs [0187]-[0195], wherein the aqueous suspension is heated for up to 7 days.

The method of any one of paragraphs [0187]-[0196], wherein the ferrous iron source is selected from the group consisting of iron(II) sulfate hexahydrate, iron(II) chloride, iron(II) chloride anhydrous, ammonium iron(II) sulfate hexahydrate, and any combination thereof.

The method of any one of paragraphs [0187]-[0197], wherein the ferrous iron source has a concentration of 5 mM to 150 mM.

The method of any one of paragraphs [0187]-[0198], wherein the admixing of the fluorinated synthetic smectite and ferrous iron source is performed a single time.

The method of any one of paragraphs [0187]-[0198], further comprising admixing the synthetic fluorinated synthetic smectite with the ferrous iron source.

The method of any one of paragraphs [0187]-[0200], further comprising admixing the fluorinated synthetic smectite with a sodium source.

The method of paragraph [0201], wherein the sodium source is sodium chloride.

The method of any one of paragraphs [0187]-[0202], wherein the $Fe^{2+}$-exchanged fluorinated synthetic smectite has a particle size of less than 1 μm.

The method of any one of paragraphs [0187]-[0203], wherein the $Fe^{2+}$-exchanged fluorinated smectite has an average surface area of 500 $m^2/g$ to 700 $m^2/g$.

A method of making synthetic semiconducting metal sulfide comprising heating a polysulfide and a solution comprising a metal source and a water-soluble polymer at a temperature of 180° C. to 250° C. to form the synthetic semiconducting metal sulfide.

The method of paragraph [0205], wherein the polysulfide comprises a solution comprising elemental sulfur and sodium sulfide.

The method of paragraph [0205] or [0206], wherein the water-soluble polymer is selected from the group consisting of polyvinylpyrrolidone (PVP), polyvinyl alcohol (PVA), polyethylene glycol (PEG), carboxymethyl cellulose (CMC), and any combination thereof.

The method of any one of paragraphs [0205]-[0207], wherein the metal source comprises ferrous iron provided by iron (II) chloride, iron (II) sulfate hexahydrate, iron (II) chloride, iron (II) chloride anhydrous, ammonium iron(II) sulfate hexahydrate, or a combination thereof.

The method of any one of paragraphs [0205]-[0208], further comprising admixing the polysulfide and the solution at a temperature of at least 70° C. prior to heating.

The method of any one of paragraphs [0205]-[0209], wherein the heating is performed in a hydrothermal reactor.

The method of paragraph [0210], wherein the hydrothermal reactor is lined with polytetrafluoroethylene (PTFE).

The method of any one of paragraphs [0205]-[0211], wherein the heating is performed for at least 36 hours.

The method of any one of paragraphs [0205]-[0212], further comprising washing the synthetic semiconducting metal sulfide with a rinsing solvent, the rinsing solvent selected from the group consisting of water, hydrochloric acid, xylene, dichloromethane, ethanol, and any combination thereof.

The method of any one of paragraphs [0205]-[0213] wherein the synthetic semiconducting metal sulfide is in a form of microspheres.

The method of any one of paragraphs [0205]-[0214], wherein the synthetic semiconducting metal sulfide has a particle size of at least 1 μm.

The method of paragraph [0215], wherein the particle size is 1 μm to 2 μm.

EXAMPLES

Example 1—Synthesis and Analysis of Fluorinated Hectorite

Synthesis of Fluorinated Hectorite (F-Hectorite)

Fluorinated hectorites were prepared according to the following procedures. A brucite ($Mg(OH)_2$) solution was prepared by dissolving 5 g of $MgCl_2$ in 200 mL of DI water, followed by the addition of 1M NaOH (50 mL). The solution was stirred for 5 minutes, transferred into a centrifuge tube and spun at 3500 rpm for 10 minutes. The supernatant was decanted and 3 g of fumed $SiO_2$ (100-200 nm particle size) was added, followed by 0.4 g LiF or LiCl. The suspension was then transferred from the centrifuge tube to a beaker and diluted to 300 mL, achieving a 3% solid to solution ratio. The suspension was stirred at 300 rpm for 30 minutes. The homogenized solution was transferred into a 400 mL polytetrafluoroethylene (PTFE) lined hydrothermal reactor and heated at 200° C. for 5 days. After 5 days, the clays were cooled to room temperature and 150 mL was transferred to centrifuge tubes (250 mL volume) followed by the addition of 2 M NaCl to flocculate and exchange all the hectorite surfaces with $Na^+$ cations. Clays were centrifuged at 3500 rpm for 10 minutes, resuspended with 2 M NaCl (200 mL) and allowed to equilibrate for 30 minutes. The clays were pelleted by centrifugation and then transferred to dialysis tubing with a 5-8 K Dalton molecular weight cutoff. Excess salts were removed by placing the dialysis tubes in a constant flow DI water bath for 3 days. The removal of NaCl was verified by $AgNO_3$ precipitation. The dialyzed clays were transferred to a PTFE beaker and dried at 65° C., rehydrated with 50 mL DI water, and freeze-dried for further use.

Figure 2:
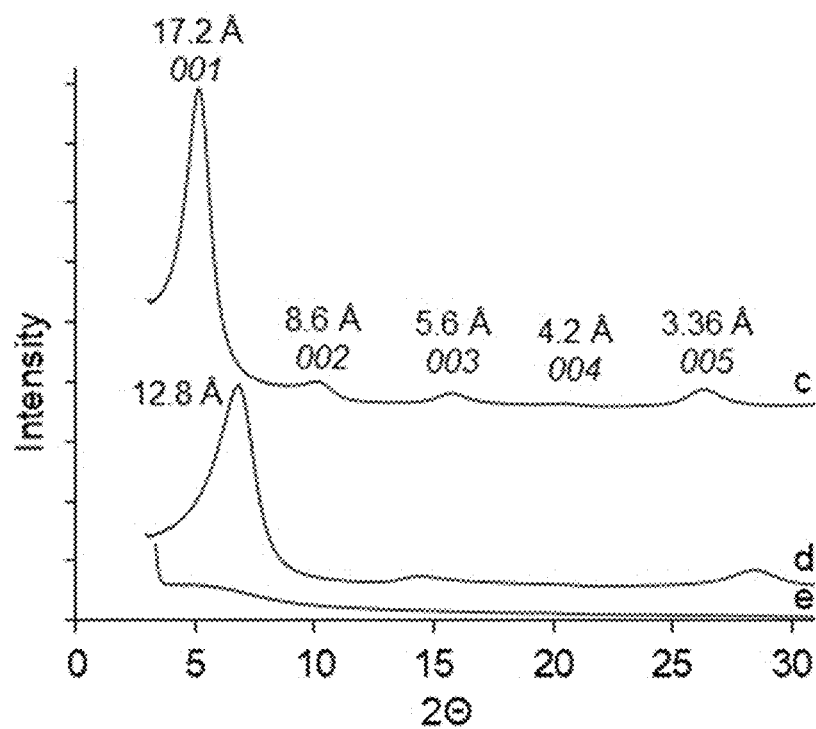
FIG. 2 is an oriented XRD pattern of (c) an ethylene glycol (EG) saturated synthetic fluorinated hectorite prepared according to the disclosure, (d) an air-dried synthetic fluorinated hectorite prepared according to the disclosure, and (e) the lack of hectorite formation in the absence of fluoride.

X-ray diffraction patterns of the synthesized hectorite were obtained and indicated that pure hectorite was formed (FIG. 1, pattern a). When samples were reacted at 180° C. for 3 days, a portion of the fumed silica nanoparticles remained (FIG. 1, pattern b). Fluoride greatly increased the crystallization rate of the hectorites, and samples reacted without fluoride only showed weak 001 (hkl) peaks after reacting for 5 days at 200° C. The basal spacing of the F-hectorite interlayer spaces was 12.8 Å, which was common for smectite clay minerals (FIG. 2, pattern d). Upon saturation with ethylene glycol (EG), the interlayer space expanded to 17.2 Å, and hkl reflections, characteristic of smectite clays, appeared (FIG. 2, pattern c). The random powder mounts showed a peak at 1.52 Å, which was characteristic of trioctahedral smectites.

Fourier Transform Infrared Spectroscopy (FTIR) of Synthetic F-Hectorite Clays

All hectorite samples were dried at 110° C. for 18 hours before FTIR spectra were collected to limit the contribution of vH-O—H stretching bands from water around 3400 $cm^{-1}$ and 1630 $cm^{-1}$. FTIR spectra were collected using spectrometer equipped with a 1 bounce diamond attenuated total reflectance (ATR) cell with a spectral resolution of 2 $cm^{-1}$ from 4000 to 400 $cm^{-1}$. Before each sample was analyzed, the ATR cell was cleaned with ethanol, allowed to dry, and 256 background scans were run. The samples were immediately transferred onto the ATR cell and 128 scans were collected.

The FTIR spectra of the synthetic F-hectorite clays were indicative of natural hectorite clay minerals, having trioctahedral site occupancy with $Li^+$ and $Mg^{2+}$ occupying all potential octahedral sites. The FTIR spectra showed octahedral stretching from Mg and Li in the octahedral sheets at 3616 $cm^{-1}$ and 3687 $cm^{-1}$. Stretching and deformation bands from tetrahedral Si—O bonds were present at 955, 778, 700, and 412 $cm^{-1}$. The amorphous fumed silica nanoparticles used in the synthesis reaction had Si—O stretching and deformation bands at 1190, 1067, and 800 $cm^{-1}$. The fumed silica nanoparticles used in the reaction did not contain Si—OH bonds (3700 $cm^{-1}$) that were measurable with FTIR.

Combination Gaussian-Lorentzian curve deconvolution of FTIR bands at 1190 and 1067 cm$^{-1}$ was used to determine the percentage of unreacted fumed silica remaining in the synthetic hectorites under different reaction conditions. Samples reacted at 180° C. for 3 days had 24% unreacted fumed silica nanoparticles present. After reacting for 5 days at 200° C., the samples contained only 6% unreacted fumed silica nanoparticles.

Table 1, below, provides the FTIR band assignments for the synthetic F-hectorite clays.

TABLE 1

FTIR Band Assignments for F-hectorite clays

| Wavenumber (cm$^{-1}$) | Band Assignment | Description |
|---|---|---|
| 3687 | ν(Mg$_3$—OH) | Octahedral νOH-stretching |
| 3616 | ν(Mg$_2$Li—OH) | Octahedral νOH-stretching |
| 3400 | ν(H—O—H) | Adsorbed water νOH-stretching |
| 1626 | δ(H—O—H) | Adsorbed water δOH-deformation |
| 955 | ν(Si—O) | Tetrahedral νSiO-stretching |
| 778 | δ(Si—O) | Tetrahedral δSi—O deformation |
| 700 | δ(Si—O) | Tetrahedral δSi—O deformation |
| 642 | δ(Mg$_3$—OH) | Octahedral δOH-deformation |
| 412 | δ(Si—O) | Tetrahedral δSi—O deformation |

Cation Exchange Capacity of F-Hectorite

Cation exchange capacity (CEC) is a standard measure of the quantity of exchangeable cations that a mineral can adsorb. CEC measurements of the F-hectorites were determined using cobaltichexamine chloride (Co(III)-hexamine) absorbance at 470 nm as previously described. Samples were dried at 120° C. overnight prior to measurements, then 0.2-3 g portions were mixed with 5 mL of a 30 mM Co(III)-hexamine solution. Samples where then sonicated for 2 minutes, shaken for 1 hour and centrifuged at 5000 rpm for 30 minutes.

Figure 3:
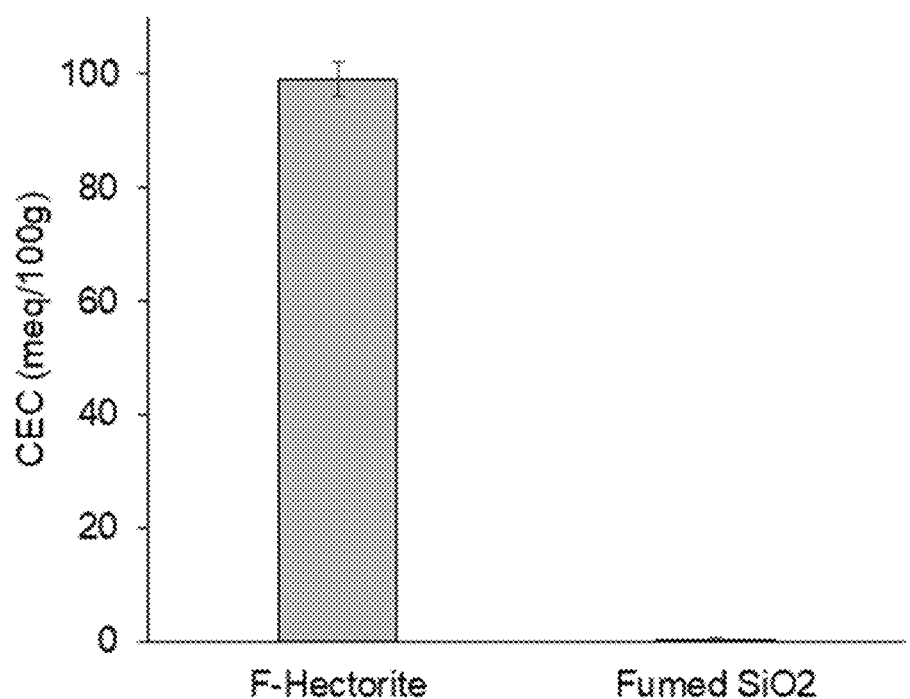
FIG. 3 is a graph of the cation exchange capacity (CEC) of a synthetic fluorinated hectorite of the disclosure and fumed silica nanoparticles used in the synthesis reaction.

The synthetic F-hectorites reacted at 200° C. for 5 days had a CEC of 99 meq/100 g of sample, as shown in FIG. 3. Natural smectite clay minerals typically have CEC values ranging from 60 to 120 meq/100 g. The fumed silica nanoparticles used in the synthesis reaction had almost no cation exchange capacity, with a value of 0.3 meq/100 g.

Example 2—Synthesis and Analysis of Pyrite

Pyrite microspheres where synthesized according to the following procedures. A polysulfide solution was prepared by dissolving 5 g of Na$_2$S·9H$_2$O in 10 mL DI water, followed by the addition of 5 g elemental sulfur (S$^0$) and heating at 75° C. A separate beaker with 5 g FeCl$_2$ and 5 g polyvinylpyrrolidone (PVP) dissolved in 100 mL Di water was stirred for 5 minutes at 300 rpm and heated to 75° C. The Fe$^{2+}$-PVP solution was slowly added to the polysulfide solution and stirred at 300 rpm at 75° C. for 1 minute. The solution was transferred into a 200 mL PTFE-lined hydrothermal reactor and heated to 200° C. for 48 hours. After the reaction was complete, the reactor was cooled to room temperature and the Fe-sulfides were transferred into centrifuge tubes. The samples were centrifuged at 5000 rpm for 5 minutes and rinsed with DI water, 1 M HCl (2×), xylene (2×), dichloromethane (2×), and ethanol (2×), with centrifugation between each rinsing step.

Synthesis using only S$^0$ as the sulfur source was carried out by mixing 5 g of S$^0$ with 5 g FeCl$_2$ and 5 g PVP in 110 mL DI water. The suspension was then transferred into a PTFE-lined hydrothermal reactor and heated at 200° C. for 48 hours. After 48 hours, the samples were centrifuged and rinsed in DI water and 1 M HCl (2×), as described above.

Figure 4:
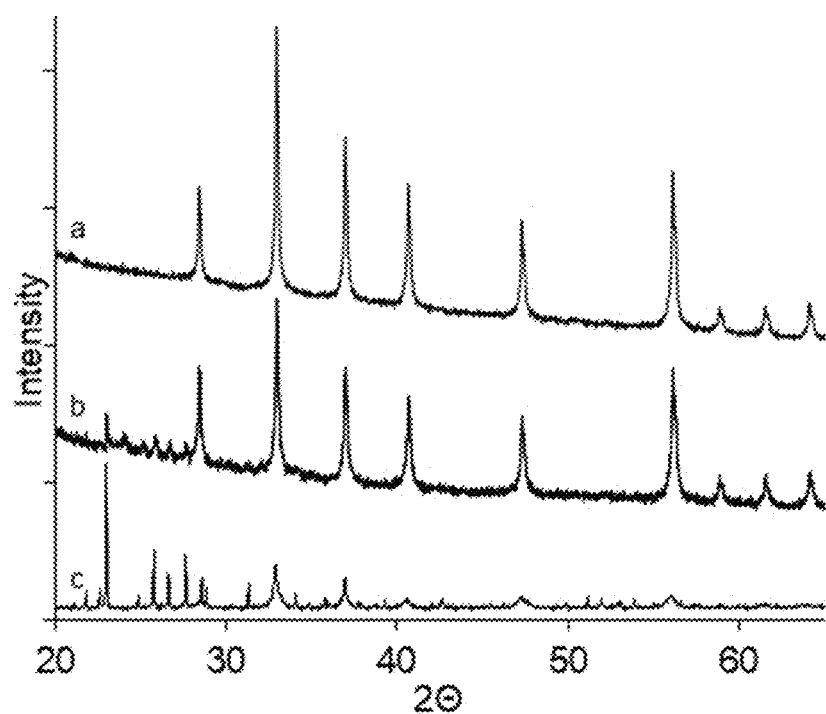
FIG. 4 is an XRD pattern of synthetic pyrite prepared according to the disclosure (a) after removal of elemental sulfur ($S^0$) impurities, (b) before removal of $S^0$ impurities; and (c) when only $S^0$ (no polysulfide) was used as the sulfur source.

The synthesis reactions using only S$^0$ as the sulfur source formed pyrite, however the reaction was incomplete and the weight % quantities of S$^0$ remained in the final product, as shown in FIG. 4 (pattern c). Moreover, as shown in FIGS. 5A and 5B, the pyrite formed using S$^0$ as the only sulfur source did not have uniform sizes or shapes.

In contrast, when polysulfides were used in the pyrite synthesis reaction, only minor S$^0$ impurities were observed in the XRD pattern (FIG. 4, pattern b). Rinses with xylene effectively removed these impurities and produced pure pyrite powders (FIG. 4, pattern a). The SEM images of the purified pyrite samples indicated that 1-2 μm spheres formed (FIGS. 5C & 5D). Thus, the particle sizes of the synthetic pyrite were controlled and consistent, as opposed to natural pyrite which can have particle sizes ranging from 1-100 μm in a single sample.

Example 3—Evaluation of Compositions Containing F-Hectorite and Pyrite

Initial antibacterial susceptibility tests were performed on mixtures of F-hectorite and pyrite, as prepared according to Examples 1 and 2. Mixtures of F-hectorite with 5 and 10 wt % pyrite were prepared in a mortar and pestle, transferred into 15 mL centrifuge tubes, and autoclaved at 120° C. for 30 minutes prior to antibacterial susceptibility testing. These percentages of pyrite were similar to those observed in natural antibacterial samples. Determination of bacterial growth inhibition (bacteriostatic) vs. bactericidal activity (100% cell death) of samples was achieved by spot plating serial dilutions of clay suspensions and cells. Colony forming units (CFU/mL) were determined for *E. coli* ATCC 25922 and *S. epidermidis* ATCC 14990 using methods modified from those known in the art. Cultures were grown to log-phase and diluted to ~10$^8$ CFU/mL in 30 g/L tryptic soy broth (TSB). After autoclaving and cooling to room temperature, the antibacterial mineral mixtures were resuspended in isotonic NaCl (0.85%) and sonicated for 1 minute to resuspend the minerals. The compositions and bacteria were reacted in a 1:1 ratio reaching a final culture volume of 2.5 mL. Samples were incubated in a 12-well plate for 24 hours on a plate shaker at 200 rpm and 37° C. Serial dilutions of the samples (10$^0$-10$^{-7}$) were spot plated (8 μL) onto TSB agar plates (30 g/L) in triplicate using a multipipette and incubated at 37° C. for 24 hours. Growth inhibition values were defined by a 10$^3$ CFU/mL reduction in cells. Samples were considered bactericidal only if they killed 100% of the cells in the undiluted sample.

The quantification of Fe$^{2+}$ from mineral suspension supernatant solutions was achieved by using 1,10-phenanthroline. The photochemical reduction of the Fe$^{3+}$-phenanthroline complex can artificially produce Fe$^{2+}$ during analysis. To prevent this, all Fe$^{2+}$ measurements were performed under red photographic light bulbs. A 200 μL aliquot of mineral suspension was transferred into a microcentrifuge tube and spun at 13,000 rpm for 10 minutes. For the measurement of Fe$^{2+}$, a 10-50 μL aliquot of supernatant was added to 50 μL of 1 wt % 1,10-phenanthroline (dissolved in 95% ethanol). The solutions were then diluted to a final volume of 600 μL using 1 wt % Na-citrate. The red Fe$^{2+}$-phenanthroline complex was allowed to develop in the dark for 10 minutes and absorbance was measured with a UV-Vis spectrophotometer at 510 nm. Standard curves were generated using ferrous sulfate heptahydrate stock solutions with concentrations ranging from 1 to 4000 μM iron.

Concentrations of hydrogen peroxide were quantified as follows. A buffer solution of 1 M $KH_2PO_4$ and 50 mM EDTA was prepared and adjusted to pH 4.2. A 5 mM leuco crystal violet stock solution was prepared in 0.1 M HCl. Stock solutions of horseradish peroxidase (HRP) type II were prepared in sterile DI water at a concentration of 14.4 enzyme units/mL. Aliquots (200 µL) of the bacterial-mineral suspensions were transferred into microcentrifuge tubes and centrifuged at 13,000 rpm for 10 minutes. Then, a 10 to 50 µL aliquot of the supernatant was transferred into a microcentrifuge tube containing buffer solution, achieving a final volume of 1200 µL. Next, 50 µL of the leuco crystal violet reagent was added, followed by 50 µL of the HRP enzyme. The samples were reacted in the dark at room temperature for 15 minutes. Absorbance was measured at 590 nm using a spectrophotometer and calibration curves were generated using hydrogen peroxide at 5 to 400 µM concentrations.

Figure 6A:
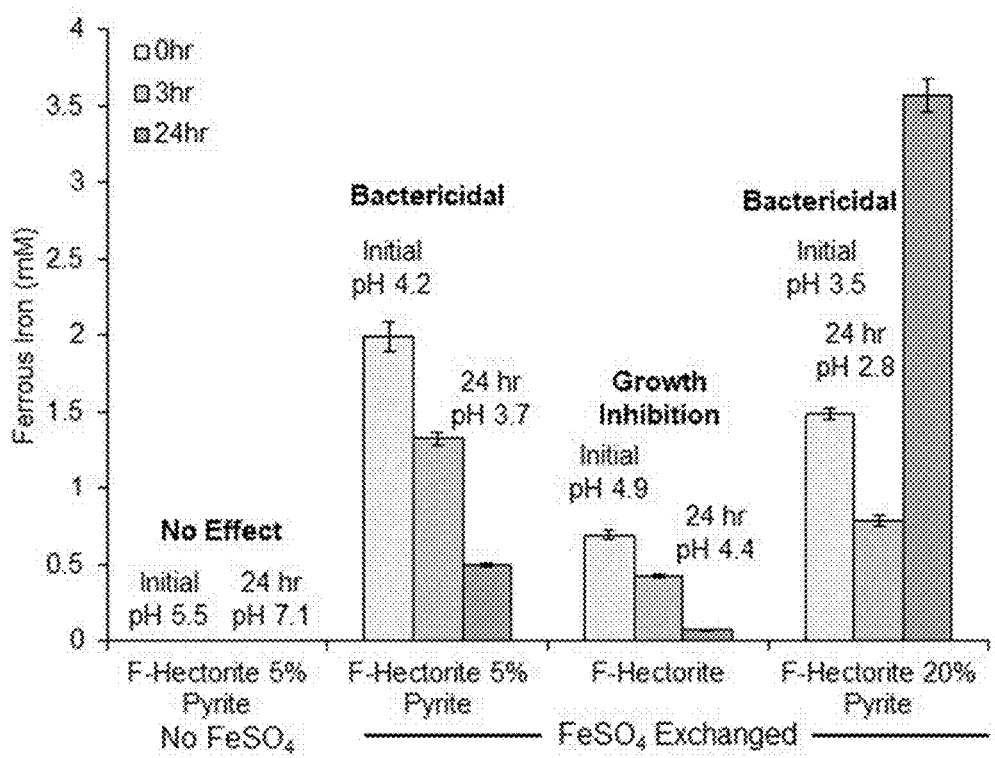
FIG. 6A is a graph of the ferrous iron release, pH, and antibacterial activity of pharmaceutical compositions of antibacterial minerals prepared in accordance with the disclosure.
Figure 6B:
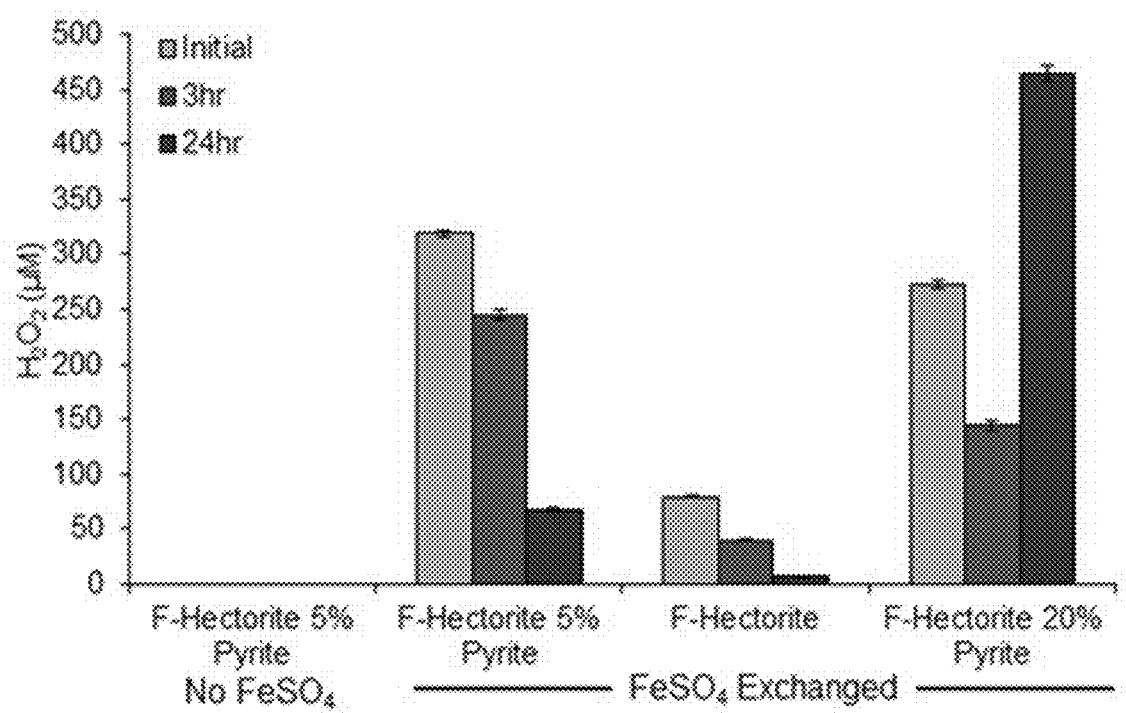
FIG. 6B is a graph of the hydrogen peroxide generation of pharmaceutical compositions prepared in accordance with the disclosure.
Figure 7:
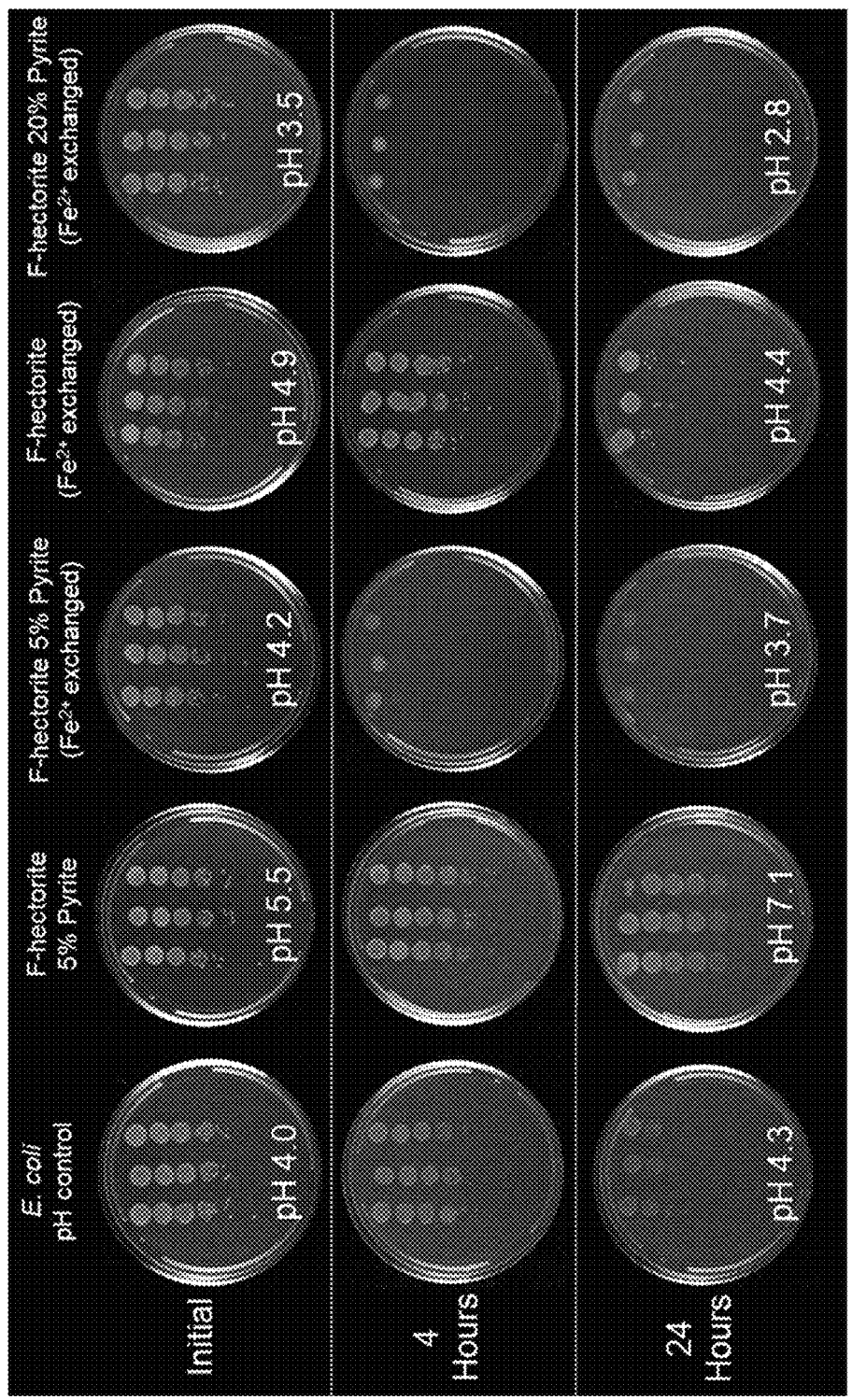
FIG. 7 is an image of the dilution spot plates for antibacterial susceptibility testing of the pharmaceutical compositions of the disclosure against *E. coli* ATCC 25922.

As shown in FIGS. 6A, 6B, and 7, the F-hectorite-synthetic pyrite mixtures alone did not produce any antibacterial activity, and levels of soluble $Fe^{2+}$ and $H_2O_2$ were below detection limits (i.e., 1 µM and 5 µM, respectively). The pH of the F-hectorite-5% synthetic pyrite mixtures was 5.5 when tested against E. coli (FIG. 6A). The pH of the solution rose to 7.1 after 24 hours as a result of bacterial growth in rich media (TSB). Antibacterial mineral mixtures observed in nature instantaneously release $Fe^{2+}$ and generate $H_2O_2$ upon hydration. Without intending to be bound by theory, it was hypothesized that the cation exchange capacity of the smectite clay minerals was a source of $Fe^{2+}$ that would rapidly release in solution and initiate the redox cycling reactions with pyrite.

Example 4—Preparation and Analysis of $Fe^{2+}$-Exchanged F-Hectorite

A series of experiments using $Fe^{2+}$-exchanged F-hectorites and $Fe^{2+}$-exchanged F-hectorite-synthetic pyrite mixtures were conducted to determine if smectite interlayer $Fe^{2+}$ would initiate antibacterial activity.

All $Fe^{2+}$ exchange reactions were conducted in an anaerobic glove box to prevent the oxidation of $Fe^{2+}$ during sample processing. The concentration of minerals in all $Fe^{2+}$ exchange reactions was 10 mg/mL. Samples were exchanged with 120 mM $FeSO_4$ (nitrogen purged) 3 times and centrifuged at 3500 rpm for 10 minutes between each exchange. After the $Fe^{2+}$ exchange, the samples were rinsed with nitrogen purged DI water in the glove box 3 times, with a centrifugation step between each rinse. The samples were then resuspended in 95% ethanol and centrifuged at 3500 rpm for 10 minutes and dried under a nitrogen purge. After the samples had dried, they were autoclaved at 120° C. for 30 minutes.

Mineral mixtures (50 mg/mL) exchanged with $Fe^{2+}$-exchanged F-hectorite and 5 wt % synthetic pyrite immediately released 2 mM $Fe^{2+}$ during reaction with E. coli in TSB media, and maintained 0.5 mM concentrations of $Fe^{2+}$ over 24 hours (FIG. 6A). These samples resulted in the immediate generation of 319.2 µM $H_2O_2$ and maintained 67.6 µM $H_2O_2$ over 24 hours (FIG. 6B). The initial and 24 hour pH values for the $Fe^{2+}$-exchanged F-hectorite and 5 wt % pyrite mixtures were 4.2 and 3.7, respectively. Bactericidal antibacterial activity was observed after 4 hours (FIG. 7).

The $Fe^{2+}$-exchanged F-hectorites with no added pyrite immediately release 0.7 mM $Fe^{2+}$ and maintained 75 µM $Fe^{2+}$ over 24 hours (FIG. 6A). The concentration of $H_2O_2$ immediately released was 79.2 µM and 7.6 µM $H_2O_2$ over 24 hours (FIG. 6B). Initial and 24 hour pH values were 4.9 and 4.4, respectively. The $Fe^{2+}$-exchanged F-hectorites with no added pyrite were not bactericidal, however they did inhibit bacterial growth over 24 hours (FIG. 7).

A mixture (50 mg/mL) of $Fe^{2+}$-exchanged F-hectorites with 20 wt % synthetic pyrite was also tested for antibacterial activity, $Fe^{2+}$, and $H_2O_2$ generation to determine if increased pyrite concentrations could extend the duration of the ROS generating reactions. These samples resulted in the immediate release of 1.5 mM $Fe^{2+}$ (FIG. 6A). After 4 hours, a drop in $Fe^{2+}$ concentrations was observed, similar to the $Fe^{2+}$-exchanged F-hectorites with or without 5 wt % synthetic pyrite (FIG. 6A). However, after 24 hours, the levels of $Fe^{2+}$ increased to 3.6 mM in the samples containing 20 wt % synthetic pyrite (FIG. 6A). The $H_2O_2$ concentrations followed a similar trend with initial concentrations of 319.2 µM $H_2O_2$ measured, increasing to 464.8 µM $H_2O_2$ after 24 hours (FIG. 6B). The pH values for the 20 wt % synthetic pyrite samples were lower, with values of 3.5 and 2.8 measured initially and after 24 hours, respectively. These samples were bactericidal against E. coli after 4 hours, however the pH decreased to 2.8, which is bactericidal to E. coli and S. epidermidis without the presence of $Fe^{2+}$ and $H_2O_2$ (FIG. 7).

As shown in FIG. 6A, the samples containing 20 wt % pyrite initially released 25% less $Fe^{2+}$ when compared to the samples with 5 wt % synthetic pyrite. Without intending to be bound by theory, it was believed that the immediate release of $Fe^{2+}$ was predominately from the F-hectorite interlayer spaces as the samples containing no pyrite released $Fe^{2+}$ at 0.7 mM concentrations upon hydration (FIG. 6A). However, the overall extent of $Fe^{2+}$ release in the $Fe^{2+}$-exchanged F-hectorite samples including synthetic pyrite was greater when compared to the pure $Fe^{2+}$-exchanged F-hectorite samples containing no pyrite, despite the samples with synthetic pyrite having overall lower wt % clay (hectorite) content. Without intending to be bound by theory, it was believed that the difference in the $Fe^{2+}$ release was a result of redox reactions driving pyrite oxidation.

Example 5—Single $Fe^{2+}$ Cationic Exchange with F-Hectorites

It was observed that the pH of mineral suspensions decreased during cation exchange with $Fe^{2+}$ and subsequent washing with DI water. Additionally, the preparation of $Fe^{2+}$-exchanged F-hectorites in an anaerobic glove box was time consuming and limited the scaling of the synthesis for commercial applications. To mitigate these challenges, a series of samples were prepared under normal atmospheric conditions using nitrogen purged solutions and limited $Fe^{2+}$ exchange steps. Concentrations of synthetic pyrite in the mineral mixtures and $Fe^{2+}$ used in the exchange reactions were varied to determine the minimum concentrations needed to achieve antibacterial activity, while preventing more acidic pH values.

Figure 8A:
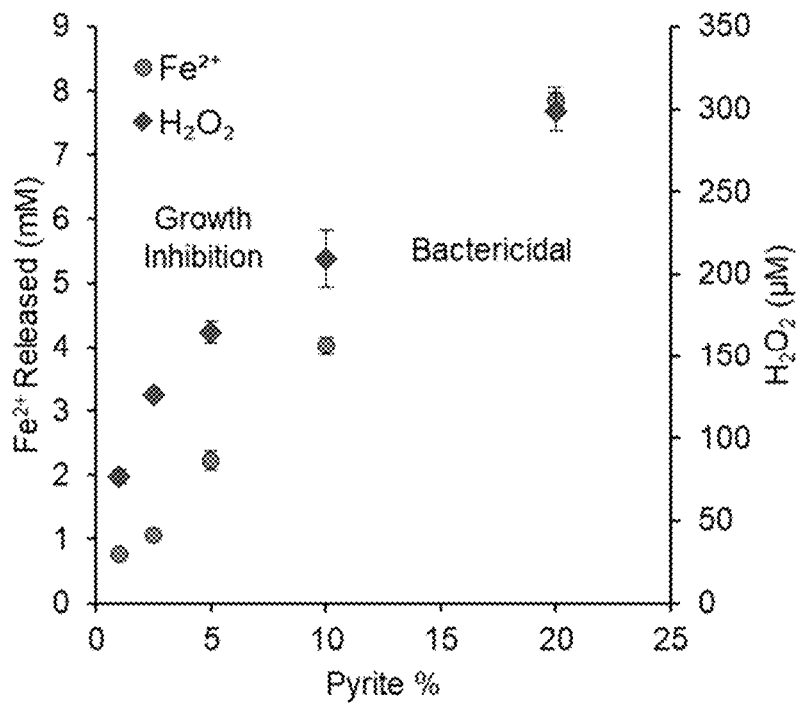
FIG. 8A is a graph of the concentration of ferrous iron and hydrogen peroxide released after 4 hours from a pharmaceutical composition comprising a $Fe^{2+}$-exchanged fluorinated synthetic hectorite (exchanged with a fixed $Fe^{2+}$ concentration, 30 mM) with varying synthetic Fe-sulfide concentrations.
Figure 8B:
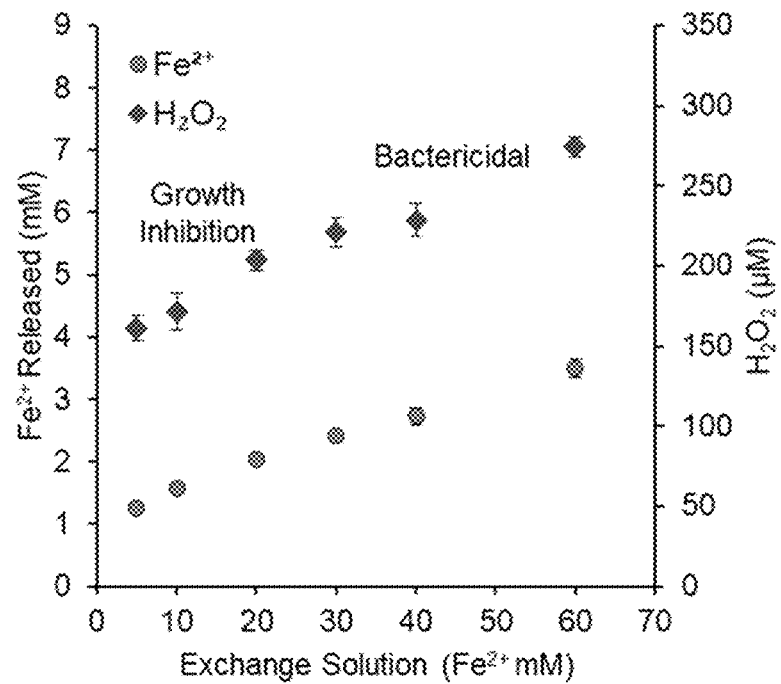
FIG. 8B is a graph of the concentration of ferrous iron and hydrogen peroxide released after 4 hours from a pharmaceutical composition comprising a $Fe^{2+}$-exchanged fluorinated synthetic hectorite (exchanged with various $Fe^{2+}$ concentrations) with a fixed synthetic Fe-sulfide concentration (5 Wt. % Fe-sulfide).
Figure 8C:
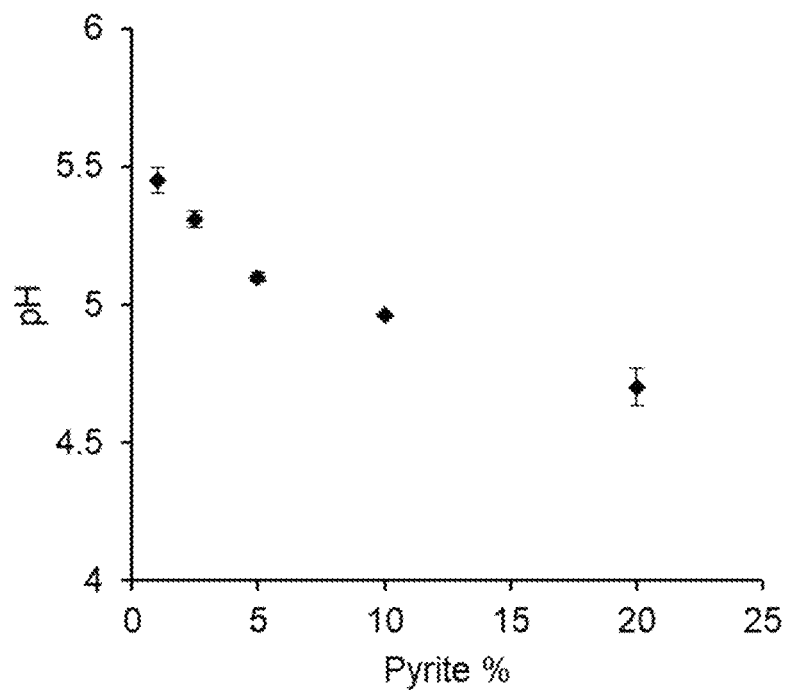
FIG. 8C is a graph of the effect of synthetic Fe-sulfide concentrations on pH.
Figure 8D:
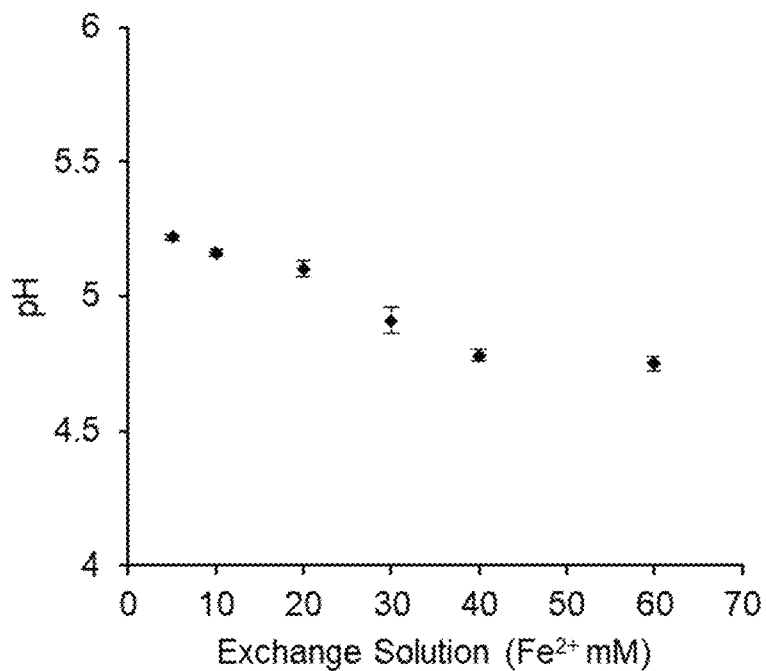
FIG. 8D is a graph of the effect of the $Fe^{2+}$ exchange solution concentration on pH.

The $Fe^{2+}$ exchange reactions in ambient atmospheric conditions were all performed in nitrogen purged solutions. Solutions of DI water were purged for 1 hour with nitrogen and $FeSO_4$ solutions were prepared under constant nitrogen purge. The $Fe^{2+}$ exchange of F-hectorite-synthetic pyrite mixtures was carried out in two ways. First, a series of F-hectorite clays were mixed with varying concentrations of synthetic pyrite, ranging from 1.5 wt % to 20 wt % synthetic pyrite, and exchanged once with 20 mM $FeSO_4$ (FIGS. 8A & 8C). Second, a series of F-hectorite clays were mixed with a fixed 5 wt % synthetic pyrite concentration and exchanged with varying concentrations of $FeSO_4$ solutions, ranging from 5 mM to 60 mM. (FIGS. 8B & 8D). All samples were $Fe^{2+}$-exchanged once in an ultrasonic bath for 10 minutes in a sealed centrifuge tube. The concentration of minerals in all $Fe^{2+}$ exchange reactions was 10 mg/mL. After 10 minutes of exchange, the samples were centrifuged for 10 minutes at 3500 rpm in a swinging bucket centrifuge. The supernatant was then decanted and an aliquot of degassed DI water was added to the centrifuge tube. The centrifuge tube was then sealed and the sample was resuspended in an ultrasonic bath for 2 minutes, followed by centrifugation at 3500 rpm for 10 minutes. The supernatant was decanted, and the samples were then resuspended in 95% ethanol in an ultrasonic bath for 2 minutes, followed by centrifugation at 3500 rpm for 10 minutes. The supernatant ethanol was decanted, and the samples were lyophilized for 6 to 18 hours. After lyophilization, the samples were autoclaved for 30 minutes at 120° C. and stored in sealed centrifuge tubes.

All samples were tested for antibacterial activity, $Fe^{2+}$, $H_2O_2$, and pH using *E. coli* growing in TSB broth at a total mineral (i.e., $Fe^{2+}$-exchanged fluorinated hectorite and synthetic pyrite) concentration of 50 mg/mL, with dilution spot plates measured after 4 and 24 hours, as described in Examples 3 & 4.

Figure 9:
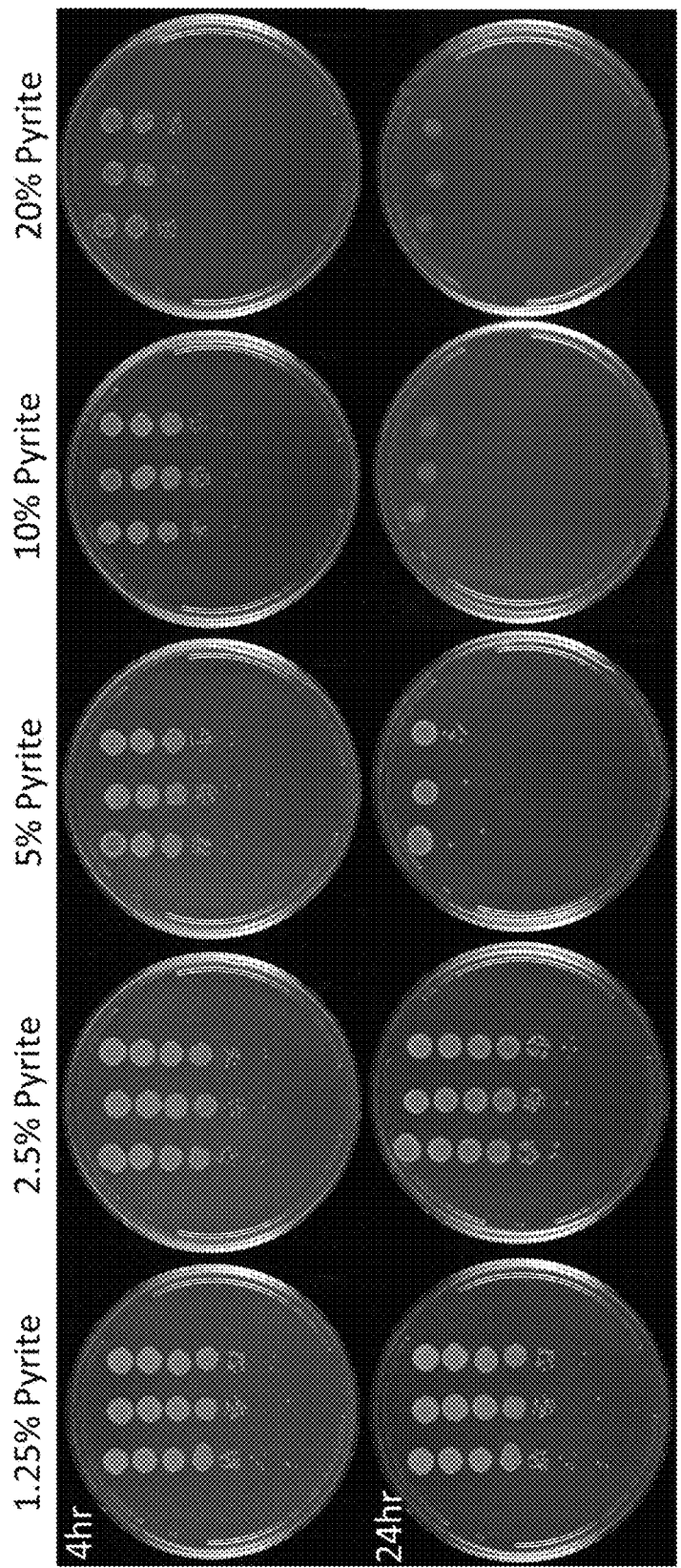
FIG. 9 is an image of the dilution spot plates for antibacterial susceptibility testing of the pharmaceutical compositions of the disclosure with varying pyrite concentrations against *E. coli* ATCC 25922.
Figure 9:
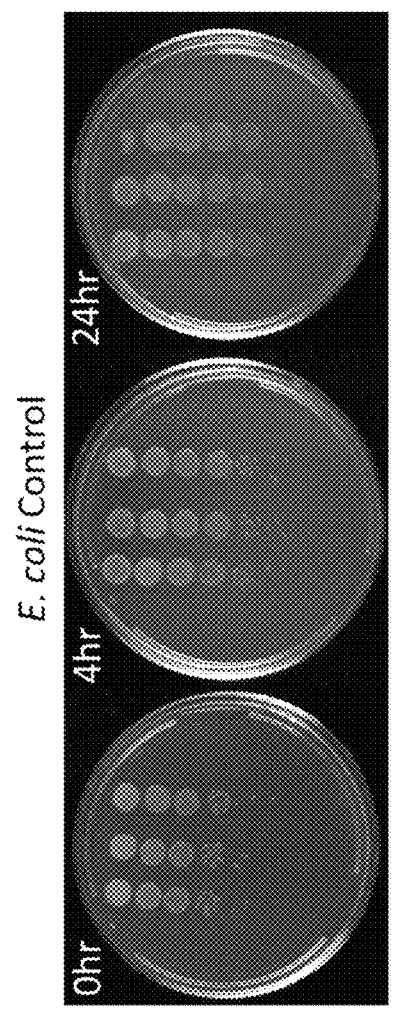

Mineral mixtures with varying pyrite (1.5 to 20 wt %) and a fixed $Fe^{2+}$ exchange solution concentration (20 mM) revealed that increased pyrite loading was directly correlated to increased concentrations of $Fe^{2+}$ and $H_2O_2$ measured in solution (FIG. 8A). The concentrations of $Fe^{2+}$ released after 1 hour ranged from 0.76 mM in samples containing 1.5 wt % pyrite, to 7.9 mM in samples containing 20 wt % pyrite (FIG. 8A). The concentrations of hydrogen peroxide ranged from 77 µM to 300 µM in samples with 1.5 wt % and 20 wt % pyrite, respectively (FIG. 8A). The amount of $Fe^{2+}$ released from samples with 20 wt % pyrite, prepared under ambient conditions with limited exchanges and washes, was over 4 times greater when compared to samples exchanged with 120 mM $Fe^{2+}$ three times, followed by three washes with DI water in a glove box (as described in Example 4, and shown in FIG. 6A). Moreover, the pH values in the samples exchanged only once were higher, with values ranging from 5.45 to 4.7 with pyrite ranging from 1.5 wt % to 20 wt %, respectively (FIG. 8C). The mineral mixtures became bactericidal when pyrite concentrations were at least 10 wt % and $Fe^{2+}$ concentration, $H_2O_2$ concentration, and pH were at least 4 mM, 209.5 µM, and 4.96, respectively (FIGS. 8A & 9). The results indicated that acidity from metal hydrolysis and pyrite oxidation occurred when samples were processed with multiple $Fe^{2+}$ exchanges in a glove box. Without intending to be bound by theory, the presence of $Fe^{3+}$ in solution can initiate pyrite oxidation even in the absence of oxygen (see Reaction 2, above). Limiting the $Fe^{2+}$ exchange and rinsing steps prevent excess acid from accumulating on the negatively charged hectorite clay surfaces.

Figure 10:
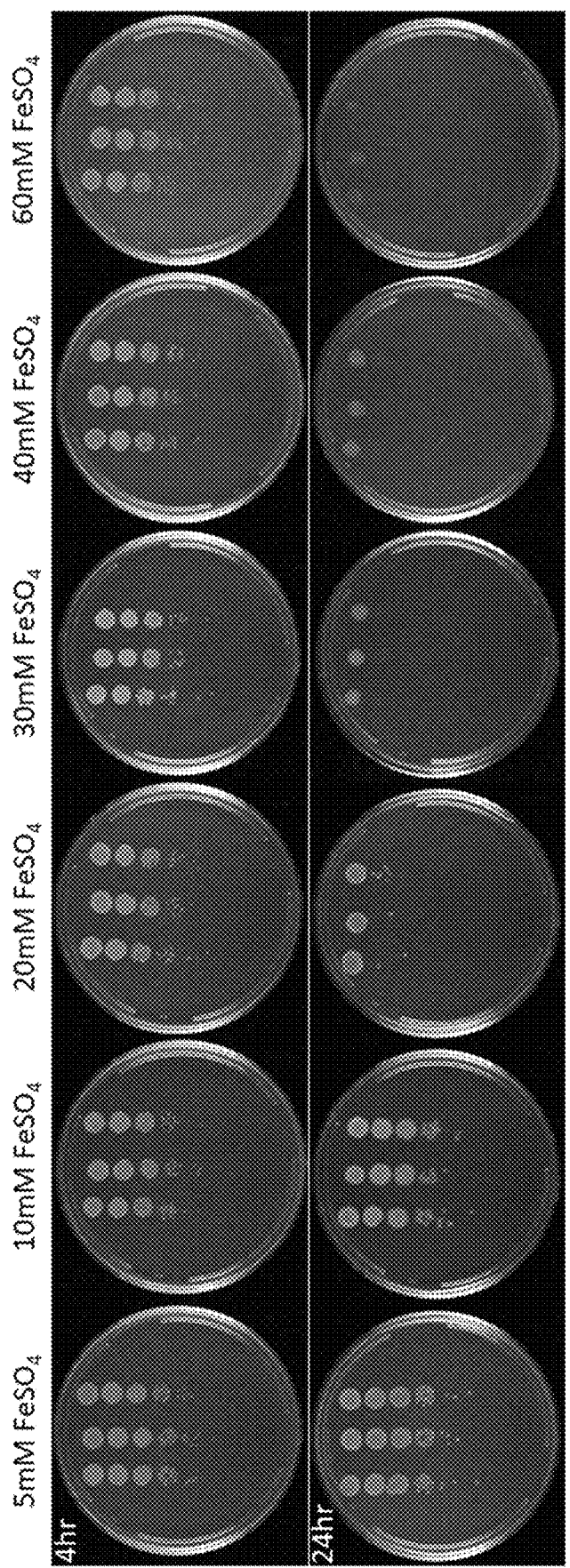
FIG. 10 is an image of the dilution spot plates for antibacterial susceptibility testing of the pharmaceutical compositions of the disclosure with varying $Fe^{2+}$ exchange solution concentrations against *E. coli* ATCC 25922.

Mineral mixtures with a fixed pyrite concentration (5 wt %) and varying concentrations of $Fe^{2+}$ exchange solutions (5 to 60 mM) released 1.3 to 3.5 mM $Fe^{2+}$ and 161.1 to 274.1 µM $H_2O_2$ after 1 hour (FIG. 8B). The increasing concentrations of $Fe^{2+}$ and $H_2O_2$ released correlated with increased concentrations of the $Fe^{2+}$ exchange solutions. The pH in these samples were also higher, with values ranging from 5.22 to 4.75 in samples exchanged with 5 mM to 60 mM $Fe^{2+}$ (FIG. 8D). Samples exchanged with at least 30 mM $Fe^{2+}$ were bactericidal when $Fe^{2+}$ concentrations, $H_2O_2$ concentrations, and pH were at least 2.4 mM, 221.1 µM, and 4.91, respectively (FIGS. 8B & 10). The multiple DI water rinsing steps used in the initial exchange reactions, carried out in anaerobic glove box to limit oxidation (see Example 4) resulted in lower overall $Fe^{2+}$ concentrations and pH values of less than 4.2.

Limited $Fe^{2+}$ exchange reactions and rinsing steps performed in ambient atmospheric conditions still produced mineral compositions with antibacterial properties and resulted in more basic pH values (<4.7). Furthermore, these results showed that the use of an anaerobic glove box and multiple $Fe^{2+}$ exchanged reactions were not required to produce antibacterial mineral formulations that generate extended release $Fe^{2+}$ and ROS.

Example 6—Hydrogel Including $Fe^{2+}$-Exchanged F-Hectorite and Synthetic Pyrite Mineral mixtures containing $Fe^{2+}$-exchanged F-hectorite and synthetic pyrite were embedded in 1 wt % agarose hydrogels to determine if antibacterial activity was observed in a hydrogel matrix.

Mixtures of $Fe^{2+}$-exchanged (30 mM $Fe^{2+}$, ambient conditions) F-hectorite and 5 wt % synthetic pyrite were used for the agarose hydrogel experiments. A 2 wt % solution of agarose was prepared using DI water and microwaved until it dissolved. The agarose solution was then placed in a 65° C. water bath while the mineral mixtures were hydrated. Mineral mixtures were suspended in a sterile isotonic solution (0.9% NaCl) and mixed in a 1:1 ratio with the 2 wt % agarose solution, achieving a final agarose concentration of 1 wt %. The suspension was immediately vortexed for 5 second and 1.5 mL was pipetted into a 12-well plate to cure. Cultures of *E. coli* and *S. epidermidis* were grown to log phase in TSB and diluted to ~$10^8$ CFU/mL. A 1.5 mL aliquot of bacterial culture was added to the 12-well plate containing the mineral agarose composites. The final solution to mineral concentrations in each well were 100, 50, 25, and 12.5 mg/mL. Bacterial growth was monitored using UV-Vis spectroscopy and optical density was sampled and pipetted into a 96-well plate and measured using a microplate reader at 0, 3, and 24 hours. Spot plates were also prepared to determine if the samples were bactericidal. A 20 µL aliquot of sample was deposited onto a TSB-agar plate and incubated at 37° C. for 24 hours. The pH was measured by transferring 1 mL of the culture solution into a 15 mL centrifuge tube after 24 hours.

Figure 11A:
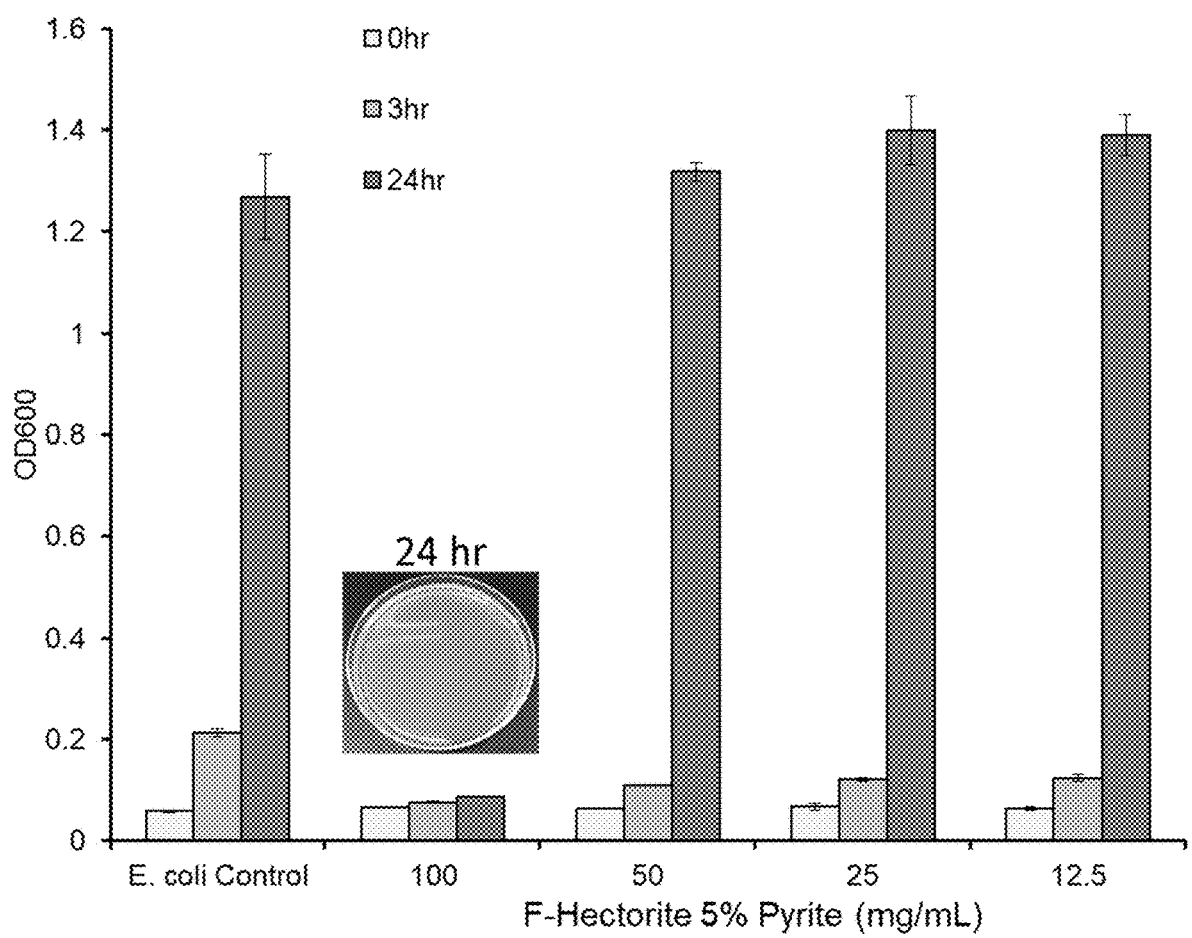
FIG. 11A is a graph of the optical density (OD) at 600 nm and antibacterial susceptibility spot plates of hydrogels comprising the pharmaceutical compositions of the disclosure after exposure to *E. coli*.
Figure 11B:
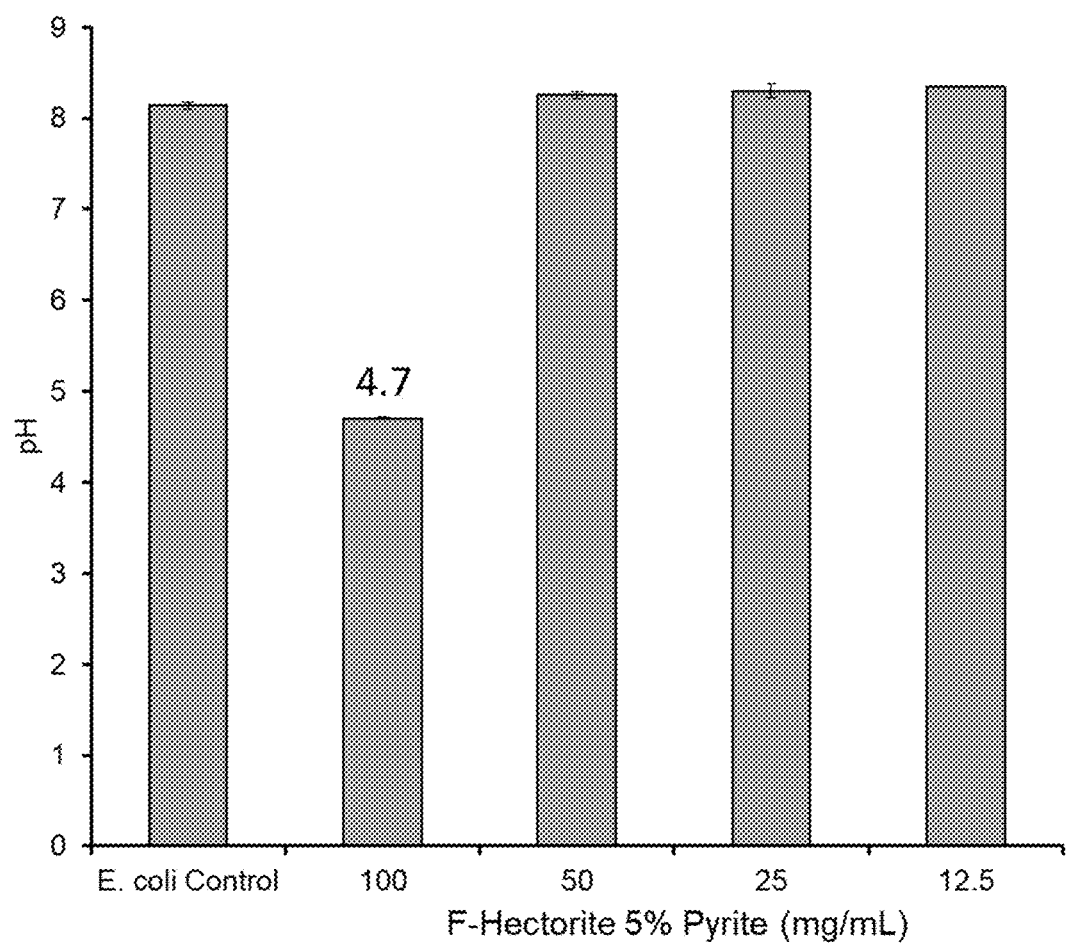
FIG. 11B is a graph of the pH of hydrogels comprising the pharmaceutical compositions according to the disclosure after 24 hours of exposure to *E. coli*. Listed pH values correspond with observed antibacterial activity.
Figure 11C:
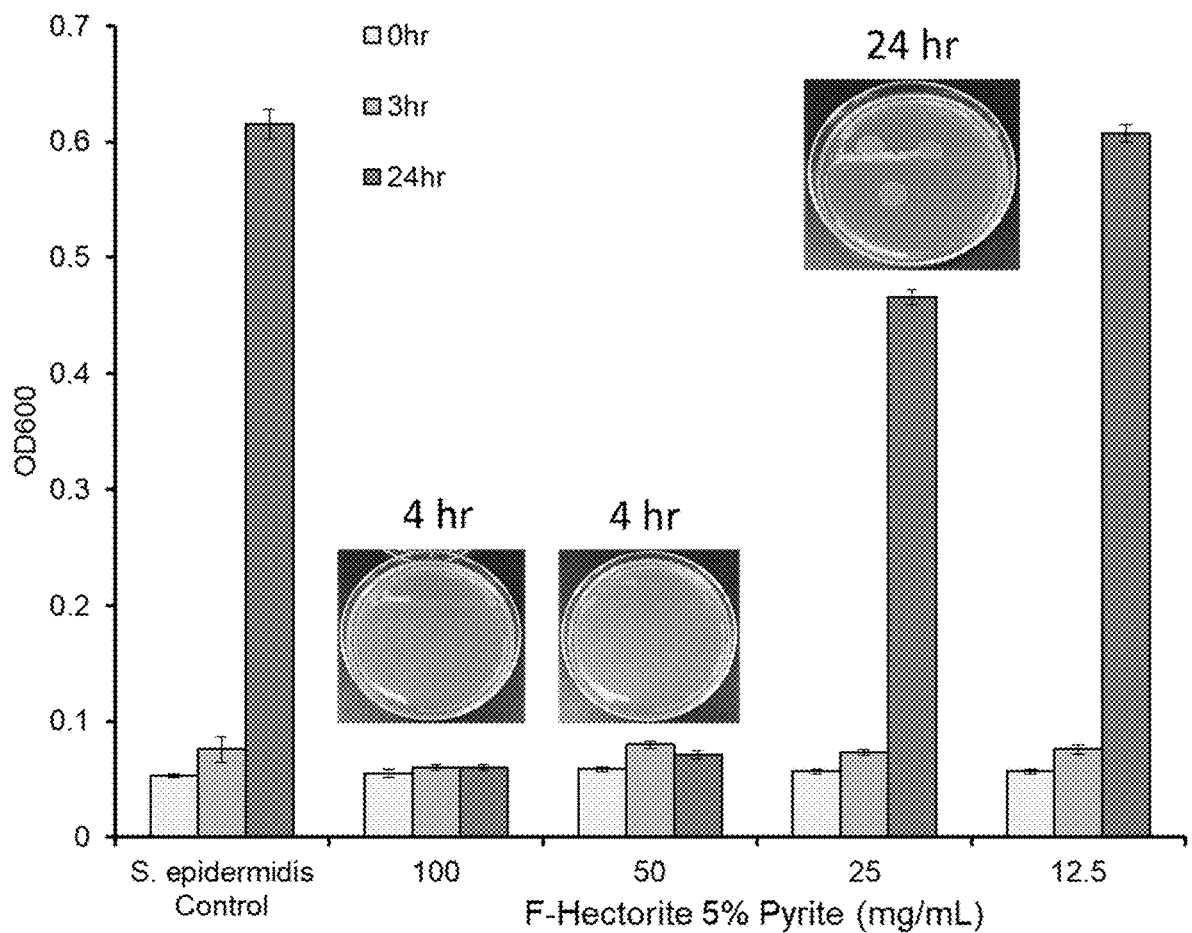
FIG. 11C is a graph of the OD at 600 nm and antibacterial susceptibility spot plates of hydrogels comprising the pharmaceutical compositions of the disclosure after exposure to *S. epidermidis*.
Figure 11D:
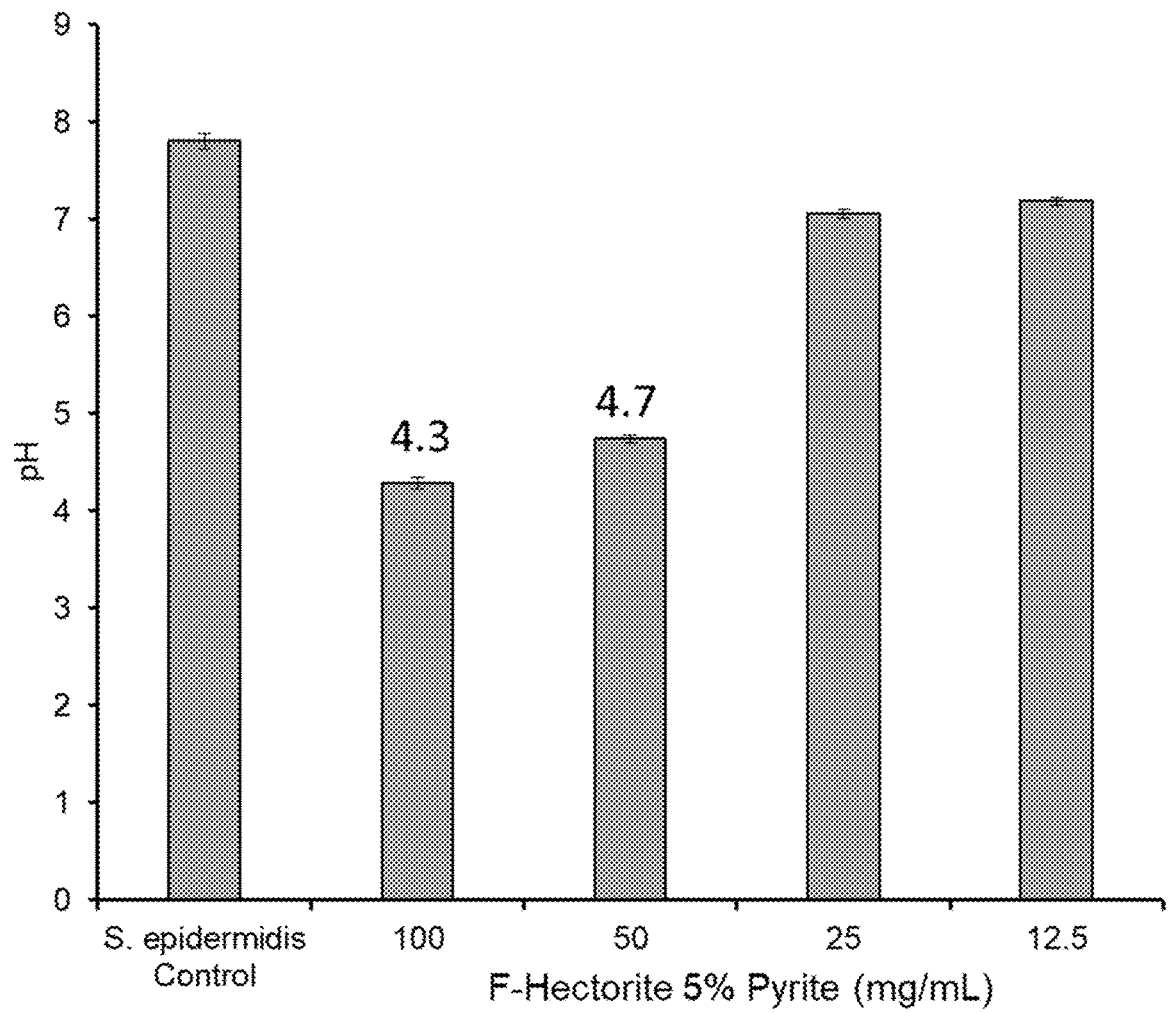
FIG. 11D is a graph of the pH of hydrogels comprising the pharmaceutical compositions according to the disclosure after 24 hours of exposure to *S. epidermidis*. Listed pH values correspond with antibacterial observed activity.

The results from the agarose mineral composite tests against *E. coli* showed antibacterial activity when mineral concentrations reached 100 mg/mL, as shown in FIG. 11A. At this concentration, the samples were bactericidal after 24 hours. Concentrations below 100 mg/mL did not show any antibacterial activity or growth inhibition for *E. coli* cultures. The pH of the antibacterial 100 mg/mL samples dropped to 4.7 after 24 hours (FIG. 11B). The other mineral concentrations (50-12.5 mg/mL) had pH values similar to the *E. coli* control (FIG. 11B). The *S. epidermidis* cells were more sensitive to the mineral agarose composites and bactericidal activity was observed at 50 mg/mL concentrations after 4 hours (FIG. 11C). Concentration of 25 mg/mL resulted in growth inhibition over 24 hours, with pH values measured at 7.1 (FIG. 11D). The bactericidal concentrations (at least 50 mg/mL) had pH values of 4.7 of less after 24 hours.

These results showed that the antibacterial activity was maintained when minerals were embedded in agarose hydrogels, and the release of minerals was prevented, allowing cell growth to be monitored with UV-Vis spectroscopy.

Example 7—Toxicity of Compositions to Dermal Fibroblasts

The viability of 3T3 mouse fibroblasts exposed to the antibacterial mineral mixtures was measured to determine if mammalian cells could withstand the application of a mineral poultice while maintaining antibacterial characteristics. The antibacterial mineral mixtures were prepared as described previously with 95 wt % $Fe^{2+}$-exchanged F-hectorite exchanged with 30 mM $FeSO_4$ and 5 wt % synthetic pyrite, autoclaved prior to testing. All experiments were performed in a 12-well plate using 3T3 mouse fibroblast cells grown to 85% confluency in RPMI media supplemented with 10% dialyzed fetal bovine serum. The fibroblast cells were treated with 100 and 25 mg/mL concentrations of the antibacterial mineral mixtures in RPMI media. After 24 hours of exposure, the media and minerals were decanted and the cells were rinsed with 0.9% sterile sodium chloride buffer three times to remove excess minerals. The cells were then trypsinized to detach them from the 12-well cell culture treated plate. Samples were then pelleted in a 1.5 mL centrifuge tube and stained with trypan blue to determine cell viability using a Countess automated cell counter. A control well with no cells and 100 mg/mL minerals was also included to determine if the minerals interfered with the viability assay.

Figure 12:
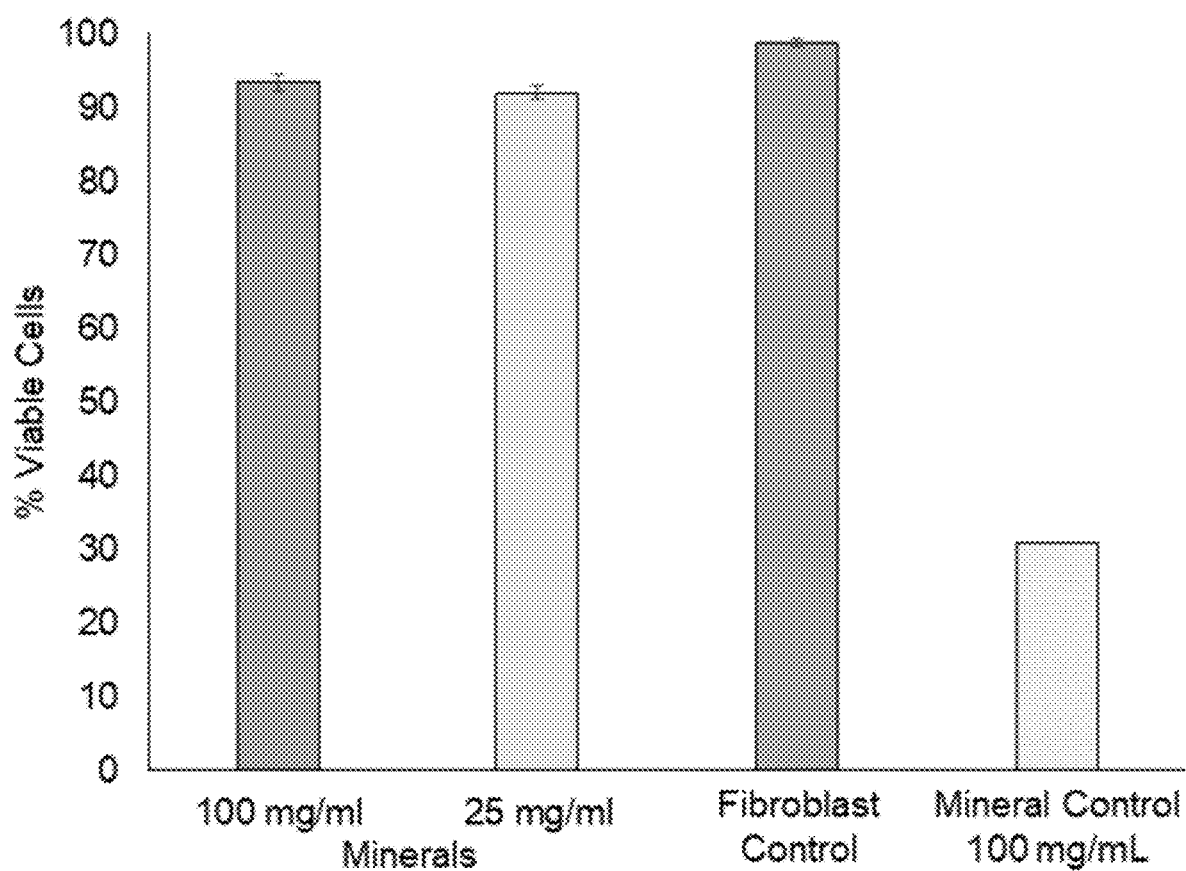
FIG. 12 is a graph of the viability of murine fibroblast cells (NIH T3T) after 24 hours of exposure to pharmaceutical compositions according to the disclosure.

The results from the fibroblast viability assay indicate that fibroblast cells remained viable after a 24-hour exposure to the antibacterial minerals, with approximately 93% of the cells remaining viable (FIG. 12). However, when the minerals with no fibroblast cells were measured on the automated cell counter, a viability of 31% was measured. This indicates that the minerals, to a degree, interfere with the trypan blue and subsequent automated cell counter viability measurement. Subtracting the influence of minerals from the fibroblast cells exposed to the antibacterial minerals indicated that approximately 62% of the fibroblast cells were viable after exposure. These results revealed that fibroblast cells were capable of surviving the toxicity produced from the antibacterial minerals.

Example 8—Antibacterial Susceptibility Testing

The antibiotic resistant ESKAPE pathogens were tested with varying concentrations of synthetic antibacterial minerals. The ESKAPE pathogens include *Enterococcus* sp., *Staphylococcus aureus*, *Klebsiella pneumonia*, *Acinetobacter* sp., *Pseudomonas aeruginosa*, and *Enterobacter* sp. Pharmaceutical mineral compositions that included $Fe^{2+}$ exchanged fluorinated hectorite (exchanged with 30 mM $Fe^{2+}SO_4$) with 5 wt % pyrite was tested against bacteria growing in TSB media (15 g/L). Growth was quantified by spot plating serial dilutions from $10^0$ to $10^{-7}$. The mineral concentrations were varied from 10, 25, 50, 75, and 100 mg/mL. All minerals were resuspended in NaCl to a final concentration of 0.9% when diluted in TSB media at a 1:1 ratio. The release of $Fe^{2+}$ and $H_2O_2$ from mineral suspensions in TSB growth media was measured along with pH over 24 hours.

Figure 13A:
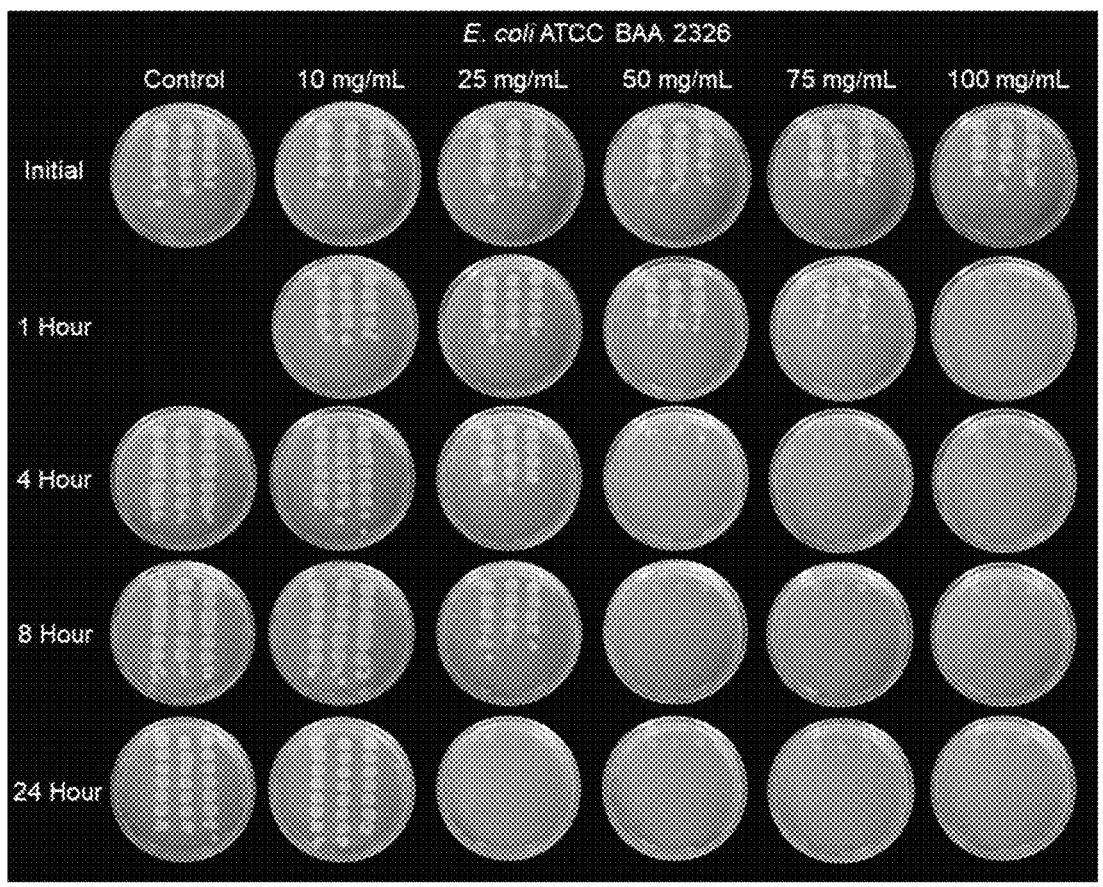
FIG. 13A is an image of dilution spot plates for the antibacterial mineral susceptibility testing of *Escherichia coli* ATCC BAA 2325 (EHEC serotype O104:H4 multi drug resistant, in the Enterobacteriaceae family).
Figure 13B:
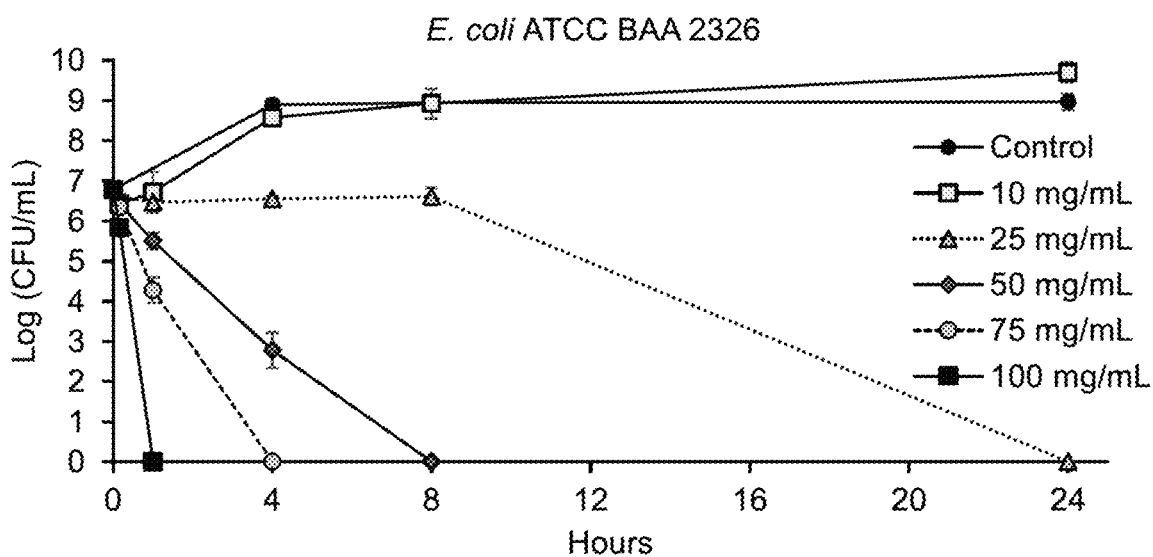
FIG. 13B is a graph showing the cell counts as colony forming units (CFU) per mL for the dilution spot plates of FIG. 13A.

FIGS. 13A and 13B show the results of the antibacterial mineral susceptibility testing of *Escherichia coli* ATCC BAA 2326 (EHEC serotype O104:H4) multi-drug resistant, in the Enterobacteriaceae family. FIG. 13A shows the dilution spot plates and FIG. 13B shows the cell counts as colony forming units (CFU) per mL.

Figure 14A:
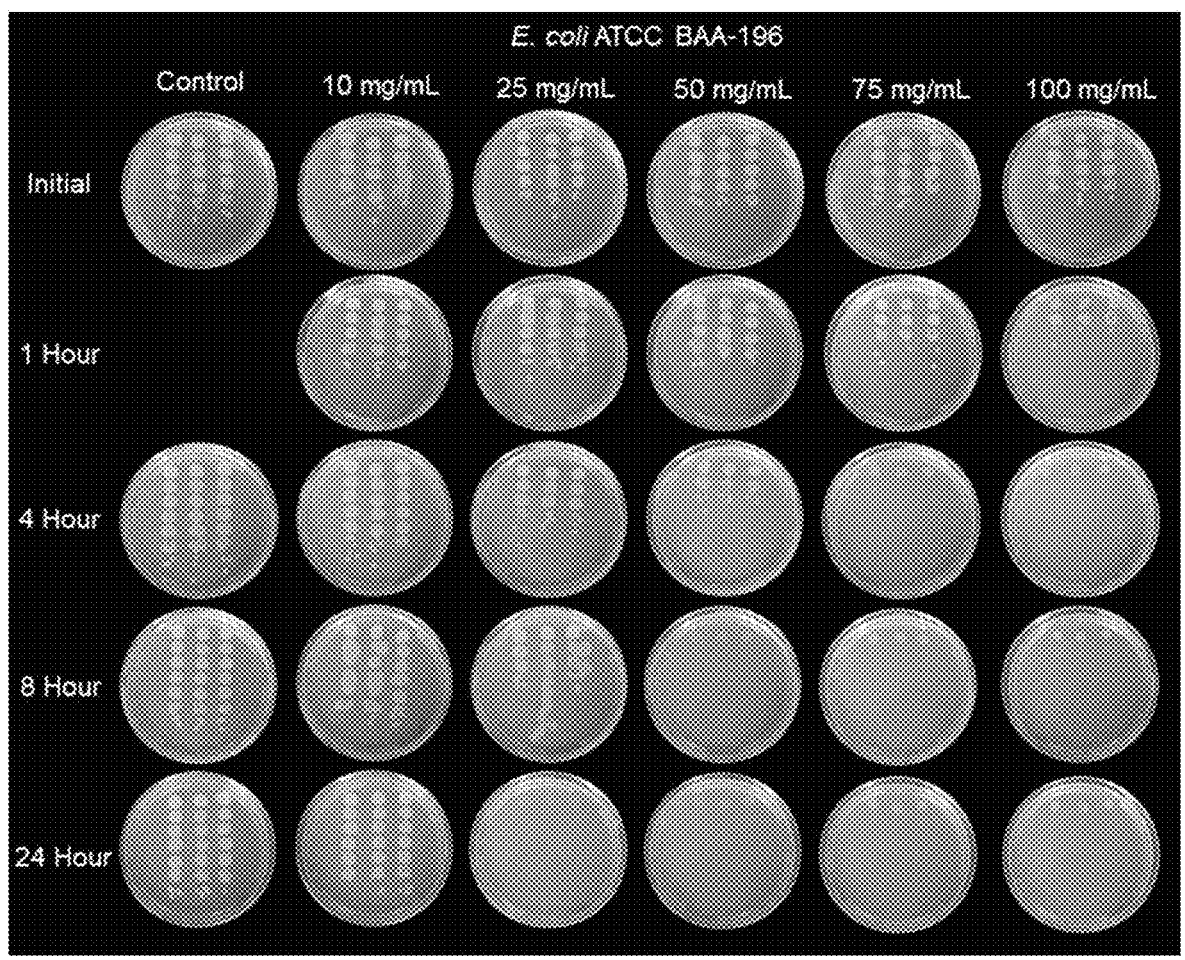
FIG. 14A is an image of dilution spot plates for the antibacterial mineral susceptibility testing of *Escherichia coli* ATCC BAA 196 (extended spectrum β-lactam antibiotic resistant, in the Enterobacteriaceae family).
Figure 14B:
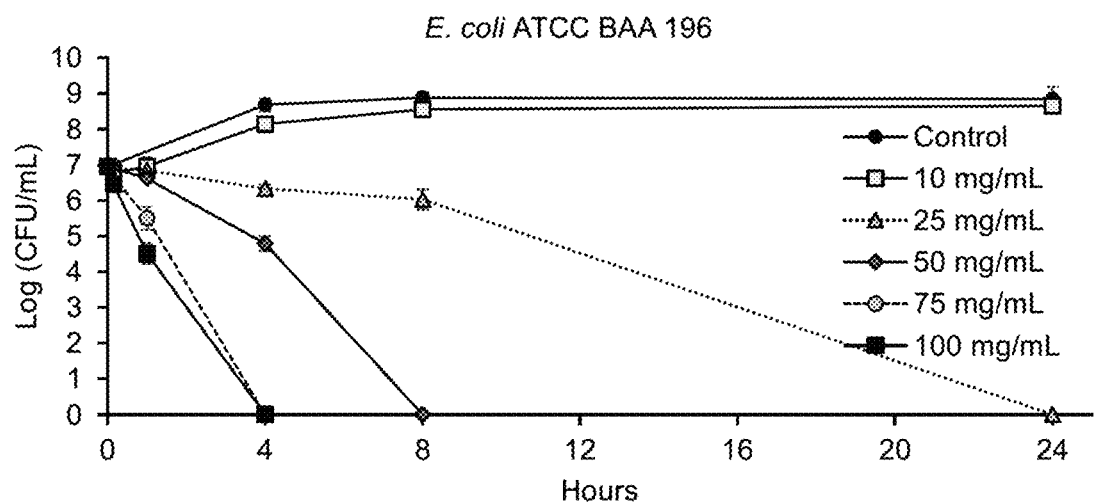
FIG. 14B is a graph showing the cell counts as colony forming units (CFU) per mL for the dilution spot plates of FIG. 14A.

FIGS. 14A and 14B show the results of the antibacterial mineral susceptibility testing of *Escherichia coli* ATCC BAA 196 (extended spectrum β-lactam antibiotic resistant, in the Enterobacteriaceae family). FIG. 14A shows the dilution spot plates and FIG. 14B shows the cell counts as colony forming units (CFU) per mL.

Figure 15A:
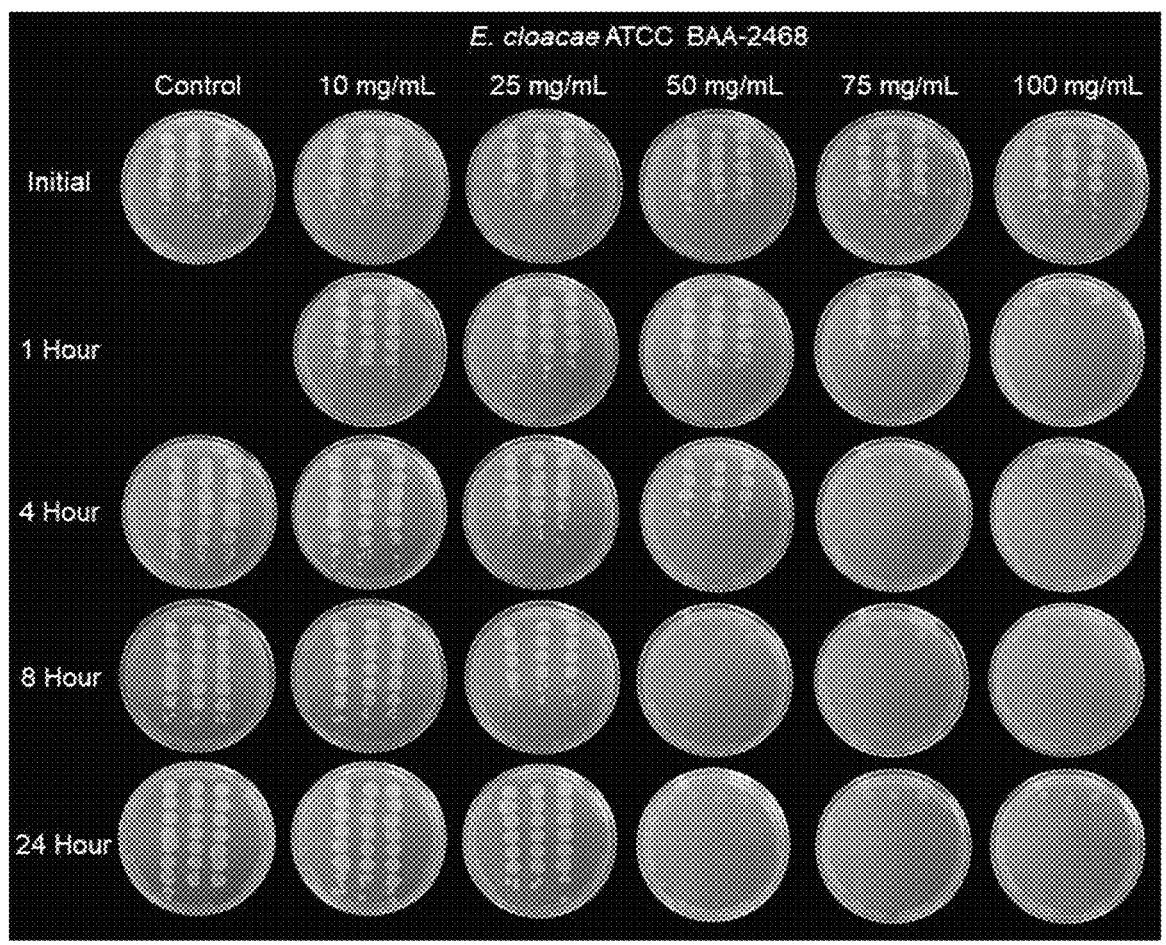
FIG. 15A is an image of dilution spot plates for the antibacterial mineral susceptibility testing of *Enterobacter cloacae* ATCC BAA 2468 (mild drug resistant, in the Enterobacteriaceae family).
Figure 15B:
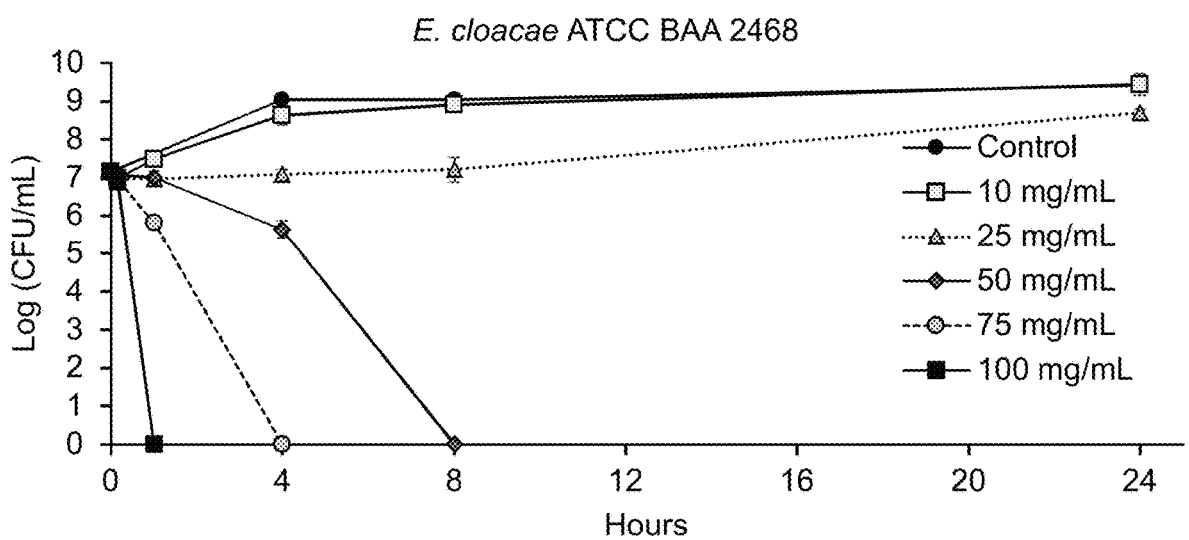
FIG. 15B is a graph showing the cell counts as colony forming units (CFU) per mL of the dilution spot plates of FIG. 15A.

FIGS. 15A and 15B show the results of the antibacterial mineral susceptibility testing of *Escherichia coli* ATCC BAA 2468 (mild drug resistant, in the Enterobacteriaceae family). FIG. 15A shows the dilution spot plates and FIG. 15B shows the cell counts as colony forming units (CFU) per mL.

Figure 16A:
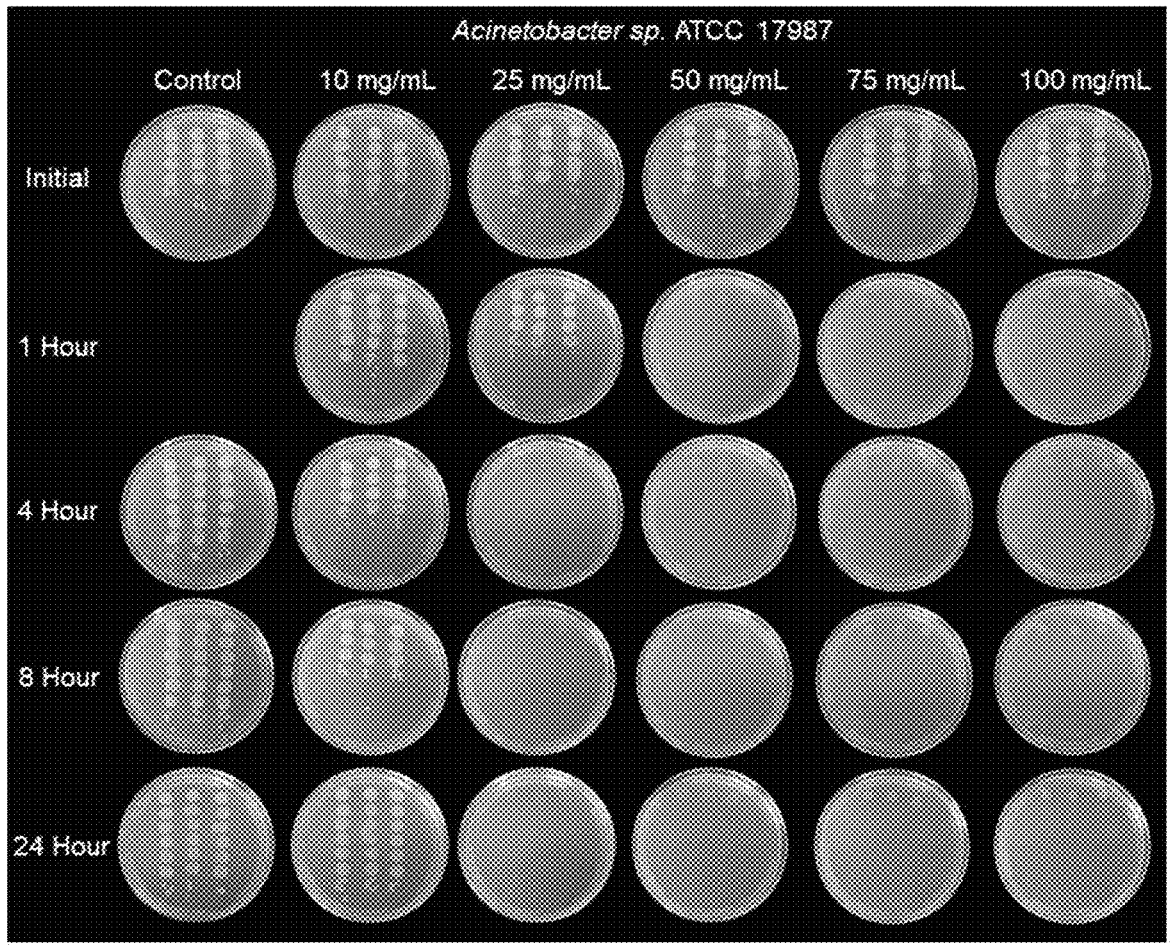
FIG. 16A is an image of dilution spot plates for the antibacterial mineral susceptibility testing of *Acinetobacter* sp. ATCC 17987 (multi-drug resistant).
Figure 16B:
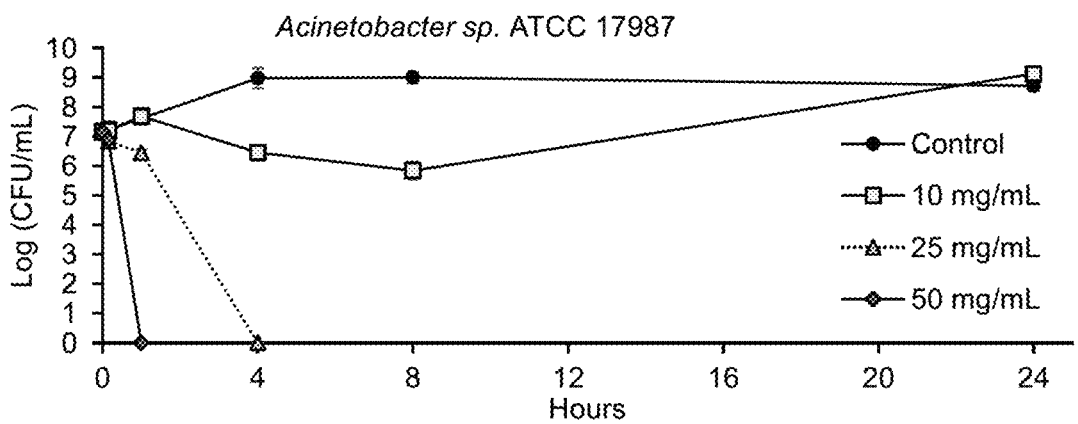
FIG. 16B is a graph showing the cell counts as colony forming units (CFU) per mL of the dilution spot plates of FIG. 16A.

FIGS. 16A and 16B show the results of the antibacterial mineral susceptibility testing of *Acinetobacter* sp. ATCC 17987 (multi-drug resistant). FIG. 16A shows the dilution spot plates and FIG. 16B shows the cell counts as colony forming units (CFU) per mL.

Figure 17A:
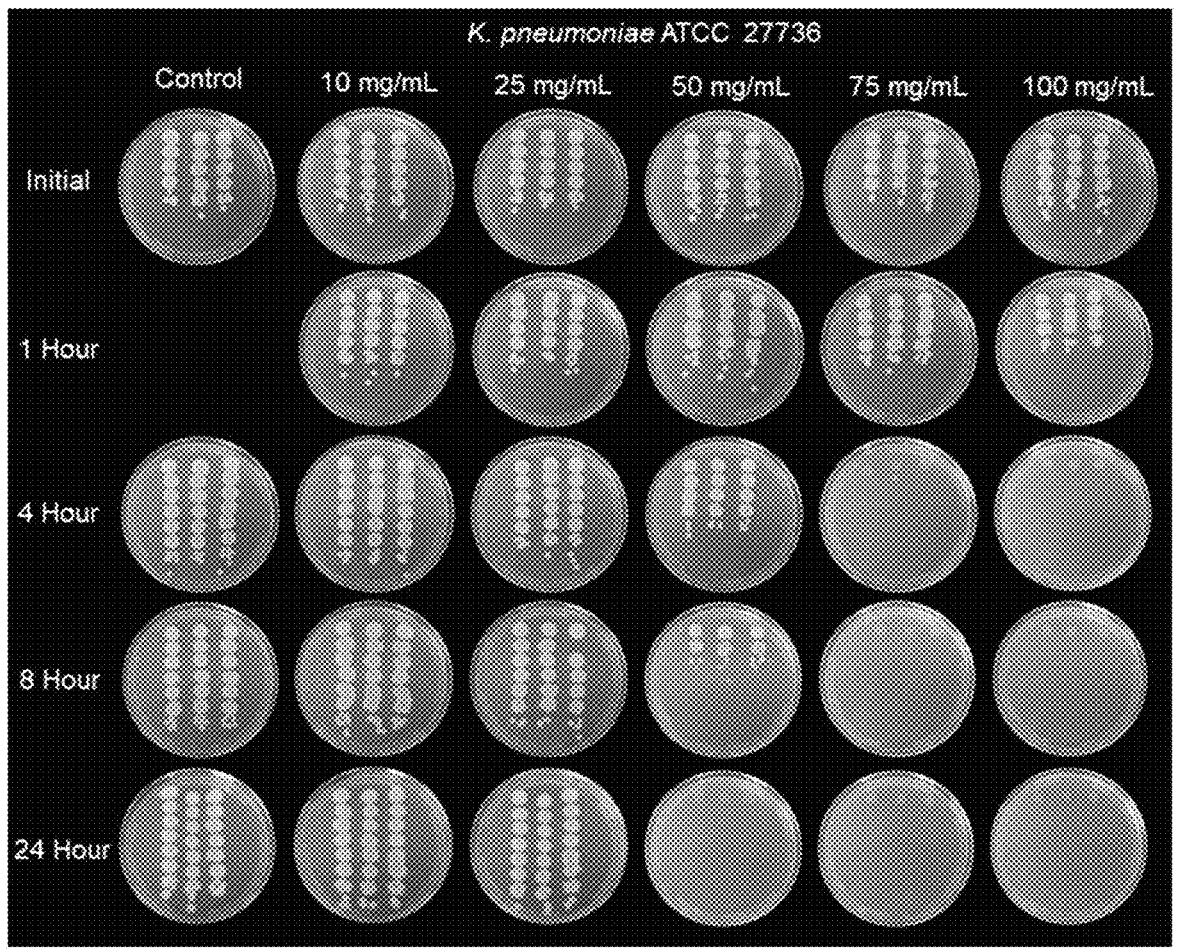
FIG. 17A is an image of dilution spot plates for the antibacterial mineral susceptibility testing of *Klebsiella pneumonia* ATCC 27736 (multi-drug resistant).
Figure 17B:
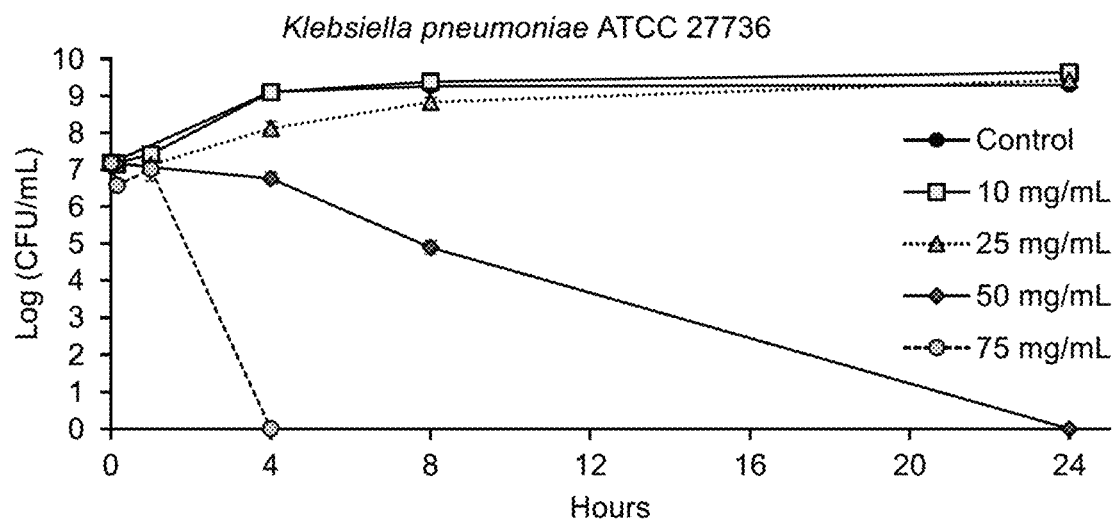
FIG. 17B is a graph showing the cell counts as colony forming units (CFU) per mL of the dilution spot plates of FIG. 17A.

FIGS. 17A and 17B show the results of the antibacterial mineral susceptibility testing of *Klebsiella pneumonia* ATCC 27736 (multi-drug resistant). FIG. 17A shows the dilution spot plates and FIG. 17B shows the cell counts as colony forming units (CFU) per mL.

Figure 18A:
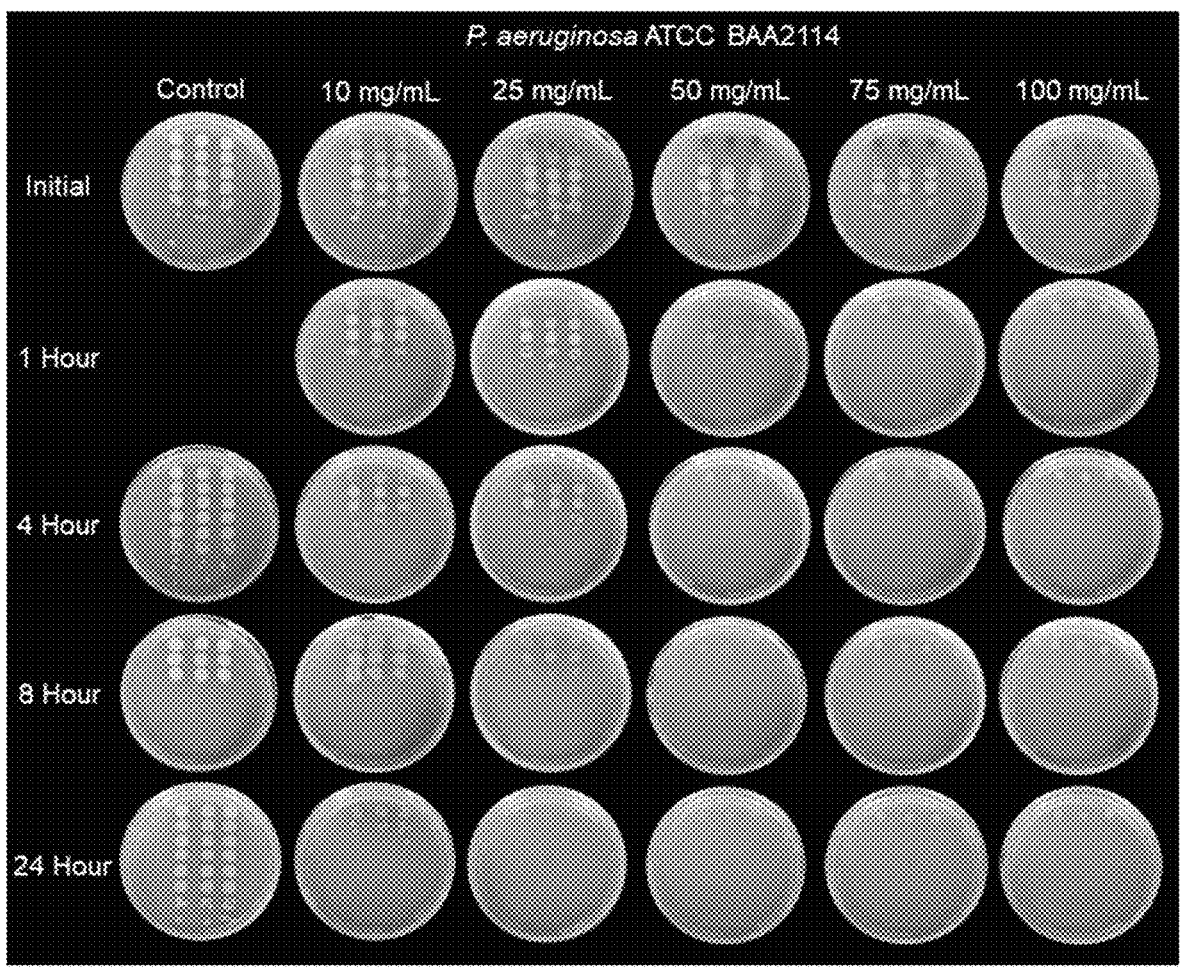
FIG. 18A is an image of dilution spot plates for the antibacterial mineral susceptibility testing of *Pseudomonas aeruginosa* ATCC BAA 2114 (multi-drug resistant).
Figure 18B:
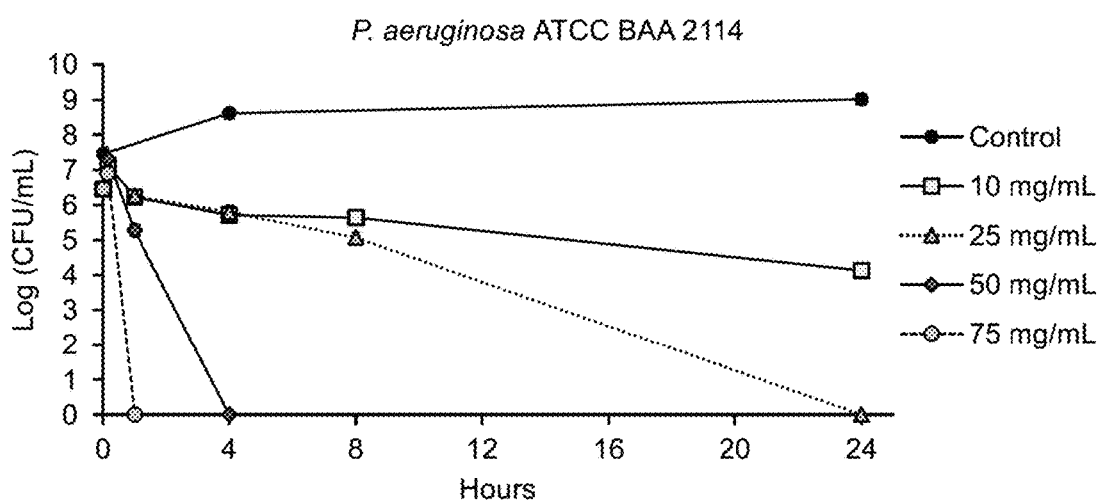
FIG. 18B is a graph showing the cell counts as colony forming units (CFU) per mL of the dilution spot plates of FIG. 18A.

FIGS. 18A and 18B show the results of the antibacterial mineral susceptibility testing of *Pseudomonas aeruginosa* ATCC BAA 2114 (multi-drug resistant). FIG. 18A shows the dilution spot plates and FIG. 18B shows the cell counts as colony forming units (CFU) per mL.

Figure 19A:
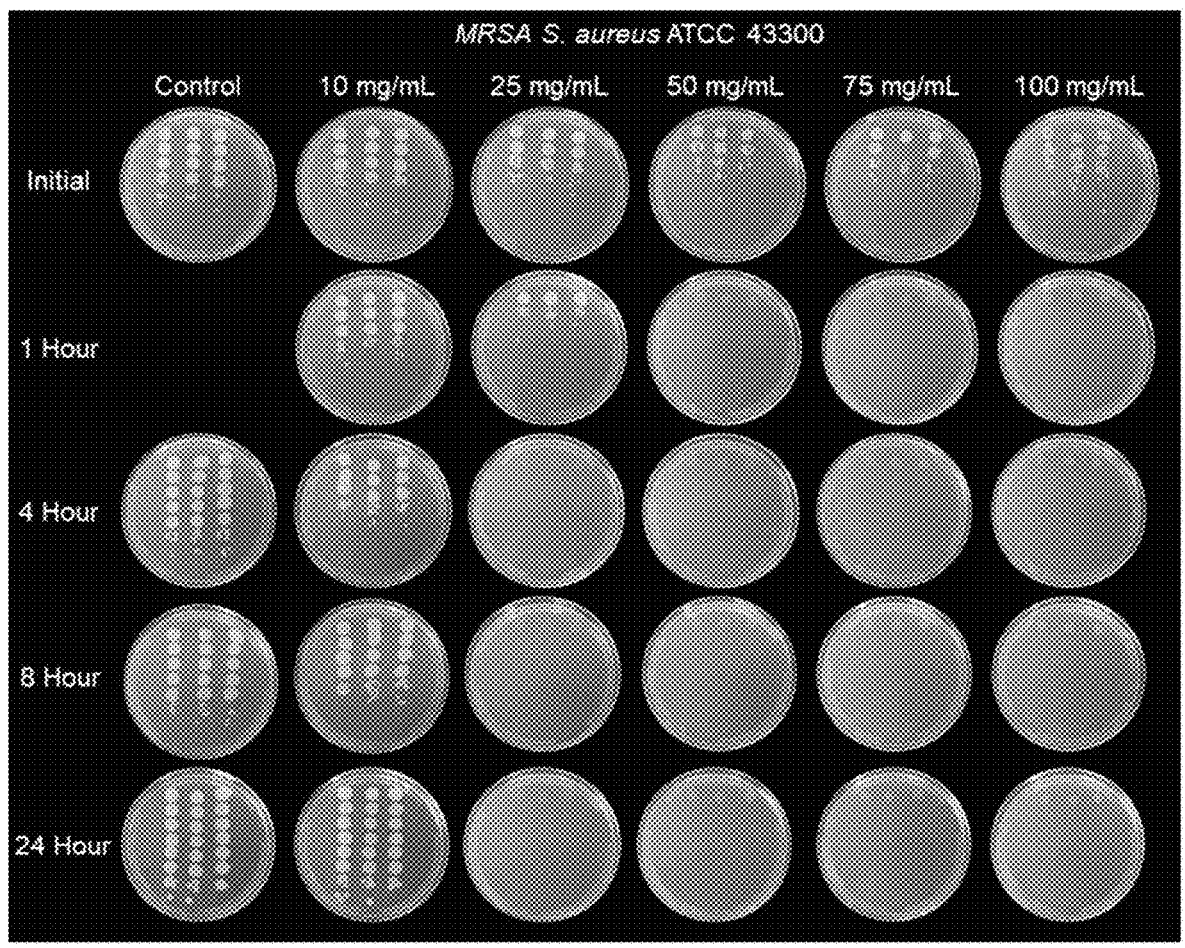
FIG. 19A is an image of dilution spot plates for the antibacterial mineral susceptibility testing of MRSA *Staphylococcus aureus* ATCC 43300 (methicillin resistant).
Figure 19B:
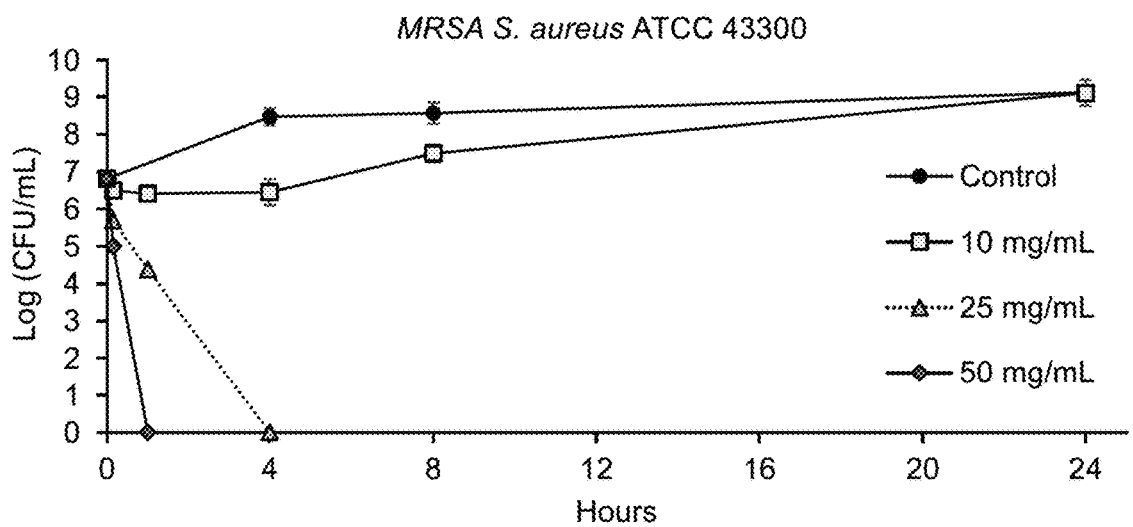
FIG. 19B is a graph showing the cell counts as colony forming units (CFU) per mL for the dilution spot plates of FIG. 19A.

FIGS. 19A and 19B show the results of the antibacterial mineral susceptibility testing of MRSA *Staphylococcus aureus* ATCC 43300 (methicillin resistant). FIG. 19A shows the dilution spot plates and FIG. 19B shows the cell counts as colony forming units (CFU) per mL.

Figure 20A:
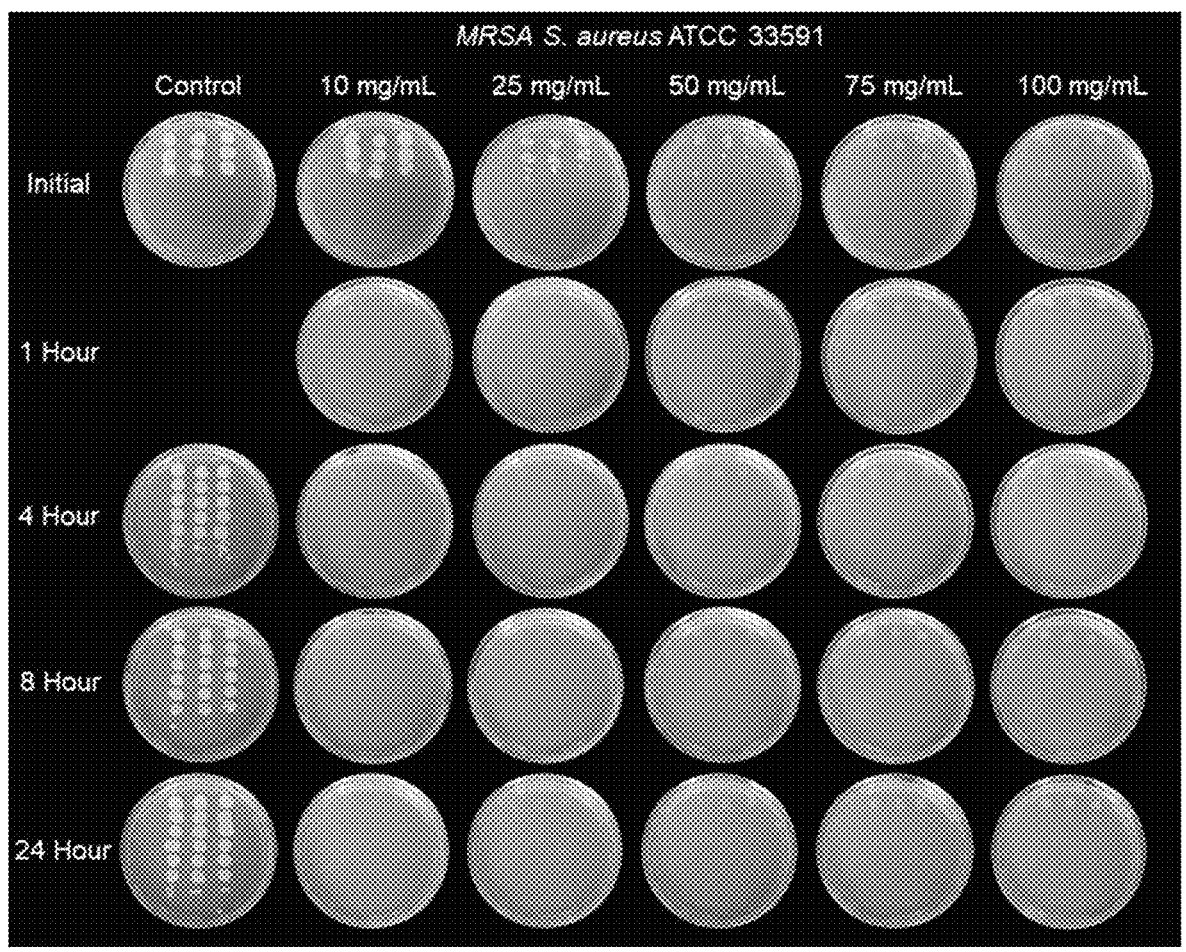
FIG. 20A is an image of dilution spot plates for the antibacterial mineral susceptibility testing of MRSA *Staphylococcus aureus* ATCC 33591 (methicillin and oxacillin resistant).
Figure 20B:
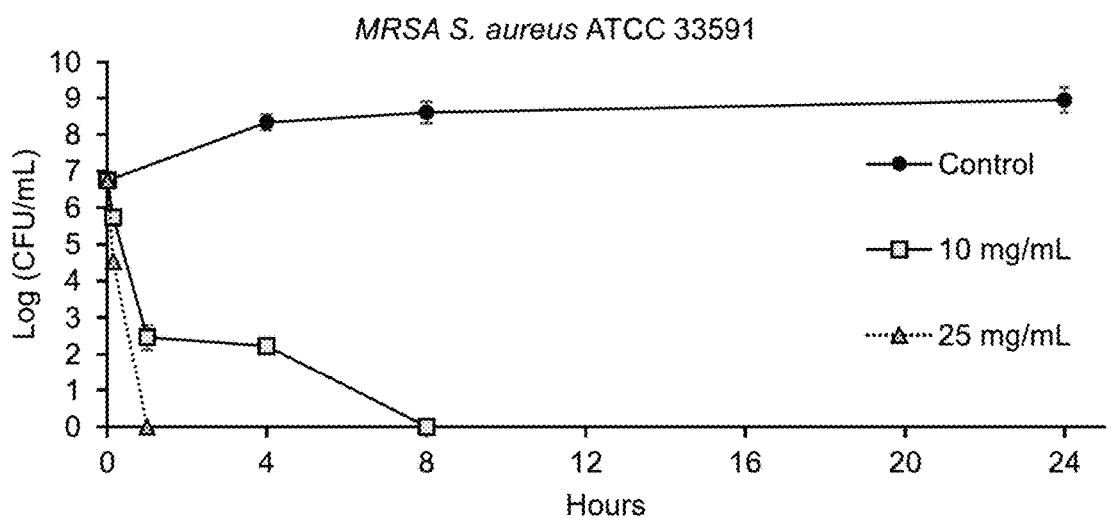
FIG. 20B is a graph showing the cell counts as colony forming units (CFU) per mL for the dilution spot plates of FIG. 20A.

FIGS. 20A and 20B show the results of the antibacterial mineral susceptibility testing of MRSA *Staphylococcus aureus* ATCC 33591 (methicillin and oxacillin resistant). FIG. 20A shows the dilution spot plates and FIG. 20B shows the cell counts as colony forming units (CFU) per mL.

Figure 21A:
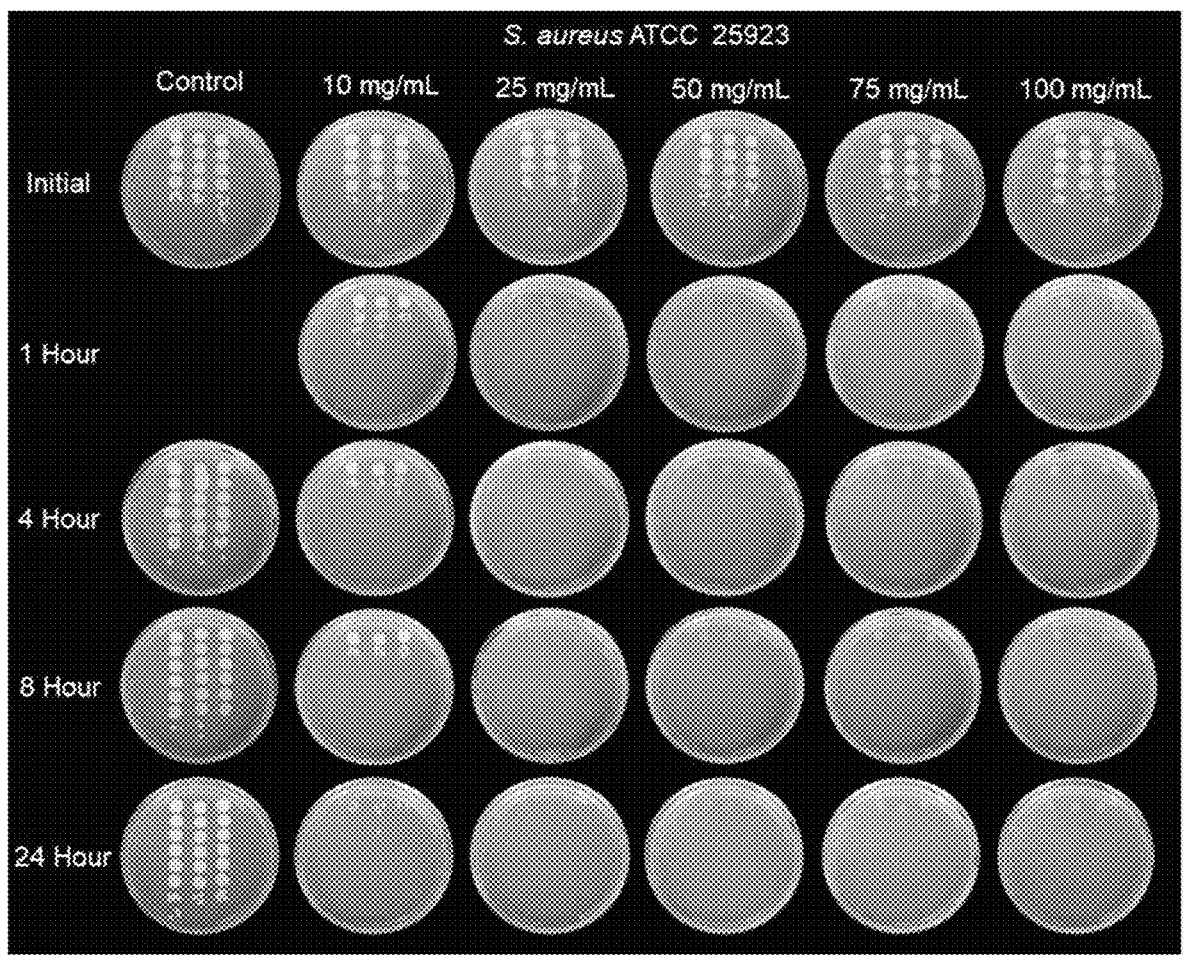
FIG. 21A is an image of dilution spot plates for the antibacterial mineral susceptibility testing of *Staphylococcus aureus* ATCC 25923 (antibiotic susceptible).
Figure 21B:
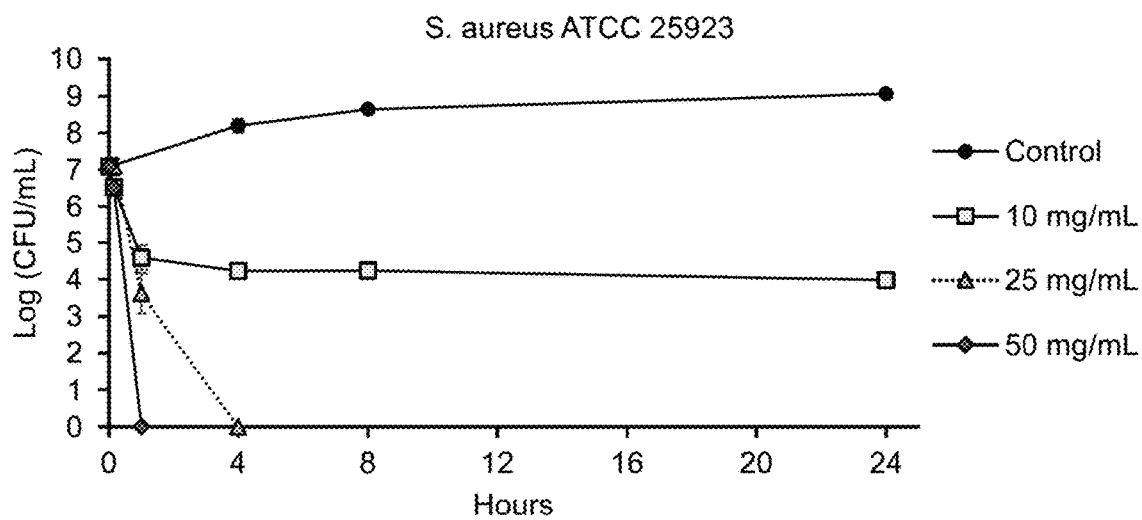
FIG. 21B is a graph showing the cell counts as colony forming units (CFU) per mL for the dilution spot plates of FIG. 21A.

FIGS. 21A and 21B show the results of the antibacterial mineral susceptibility testing of *Staphylococcus aureus* ATCC 25923 (antibiotic susceptible). FIG. 21A shows the dilution spot plates and FIG. 21B shows the cell counts as colony forming units (CFU) per mL.

Figure 22A:
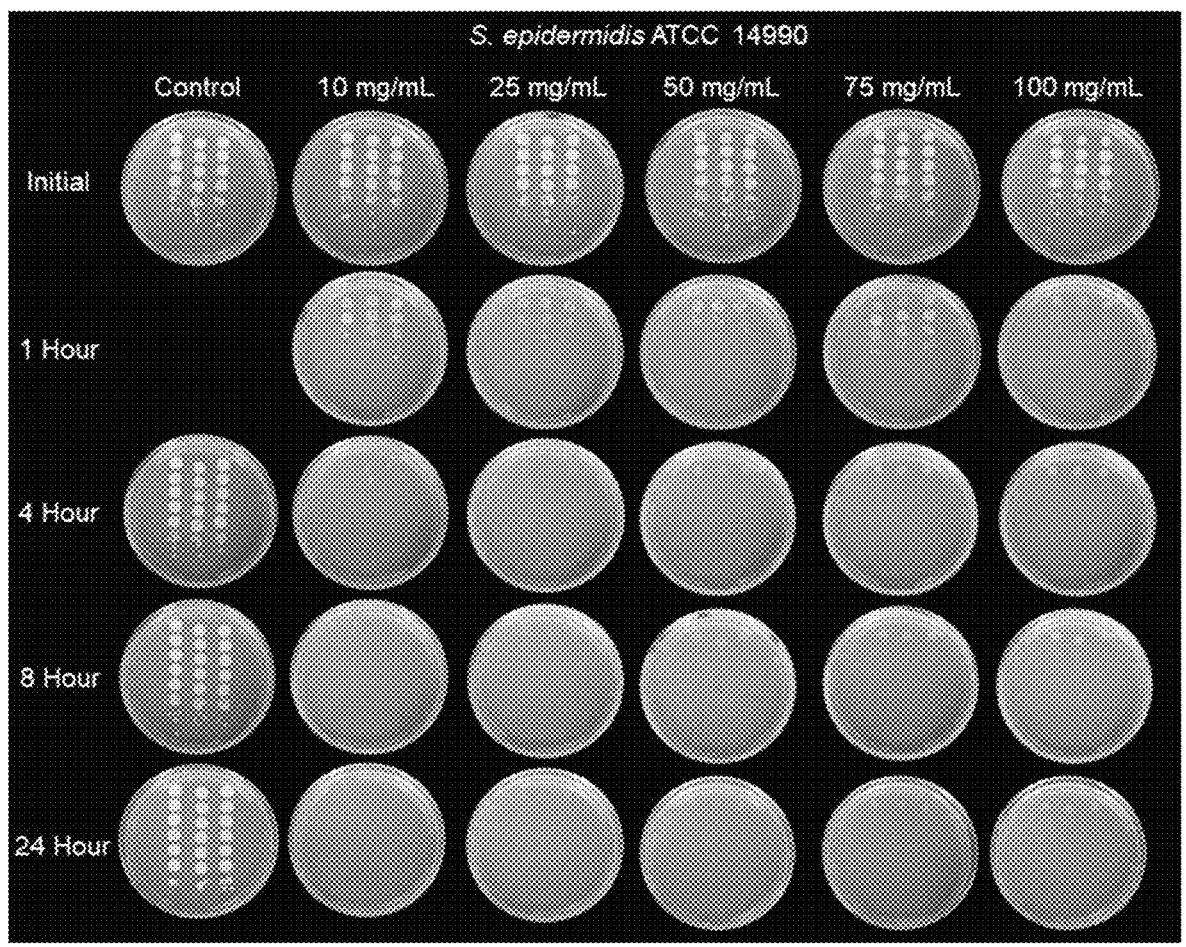
FIG. 22A is an image of dilution spot plates for the antibacterial mineral susceptibility testing of *Staphylococcus epidermidis* ATCC 14990 (antibiotic susceptible).
Figure 22B:
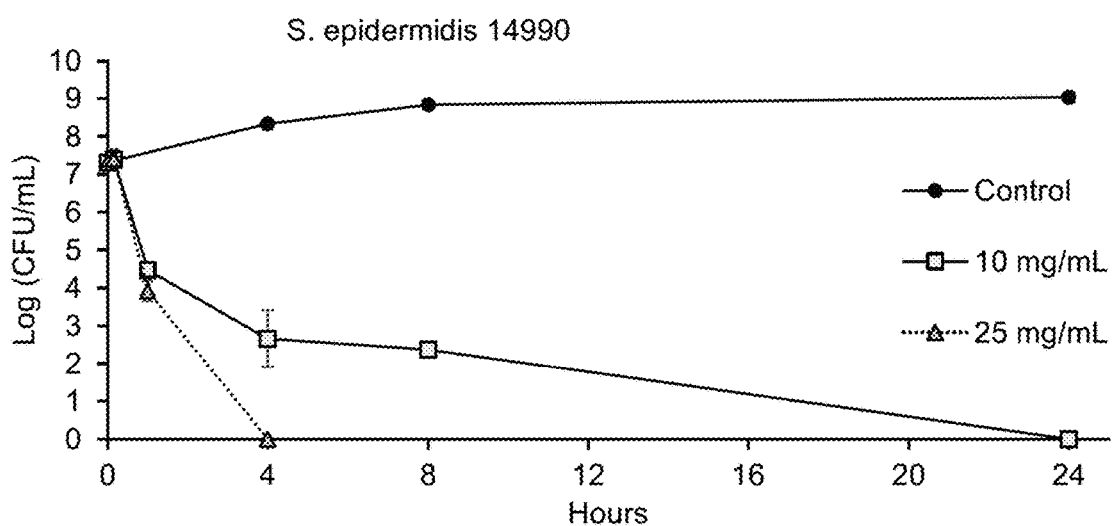
FIG. 22B is a graph showing the cell counts as colony forming units (CFU) per mL for the dilution spot plates of FIG. 22A.

FIGS. 22A and 22B show the results of the antibacterial mineral susceptibility testing of *Staphylococcus epidermidis* ATCC 14990 (antibiotic susceptible). FIG. 22A shows the dilution spot plates and FIG. 22B shows the cell counts as colony forming units (CFU) per mL.

Figure 23A:
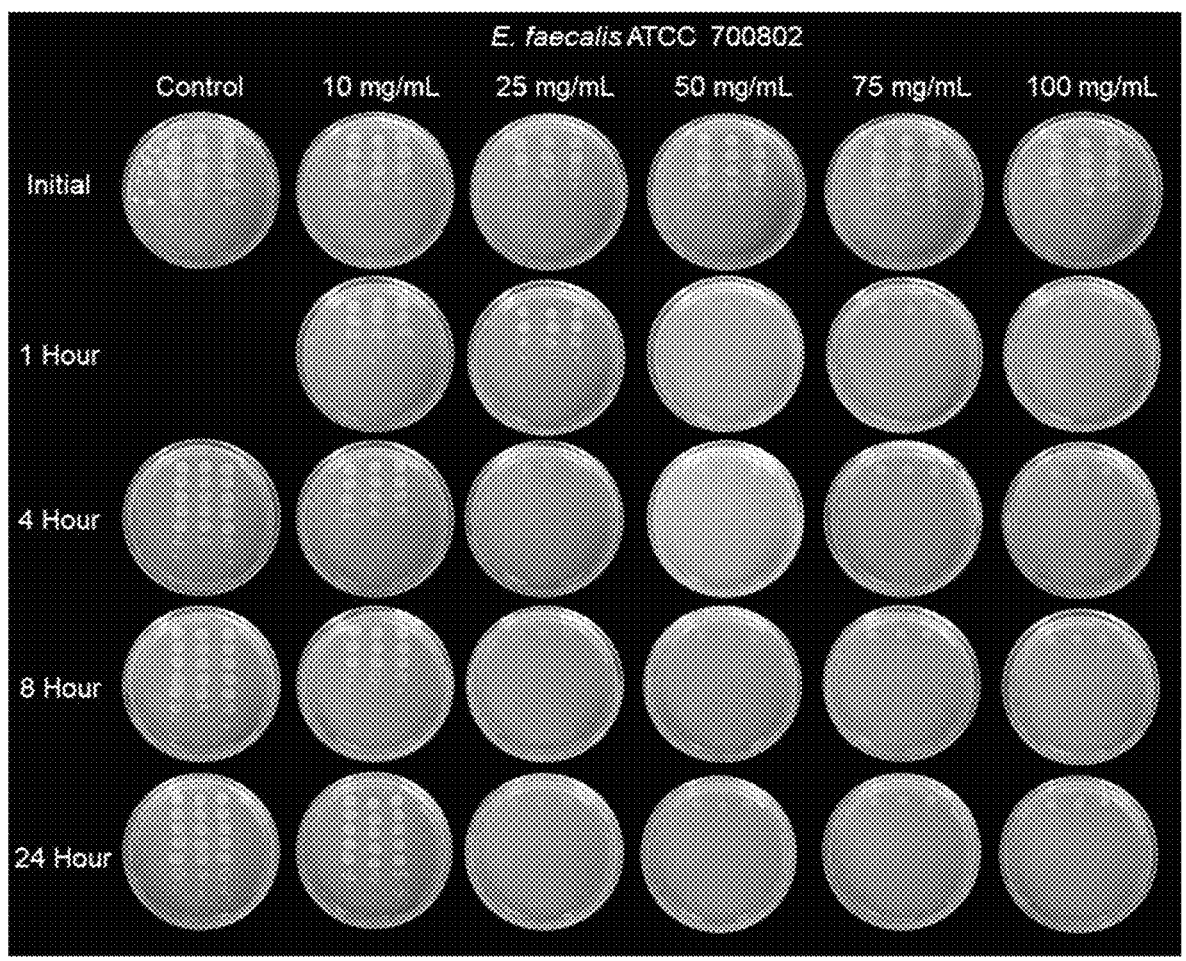
FIG. 23A is an image of dilution spot plates for the antibacterial mineral susceptibility testing of *Enterococcus faecalis* ATCC 700802 (vancomycin resistant).
Figure 23B:
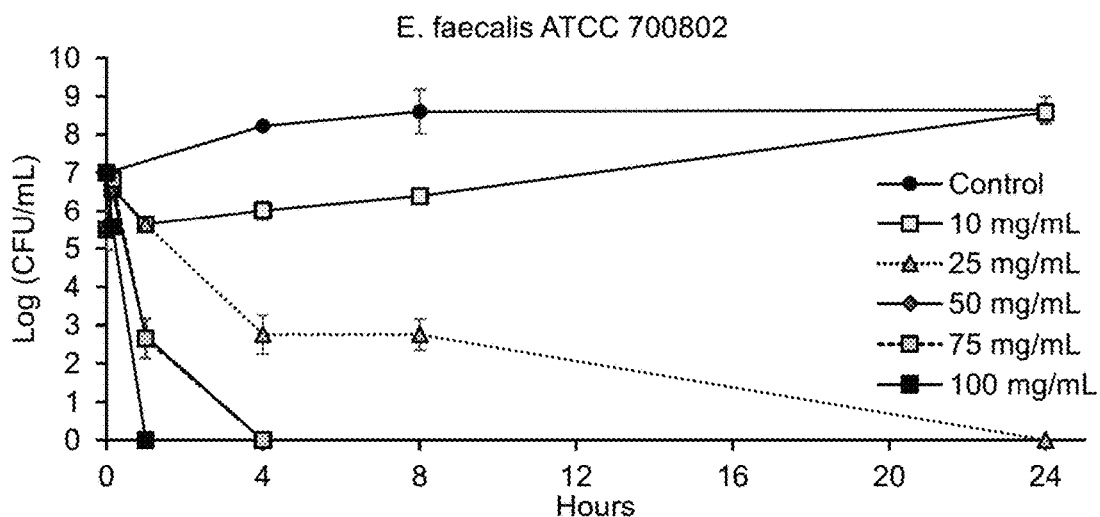
FIG. 23B is a graph showing the cell counts as colony forming units (CFU) per mL for the dilution spot plates of FIG. 23A.

FIGS. 23A and 23B show the results of the antibacterial mineral susceptibility testing of *Enterococcus faecalis* ATCC 700802 (vancomycin resistant). FIG. 23A shows the dilution spot plates and FIG. 23B shows the cell counts as colony forming units (CFU) per mL.

Table 2 shows the synthetic mineral minimum bactericidal concentrations (MBC) measured over 24 hours. Mineral concentrations were varied from 10 to 100 mg/mL.

TABLE 2

| | Time (Hours) | | | |
|---|---|---|---|---|
| | 1 | 4 | 8 | 24 |
| | MBC Mineral Concentration (mg/mL) | | | |
| Gram-negative | | | | |
| *Escherichia coli* BAA-2326 | 100 | 75 | 50 | 25 |
| *Escherichia coli* BAA-196 | >100 | 75 | 50 | 25 |
| *Escherichia cloacae* BAA-2468 | 100 | 75 | 50 | 50 |

TABLE 2-continued

| | Time (Hours) | | | |
|---|---|---|---|---|
| | 1 | 4 | 8 | 24 |
| | MBC Mineral Concentration (mg/mL) | | | |
| Acinetobacter sp. 17987 | 50 | 25 | 25 | 25 |
| Klebsiella pneumonia 27736 | 75 | 75 | 75 | 50 |
| Pseudomonas aeruginosa BAA-2114 | 75 | 50 | 50 | 25 |
| Gram-positive | | | | |
| Staphylococcus epidermidis 14990 | >100 | 25 | 25 | 10 |
| Staphylococcus aureus 25923 | 50 | 25 | 25 | 25 |
| MRSA 33591 | 25 | 25 | 10 | 10 |
| MRSA 43300 | 50 | 25 | 25 | 25 |
| Enterococcus faecalis 700802 | 100 | 50 | 50 | 25 |

The antibacterial mineral susceptibility testing demonstrated that gram-negative pathogens were killed with a 75 mg/mL mineral dose after 8 hours and a 50 mg/mL mineral dose after 24 hours. Gram-positive pathogens were killed with a 50 mg/mL mineral dose after 8 hours and a 25 mg/mL dose after 24 hours.

Figure 24:
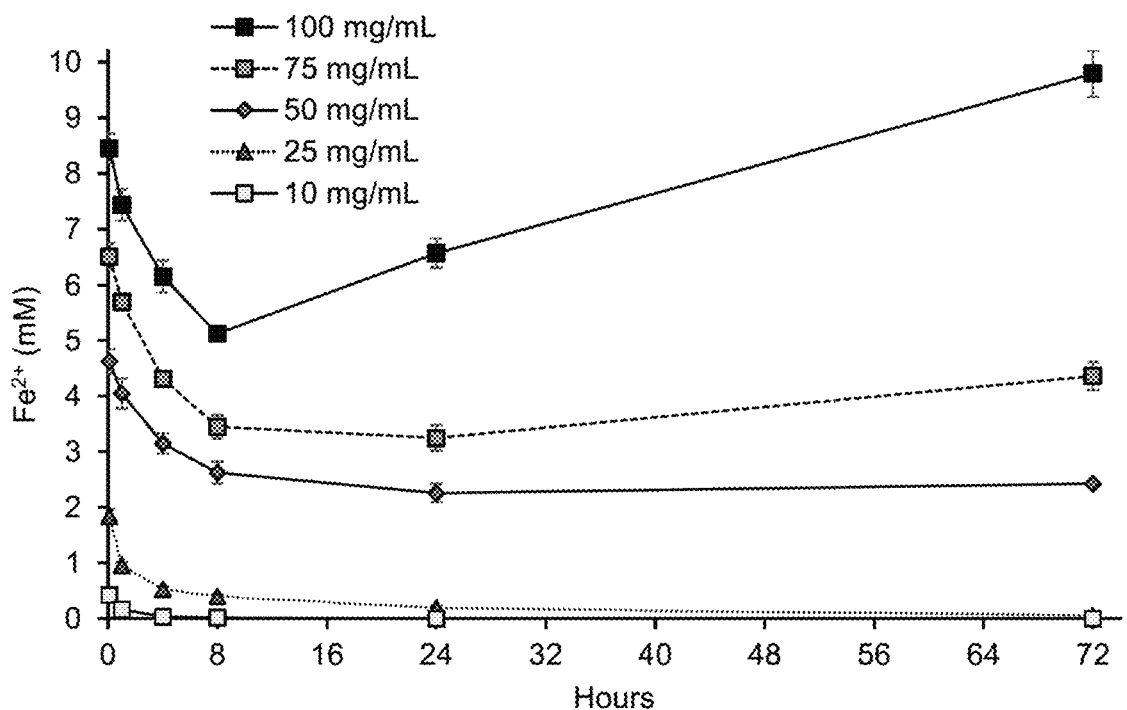
FIG. 24 is a graph showing the ferrous iron release from the synthetic antibacterial minerals (F-Hectorite $Fe^{2+}$ exchanged 30 mM, 5% Fe-sulfide) at varying concentrations of 100, 75, 50, 25, and 10 mg/mL, over 72 hours.

FIG. 24 shows the ferrous iron release from the synthetic antibacterial minerals (F-Hectorite $Fe^{2+}$ exchanged 30 mM, 5% pyrite) at varying concentrations of 100, 75, 50, 25, and 10 mg/mL over 72 hours. The mineral mixture maintained a soluble $Fe^{2+}$ concentration in the range of 9 to 0.01 mM over 72 hours at the tested concentrations.

Figure 25:
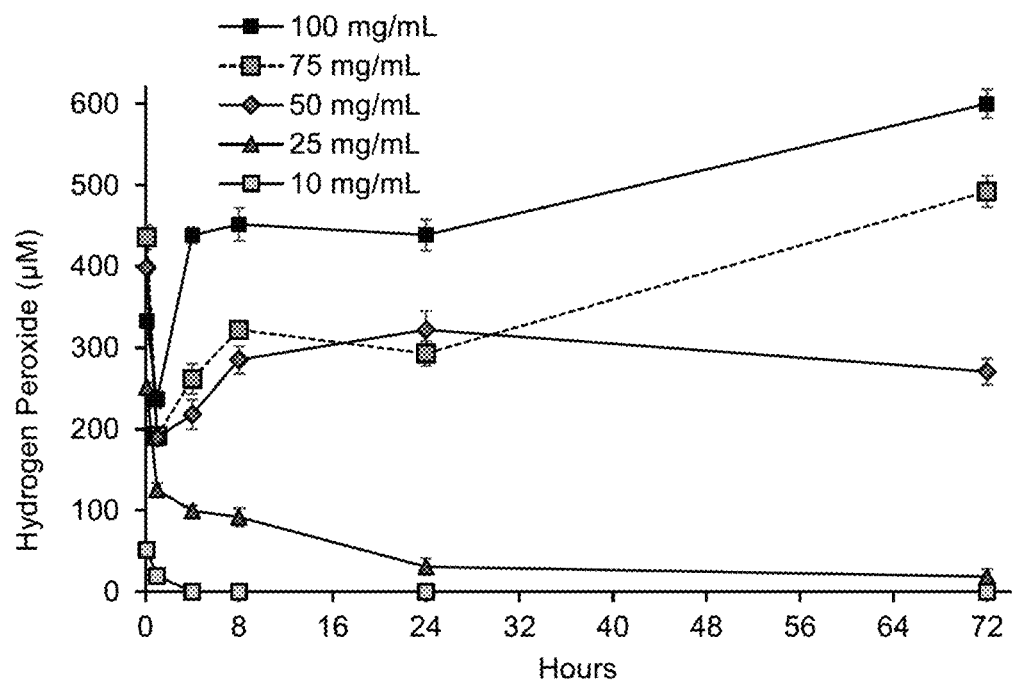
FIG. 25 is a graph showing the hydrogen peroxide release of the synthetic antibacterial minerals at the same varying concentrations as FIG. 24 and measured over 72 hours.

FIG. 25 shows the hydrogen peroxide release of the synthetic antibacterial minerals at the same varying concentrations as FIG. 24 and measured over 72 hours. Mineral concentrations greater than 75 mg/mL demonstrated increased $Fe^{2+}$ release and $H_2O_2$ generation after 8 hours of reaction.

Figure 26:
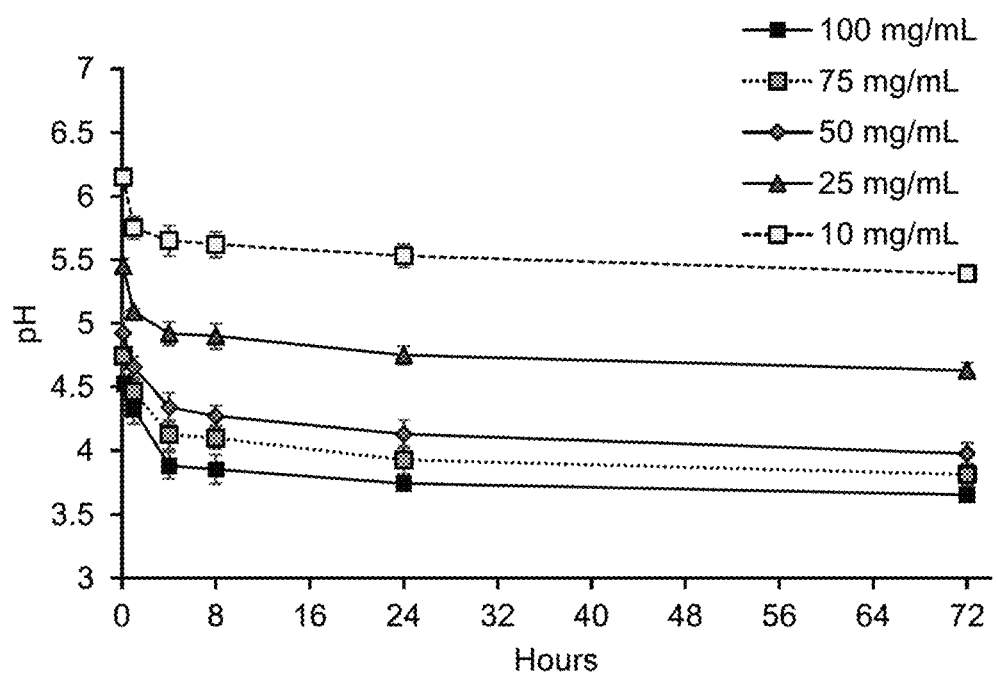
FIG. 26 is a graph showing the pH measured over 72 hours of the synthetic antibacterial minerals at the same varying concentrations as FIG. 24.
Figure 27A:
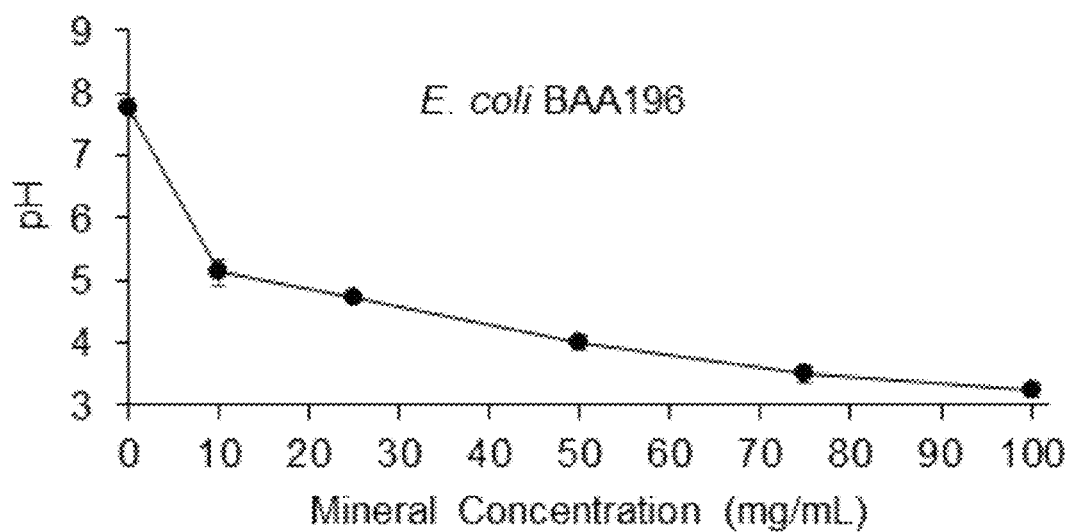
FIGS. 27A-27F are graphs showing the pH over 24 hours at 100, 75, 50, 25, and 10 mg/ml concentrations of synthetic antibacterial minerals in the presence of various gram-negative bacteria.
Figure 27B:
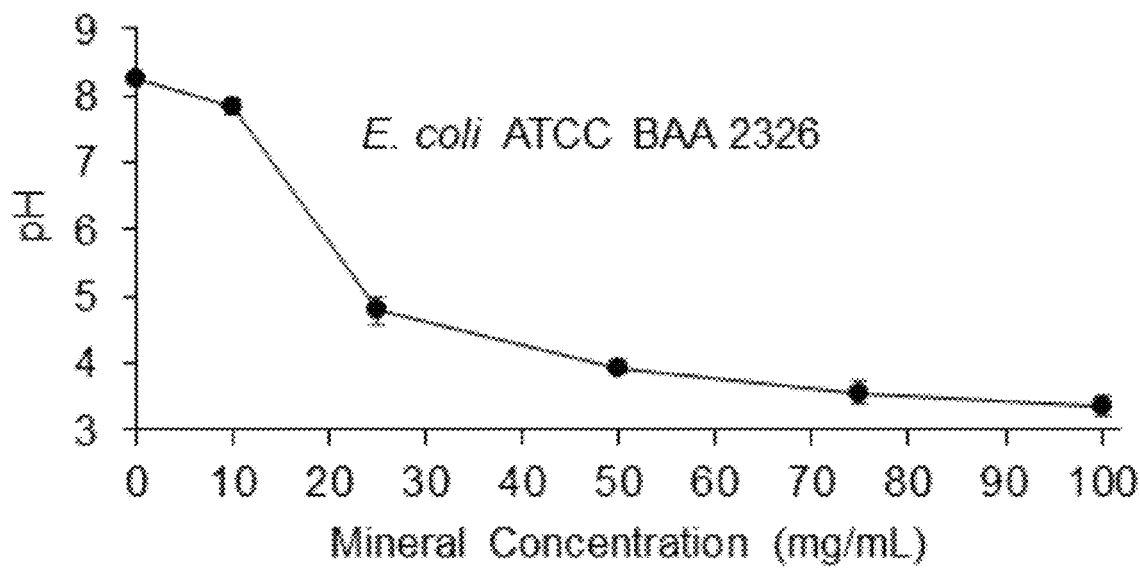
Figure 27C:
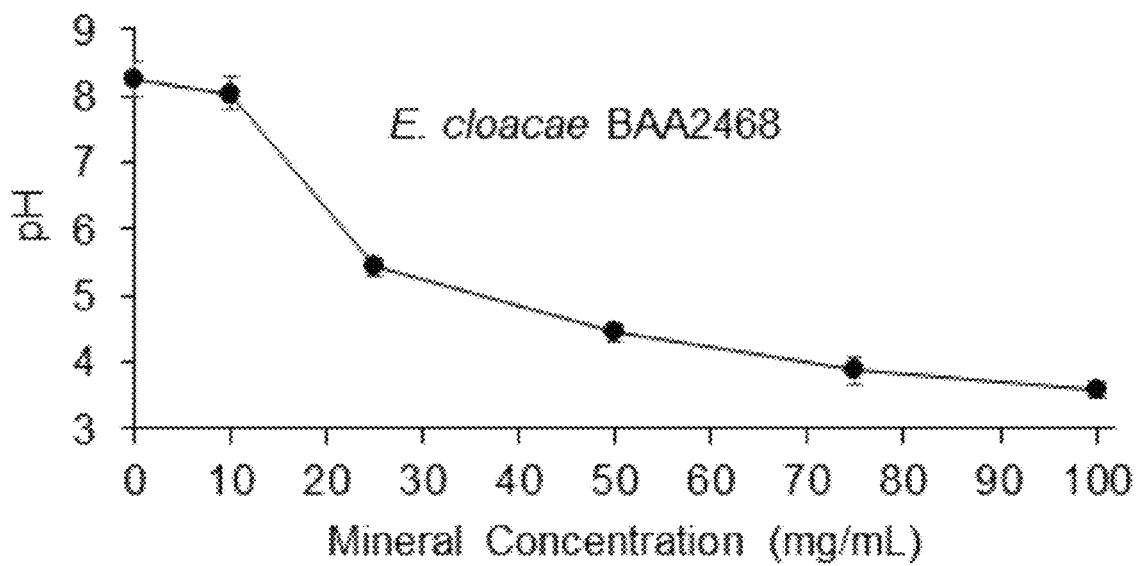
Figure 27D:
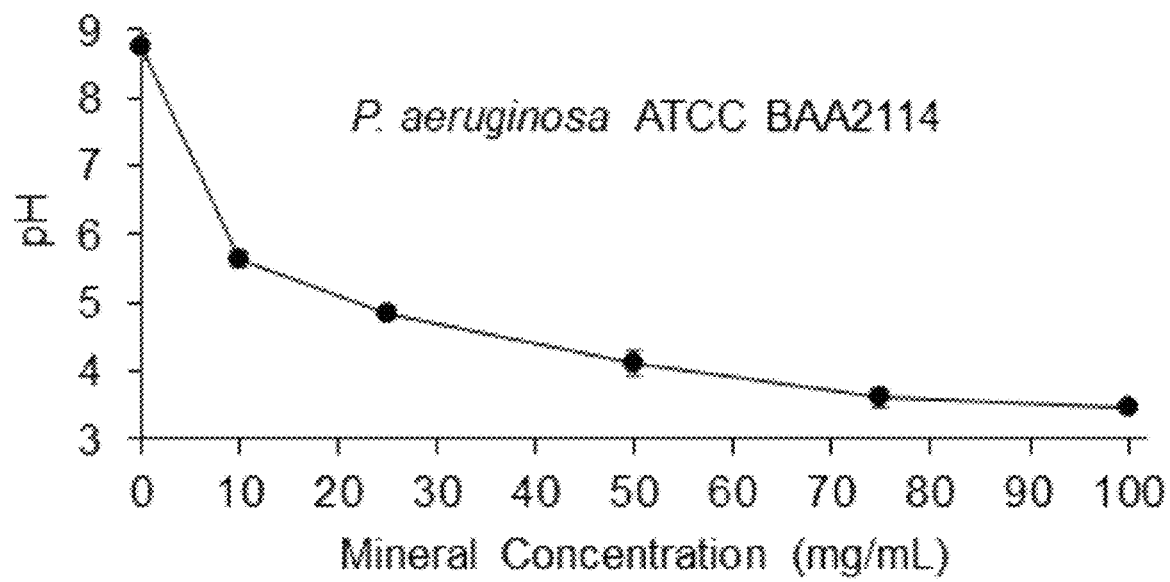
Figure 27E:
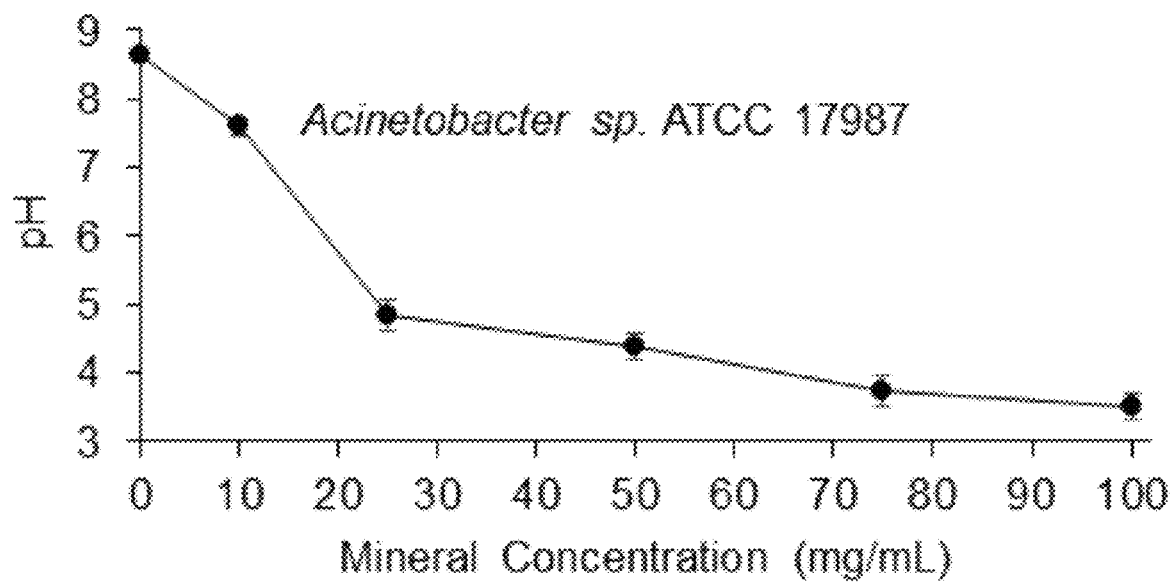
Figure 27F:
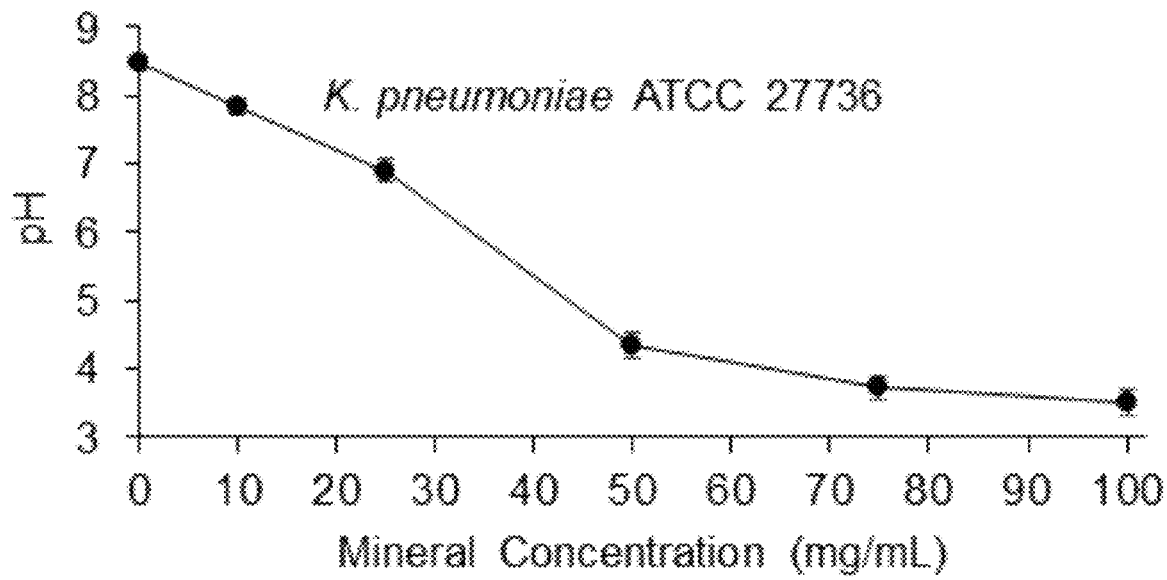
Figure 28A:
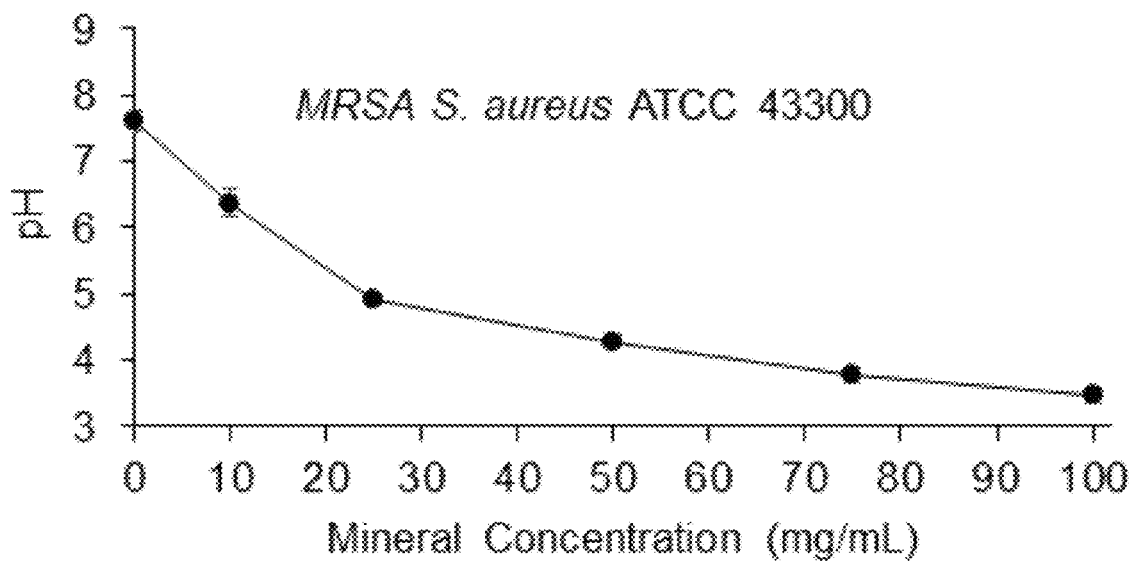
FIGS. 28A-28E are graphs the pH over 24 hours at 100, 75, 50, 25, and 10 mg/ml concentrations of synthetic antibacterial minerals in the presence of various gram-positive bacteria.
Figure 28B:
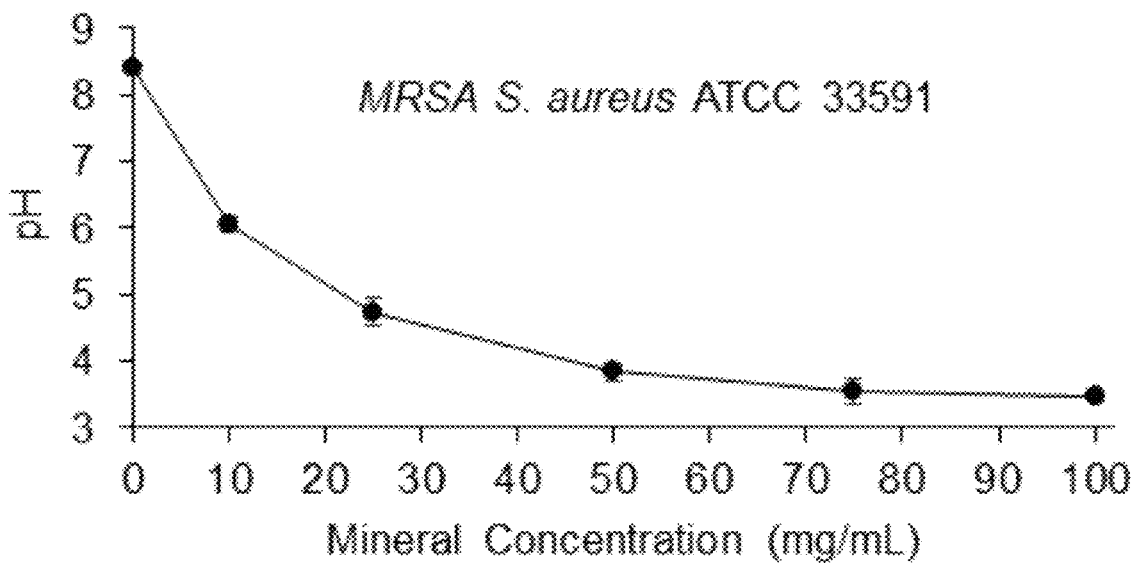
Figure 28C:
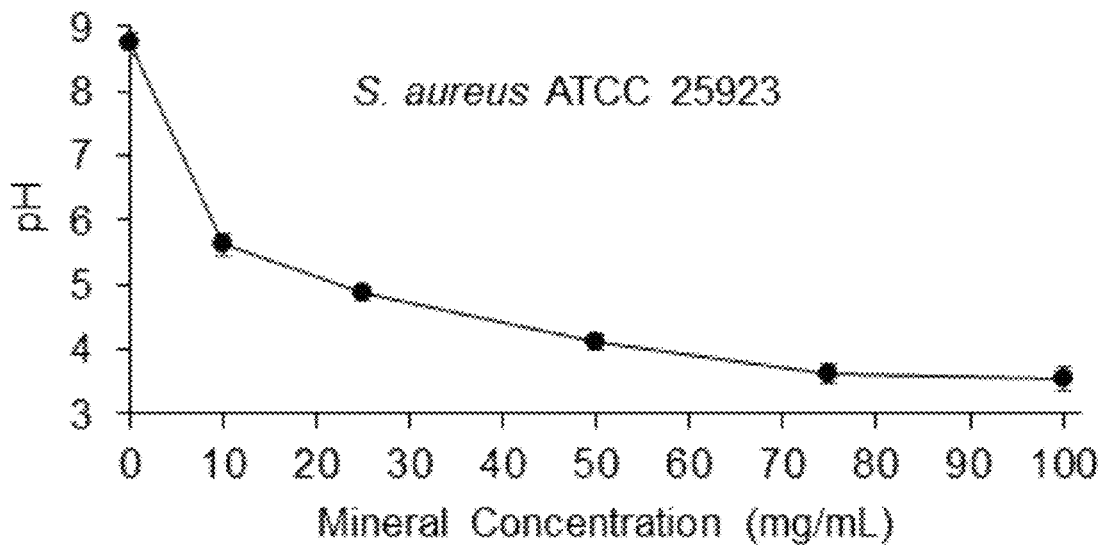
Figure 28D:
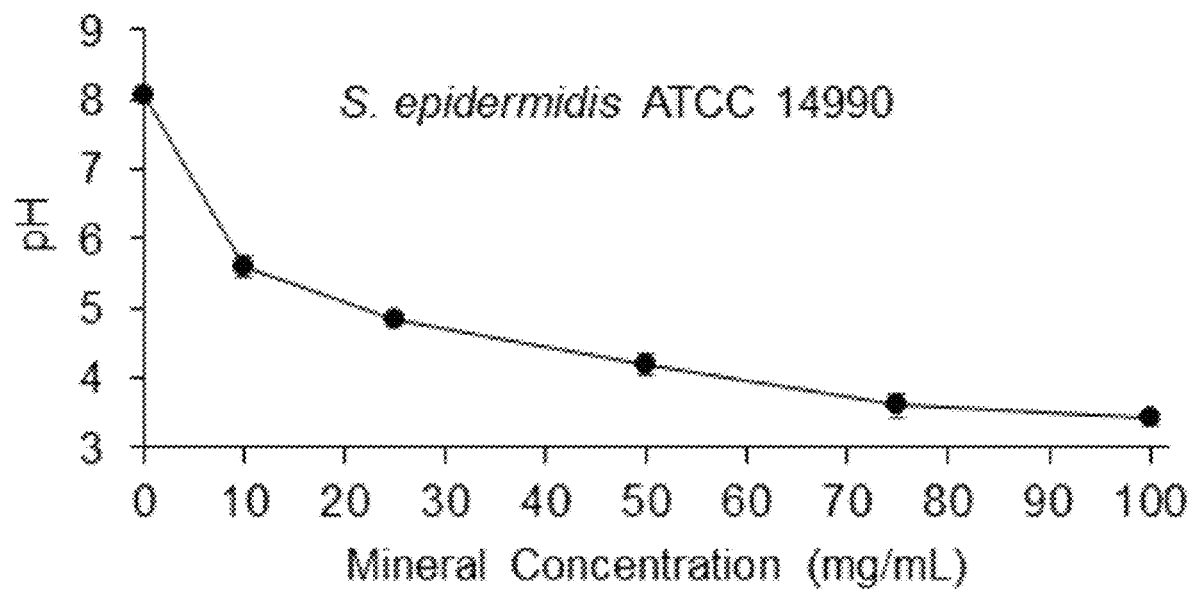
Figure 28E:
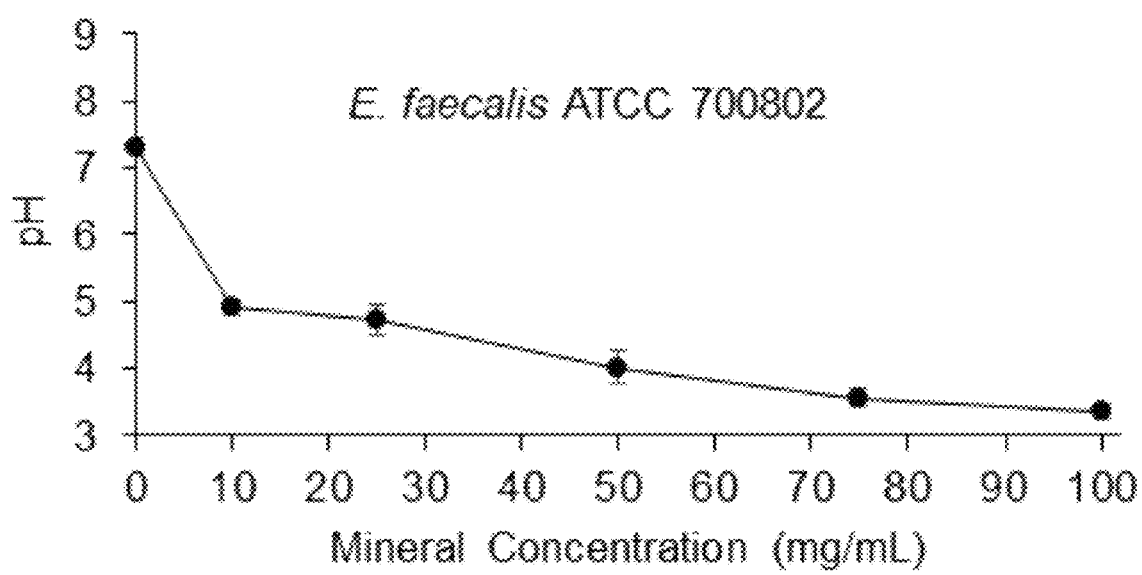

FIG. 26 shows the pH measured over 72 hours of the synthetic antibacterial minerals at the same varying concentrations. This demonstrated that the mineral dose buffered pH from the media initial starting pH of 6.5 to 3.5 over 72 hours across the tested concentrations.

FIGS. 27A-27F shows the pH over 24 hours at 100, 75, 50, 25, and 10 mg/ml concentrations of synthetic antibacterial minerals in the presence of various gram-negative bacteria. FIGS. 28A-28E shows the pH over 24 hours at 100, 75, 50, 25, and 10 mg/ml concentrations of synthetic antibacterial minerals in the presence of various gram-positive bacteria.

Comparative Example 1

Figure 29:
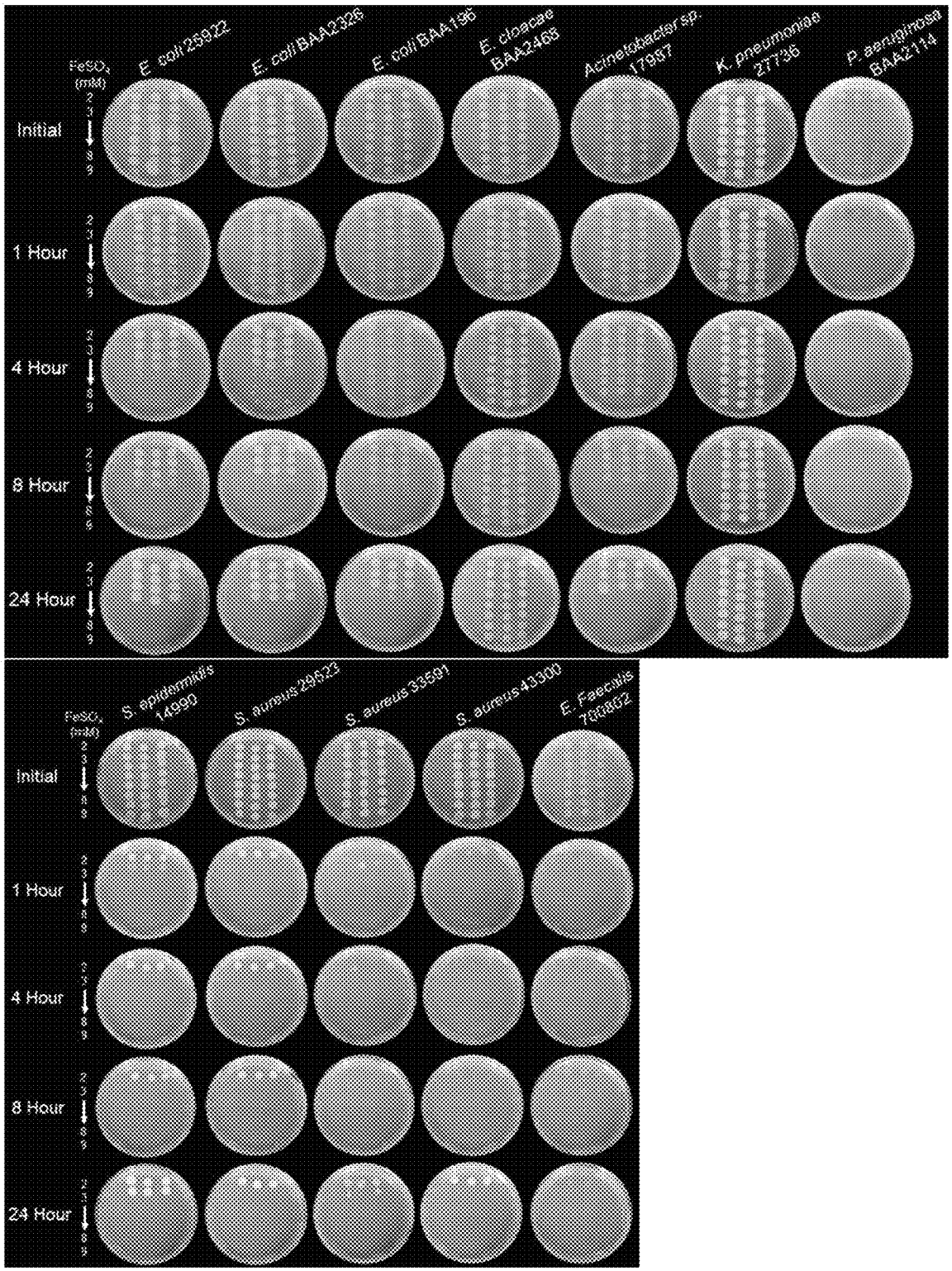
FIG. 29 is an image of ferrous sulfate MBC spot plates measured in triplicate for each bacterial strain growing in TSB media. Ferrous sulfate concentrations ranged from 2-9 mM in accordance with comparative example 1.

The bactericidal concentration needed when using an adjustment of $Fe^2$ concentration alone was tested for comparison to the compositions of the disclosure. Iron concentrations were adjusted through the addition of ferrous sulfate. Ferrous sulfate MBC spot plates were measured in triplicate for each bacterial strain in TSB media. Ferrous sulfate concentrations were tested at 2, 3, 4, 5, 6, 7, 8, and 9 mM as illustrated in FIG. 29. Table 4 illustrates the ferrous sulfate concentration for the various strains at the minimum bactericidal concentration measured over 24 hours.

TABLE 4

| | Time (Hours) | | | |
|---|---|---|---|---|
| | 1 | 4 | 8 | 24 |
| | $Fe^{2+}$ (mM) at MBC | | | |
| Gram-negative | | | | |
| Escherichia coli BAA-25922 | >9 | 8 | 6 | 6 |
| Escherichia coli BAA-2326 | >9 | 7 | 6 | 6 |
| Escherichia coli BAA-196 | >9 | >9 | >9 | 6 |
| Escherichia cloacae BAA-2468 | >9 | >9 | >9 | >9 |
| Acinetobacter sp. 17987 | >9 | >9 | 6 | 5 |
| Klebsiella pneumonia 27736 | >9 | >9 | >9 | >9 |
| Pseudomonas aeruginosa BAA-2114 | 5 | 4 | 4 | 4 |
| Gram-positive | | | | |
| Staphylococcus epidermidis 14990 | >9 | 4 | 4 | 4 |
| Staphylococcus aureus 25923 | 3 | 3 | 3 | 3 |
| MRSA 33591 | 4 | 4 | 4 | 4 |
| MRSA 43300 | 3 | 3 | 3 | 3 |
| Enterococcus faecalis 700802 | >9 | 7 | 7 | 3 |

As compared to the compositions of the disclosure, a significant increase in the concentration of $Fe^{2+}$ was needed when the iron source is provided from a metal solution alone. Without intending to be bound by theory, it is believed that the compositions of the disclosure, which include the combination of the $Fe^{2+}$-exchanged fluorinated synthetic smectite and synthetic semiconducting metal sulfide provide synergistic effect of the mineral mixture, redox cycling, $Fe^{2+}$ release and ROS generation that effectively kills pathogens, making resistance difficult to establish.

Comparative Example 2

Figure 30:
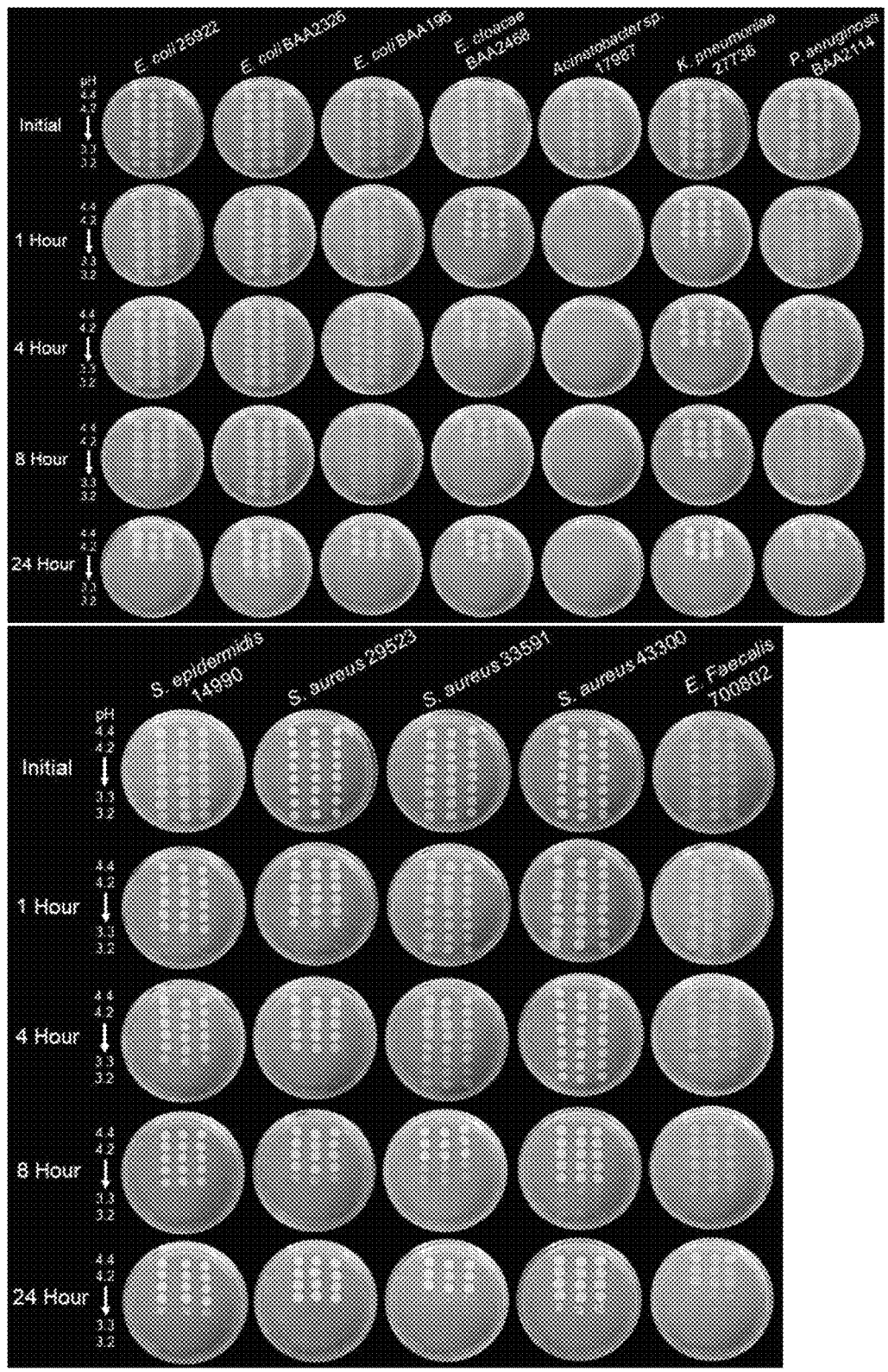
FIG. 30 is an image of pH MBC spot plates measured in triplicate for each bacterial strain growing in TSB media titrated with HCl for varying pH, pH ranged from 4.4 to 3.2 in accordance with comparative example 2.

Similar to comparative example 1, the bactericidal effect of changing pH alone was analyzed. Bacteria strains growing in TSB media were subject to pH effects through titration of HCl into the media. FIG. 30 illustrates the pH MBC spot plates measured in triplicate for each bacterial strain growing in TSB media. The pH ranged from 4.4 to 3.2. Table 3 shows the pH for the various strains at the minimum bactericidal concentration measured over 24 hours.

TABLE 3

| | Time (Hours) | | | |
|---|---|---|---|---|
| | 1 | 4 | 8 | 24 |
| | pH at MBC | | | |
| Gram-negative | | | | |
| Escherichia coli BAA-25922 | <3.2 | <3.2 | 3.2 | 3.7 |
| Escherichia coli BAA-2326 | <3.2 | <3.2 | <3.2 | 3.4 |
| Escherichia coli BAA-196 | <3.2 | <3.2 | <3.2 | 3.7 |
| Escherichia cloacae BAA-2468 | 3.4 | 3.6 | 3.6 | 3.7 |
| Acinetobacter sp. 17987 | 4.2 | 4.4 | 4.4 | 4.4 |
| Klebsiella pneumonia 27736 | 3.4 | 3.6 | 3.6 | 3.7 |
| Pseudomonas aeruginosa BAA-2114 | <3.2 | <3.2 | <3.2 | 4.00 |
| Gram-positive | | | | |
| Staphylococcus epidermidis 14990 | <3.2 | 3.3 | 3.4 | 3.4 |
| Staphylococcus aureus 25923 | <3.2 | 3.4 | 3.4 | 3.6 |
| MRSA 33591 | <3.2 | <3.2 | <3.2 | 3.6 |
| MRSA 43300 | <3.2 | <3.2 | <3.2 | 3.4 |
| Enterococcus faecalis 700802 | <3.2 | <3.2 | 3.3 | 3.6 |

Significantly more acidic pH (<3.5) is required to reach bactericidal levels as compared to the compositions of the disclosure, which were found to have a bactericidal effect at pH 4-5.5. This can be particularly advantageous in topical formulations, where significantly acid pH can be harmful or otherwise adverse to the skin, wound, or other application target.

Example 9—Murine Fibroblast (NIH 3T3) Susceptibility Testing

Murine fibroblast (NIH 3T3) susceptibility testing with the antibacterial minerals was performed in trans well plates with a 0.4 μm filter membrane. The antibacterial mineral composition included $Fe^{2+}$-exchanged fluorinated hectorite (exchanged with 30 mM $Fe^{2+}SO_4$) with 5 wt % pyrite. The antibacterial mineral composition was tested against fibroblasts growing in RPMI media. Minerals were resuspended in 1.8% NaCl at concentrations of 20, 50, and 100 mg/mL and added to transwell plates with fibroblast growing in RPMI media at a 1:1 ratio. The final mineral concentrations were 10, 25, and 50 mg/mL. After 4 hours of exposure to the antibacterial minerals, the transwell plates containing the mineral phases were removed along with the RPMI media and fresh RPMI media was added. Cell recovery was quantified by Brightfield microscopy imaging and extraction of total DNA.

Figure 31:
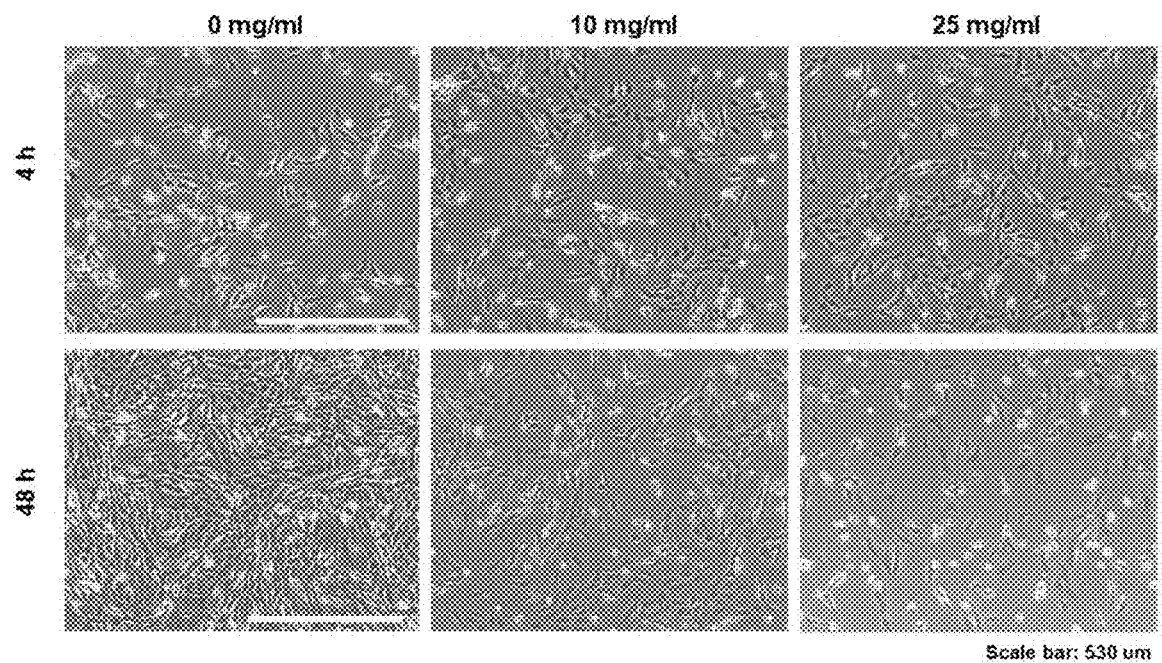
FIG. 31 is an image showing murine fibroblast (NIH T3T) growth after 4 hours and 48 hours of mineral exposure at 10 and 25 mg/mL.
Figure 32:
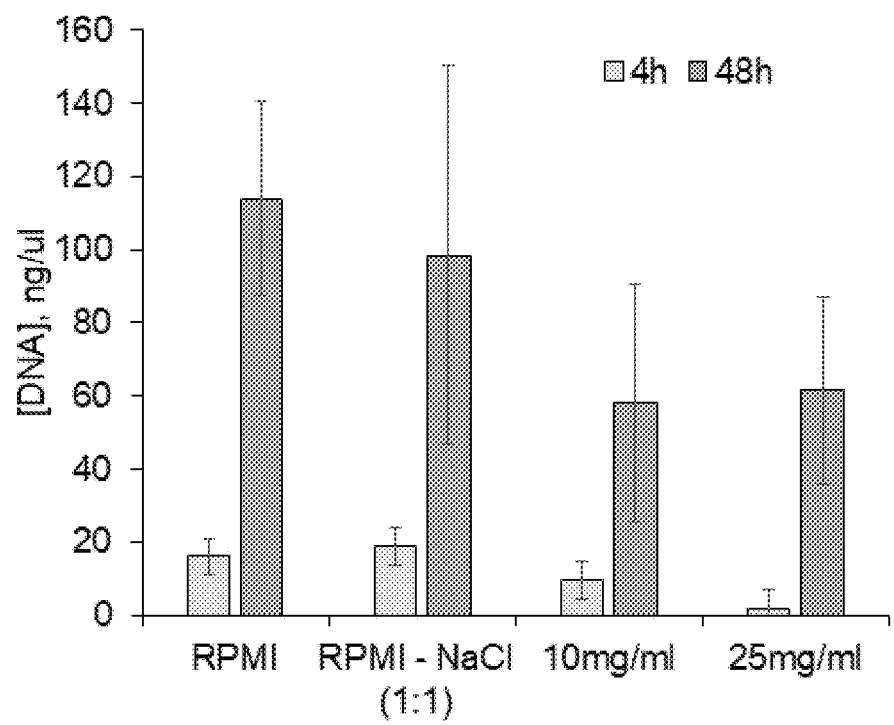
FIG. 32 is a graph showing the DNA quantification from viable fibroblasts collected after the 4 and 48 hour growth periods in complete media (RPMI), mixed media containing RPMI and 0.9% NaCl, and following mineral exposure at 10 mg/ml and 25 mg/ml.

FIG. 31 shows the murine fibroblast (NIH T3T) growth after 4 hours and 48 hours of mineral exposure at 10 and 25 mg/mL. FIG. 32 shows the DNA quantification from viable fibroblasts collected after the 4 and 48 hour growth periods.

Figures 33A, 33B, 33C:
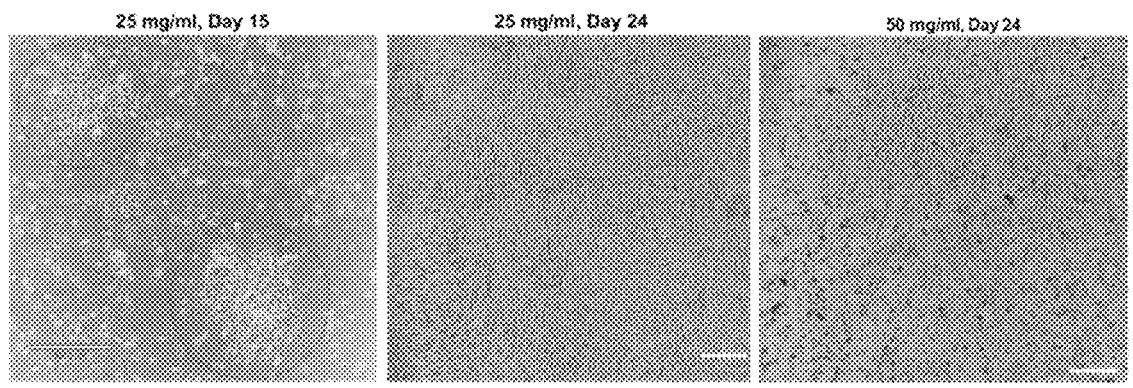
FIGS. 33A to 33C are images showing 3T3 murine fibroblast growth 15 and 24 days after exposure to 25 mg/mL mineral composition and 24 days after exposure to 50 mg/mL mineral composition. Circles in FIG. 33A represent clonal expansion of cells.
Figure 34:
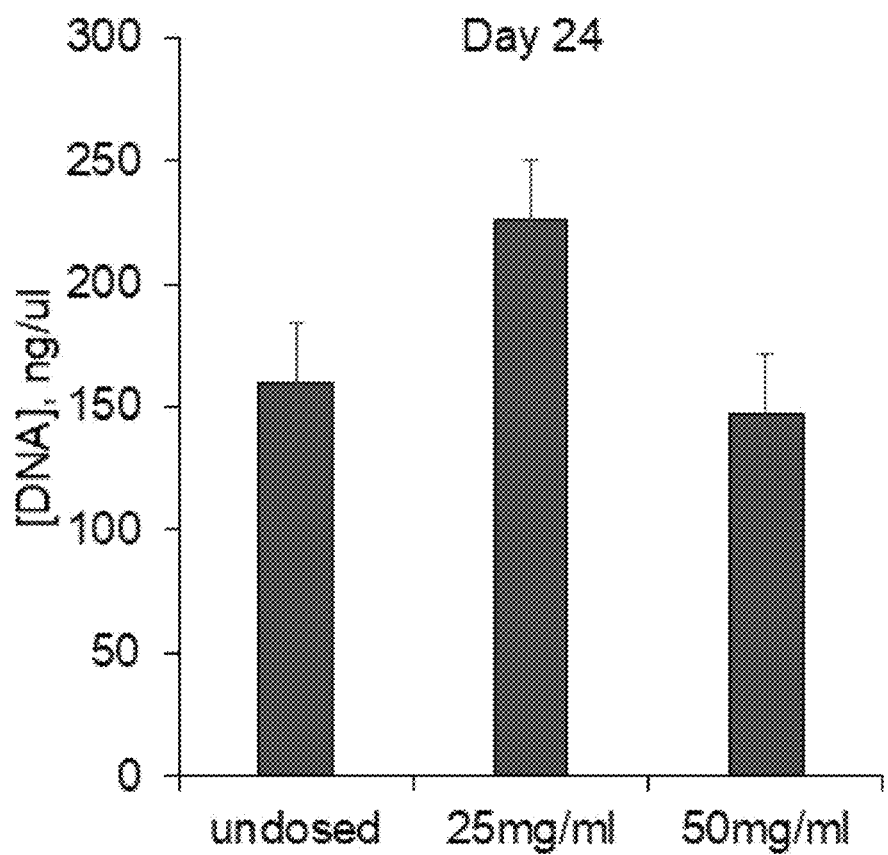
FIG. 34 is a graph showing the DNA quantification at day 24 following 0 mg/ml (undosed, control), 25 mg/mL, and 50 mg/mL exposure to the mineral composition.

FIGS. 33A to 33C shows 3T3 murine fibroblast growth 15 and 24 days after exposure to 25 mg/mL mineral composition and 24 days after exposure to 50 mg/mL mineral composition. The fibroblast were exposed to the mineral composition for 4 hours. Referring to FIG. 33A, the murine fibroblasts began to clonal expand (see circles in the image) by day 15. Referring to FIG. 33B, the fibroblast continued to divide and reached confluency by day 24. FIG. 33C shows that 60-70% confluency was reached by day 24 post exposure to the 50 mg/mL mineral composition. FIG. 34 shows the DNA quantification at 24 following 0 mg/ml (undosed, control), 25 mg/mL, and 50 mg/mL exposure to the mineral composition.

The fibroblasts survived acute toxicity to the mineral composition at 10 mg/mL, 25 mg/mL, and 50 mg/mL concentrations over 4 hours exposure. The cells began to proliferate and expand by day 15 after treatment with the minimum microbial inhibitory concentration (MIC) for bacterial growth, which was 25 mg/mL. It was determined that recovery of the cells in the absence of the mineral composition was needed for cell viability.

Prophetic Example 1

Efficacy of a pharmaceutical composition in accordance with the disclosure in treating a gastrointestinal infection will be evaluated in an animal model using 6 to 8 week old CD-1 1SG outbred mice. Prior to gastrointestinal infections, the mice will be given drinking water containing 5 g/L streptomycin sulfate for 24 hours to eliminate facultative bacterial and eliminate competing species during infection with *E. coli*. Gastrointestinal infection will be induced by dosing with ESBL *E. coli* ATCC BAA-2326 by mouth after fasting. After 24 hours, once the infection has been established, the mice will be treated with an antibacterial mineral composition in accordance with the disclosure at various concentrations ranging from 25 mg/mL to 400 mg/mL. Administration will be done orally either as a single dose or every 2 days.

The health of the mice will be observed daily and the mice will be weighed daily. The mice will be euthanized at the end of the study or for humane endpoint reasons. Tissue samples will be collected, homogenized, and plated for bacterial CFU and isolated for bacterial copy number analysis by PCR. Blood, spleen, liver, and intestine samples will be collected.

It is believed that administration of the antibacterial mineral compositions in accordance with disclosure will reduce the bacterial CFU present in the treated mice as comparted to the control and the compositions will demonstrate efficacy in treating the induced GI infection. Additionally, the high surface area negatively charged smectite minerals will adsorb bacterial toxins, while redox cycling and ROS will oxidize and eliminate the adsorbed bacterial toxins.

Prophetic Example 2

Antibacterial compositions in accordance with the disclosure will be evaluated for treatment of a skin infection using a mouse animal model using 6 to 8 week old SKH-1 hairless mice. An abrasion will be produced on the mice. A 1 $cm^2$ skin wound will be scraped onto the backs of the mice, taking care not to cut through the skin. The wound will then be inoculated with MRSA (strain ATCC 4330). Control wounds will be inoculated with bacteria resuspended in sterile PBS. The inoculated wounds will then be covered for 24-72 hours to allow the MRSA infection to form a biofilm.

The infection will be treated with an antibacterial mineral composition in accordance with the disclosure using a hydrated poultice as the dosage form. Both continuous and single dose dosing regimens will be tested. The hydrated poultice will have a concentration of the antibacterial mineral composition ranging from 25 mg/mL to 400 mg/mL. The wound will be treated once after biofilm formation, which is then removed after 24 hours by irrigation, or applied every time the wound is managed until wound closure.

Wounds and coverings will be examined daily for infectious charge, healing, and loss or damage of wound covering. All mice will be euthanized at the study end point or for humane endpoint reasons. Tissue samples will be collected, homogenized, and plated for bacterial CFU and isolated for bacterial copy number analysis by PCR.

It is believed that the treatment with topical antibacterial mineral compositions in accordance with the disclosure will reduce the healing time as compared to MRSA infected, untreated wounds. The MRSA infected wounds are not expected to heal without medicinal treatment. Chronic non-healing skin wounds infected with antibiotic resistant bacteria exhibit an alkaline pH environment that prevents the release of oxygen from hemoglobin, causing the wound to become septic and produce necrotic tissue. Healthy skin has an acidic pH with values ranging from pH 4-6. The immune system utilizes macrophages and neutrophils to engulf invading pathogens and release a burst of ROS that kills the bacterial infection. This burst of ROS cannot occur in septic tissues at alkaline pH, and leads to further infection and tissue necrosis from bacterial infection. The application of antibacterial mineral compositions will kill the invading pathogens while buffering the pH of the wound to levels that allow infected tissues to become re-oxygenated by blood cells. The antibacterial mineral compositions will engulf the invading bacterial pathogens and release a burst of ROS, similar to the human immune response. Additionally, the high surface area negatively charged smectite minerals will adsorb bacterial toxins, while redox cycling and ROS will oxidize and eliminate the adsorbed bacterial toxins.

The technical information set out herein may in some respects go beyond the disclosure of the invention, which is defined exclusively by the appended claims. The additional technical information is provided to place the actual invention in a broader technical context and to illustrate possible related technical developments. Such additional technical information which does not fall within the scope of the appended claims, is not part of the invention.

While particular embodiments of the present invention have been shown and described in detail, it will be obvious to those skilled in the art that changes and modifications may be made without departing from the invention in its broader aspects. Therefore, the aim is to cover all such changes and modifications as fall within the true spirit and scope of the invention. The matters set forth in the foregoing description and accompanying drawings are offered by way of illustration only and not as limitations. The actual scope of the invention is to be defined by the subsequent claims when viewed in their proper perspective based on the prior art.

What is claimed is:

1. A pharmaceutical composition comprising $Fe^{2+}$-exchanged fluorinated synthetic smectite and synthetic semiconducting metal sulfide, wherein the $Fe^{2+}$-exchanged fluorinated synthetic smectite comprises interlayer $Fe^{2+}$, and when administered the interlayer $Fe^{2+}$ is released from interlayer spaces of the $Fe^{2+}$-exchanged fluorinated synthetic smectite.

2. The composition of claim 1, wherein the $Fe^{2+}$-exchanged fluorinated synthetic smectite is present in an amount of 80 wt % to 98.5 wt %, based on the total weight of the composition and wherein the synthetic semiconducting metal sulfide is present in an amount of 1.5 wt % to 20 wt % based on the total weight of the composition.

3. The composition of claim 2, wherein the $Fe^{2+}$-exchanged fluorinated synthetic smectite is produced by exchange of a fluorinated synthetic smectite with 5 mM to 60 mM of a ferrous iron source.

4. The composition of claim 1, wherein the $Fe^{2+}$-exchanged fluorinated synthetic smectite, at an octahedral site, comprises $Li^+$.

5. The composition of claim 1, wherein the $Fe^{2+}$-exchanged fluorinated synthetic smectite, at an octahedral site, comprises $Mg^{2+}$, $Cu^{2+}$, $Zn^{2+}$, or $Fe^{2+}$.

6. The composition of claim 1, wherein the $Fe^{2+}$-exchanged fluorinated synthetic smectite comprises from 5 meq to 100 meq of ferrous iron ($Fe^{2+}$), per 100 g of the $Fe^{2+}$-exchanged fluorinated synthetic smectite.

7. The composition of claim 1, free of arsenic, lead, cobalt, nickel, mercury, or uranium.

8. The composition of claim 1, wherein the semiconducting metal sulfide comprises one or more of synthetic pyrite, synthetic acanthite, synthetic chalcocite, synthetic bornite, synthetic sphalerite, synthetic chalcopyrite, and synthetic marcasite.

9. The composition of claim 1, wherein the semiconducting metal sulfide is present in amount of 5 wt % to 20 wt % based on the total weight of the composition.

10. The composition of claim 9, wherein the $Fe^{2+}$-exchanged fluorinated synthetic smectite is produced by exchange of a fluorinated synthetic smectite with 20 mM to 150 mM of a ferrous iron source.

11. A wound dressing comprising the composition of claim 1 suspended in a hydrogel.

12. An article of personal protective equipment comprising the composition of claim 1.

13. A 3D-printed article comprising the composition of claim 1 and a siloxane resin.

14. A method of treating an infection, comprising administering the pharmaceutical composition of claim 1 to a subject in need thereof.

15. The method of claim 14, wherein the composition is administered orally or topically.

16. The method of claim 14, wherein upon administration, the composition maintains an Eh value of about 400 mV to about 900 mv for at least 24 hours.

17. The method of claim 14, wherein the infection is a topical infection.

18. The method of any one of claims 17, wherein the topical infection is a bacterial infection, a fungal infection, or acne.

19. The method of claim 14, wherein the infection is a gastrointestinal infection.

20. The method of claim 19, wherein the gastrointestinal infection is dysentery.

21. The method of claim 14, wherein the infection is a bacterial infection comprising antibiotic resistant bacteria, and the antibiotic resistant bacteria is selected from the group consisting of *Enterococcus faecium, Staphylococcus aureus, Klebsiella pneumonia, Acinetobacter baumannii, Pseudomonas aeruginosa, Enterobacter, Escherichia coli,* extended-spectrum beta lactamase positive (ESBL) *Escherichia coli, Salmonella enterica* serotype *typhimurium,* a methicillin-resistant *Staphylococcus aureus* (MRSA), *Staphylococcus epidermidis,* methicillin-resistant *Staphylococcus epidermidis* (MRSE), *Propionibacterium acnes, Clostridiodies difficile, Listeria monocytogenes, Pasteurella multocida, Proteus vulgaris, Bacillus cereus, Bordetella bronchiseptica,* and any combination thereof.

* * * * *